(12) United States Patent
Langenfeld

(10) Patent No.: US 7,473,561 B2
(45) Date of Patent: Jan. 6, 2009

(54) BONE MORPHOGENETIC PROTEIN-2 IN THE TREATMENT AND DIAGNOSIS OF CANCER

(75) Inventor: John Langenfeld, Flemington, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 267 days.

(21) Appl. No.: 11/435,852

(22) Filed: May 17, 2006

(65) Prior Publication Data

US 2006/0198844 A1 Sep. 7, 2006

Related U.S. Application Data

(60) Division of application No. 10/692,824, filed on Oct. 23, 2003, now abandoned, which is a continuation-in-part of application No. 10/044,716, filed on Jan. 11, 2002, now abandoned.

(60) Provisional application No. 60/261,252, filed on Jan. 12, 2001.

(51) Int. Cl.
   *G01N 33/566* (2006.01)
(52) U.S. Cl. .............................. 436/501; 530/350; 435/4
(58) Field of Classification Search .................. 436/501; 435/4; 530/350
   See application file for complete search history.

(56) References Cited

U.S. PATENT DOCUMENTS 6,548,633 B1* 4/2003 Edwards et al. ............. 530/300

OTHER PUBLICATIONS

Raida et al. (J. Cancer Res. Clin. Oncol. 2005; 131: 741-750).*
Soda et al. (Anticancer Drugs. Apr. 9, 1998;(4):327-331).*
Langenfeld et al. (Carcinogenesis. Sep. 2003;24(9):1445-1454).*
Langenfeld et al. (Mol. Cancer Res. Mar. 2004; 2:141-149).*
Raida et al. (Int. J. Mol. Med. 2006; 18:Sep. 24, 2003: 735-739).*
Feely et al. (Bone. Feb. 2006; (2): 154-166).*
Asano et al. (J. Bone Joint Surg. Br. May 2004; 86 (4): 607-612).*
Namiki et al. (J. Biol. Chem. Aug. 1997; 272 (35): 22046-22052).*
Langenfeld et al. (Ann. Thorac. Surg. Sep. 2005; 80 (3): 1028-1032).*
Abe et al., "Essential Requirement of BMPs-2/4 for Both Osteoblast and Osteoclast Formation in Murine Bone Marrow Cultures from Adult Mice: Antagonism by Noggin", Journal of Bone and Mineral Research 2000 15(4) :663-673.
An et al., "Recombinant human bone morphogenetic protein-2 induces a hematopoietic microenvironment in the rat that supports the growth of stem cells", Experimental Hematology 1996 24:768-775.
Brunet et al., "Noggin, Cartilage Morphogenesis, and Joint Formation in the Mammalian Skeleton", Science 1998 280:1455-1457.
Capdevila et al., "Endogenous and Ectópic Expression of noggin Suggests a Conserved Mechanism for Regulation of BMP Function during Limb and Somite Patterning", Development Biology 1998 197:205-217.
Chen et al., "Suppression of Tumor Necrosis Factor-mediated Apopsosis by Nuclear FactorÞB-independent Bone Morphogenetic Protein/Smad Signaling", Journal Biological Chemistry 2001(42):39259-39263.
Cunningham et al., "Osteogenin and recombinant bone morphogenetic protein 2B are chemotactic for human monocytes and stimulate transforming growth factor $\beta_1$ mRNA expression", Proc. Natl. Acad. Sci. USA 1992 89:11740-11744.
Glavic et al., "*Xiro-1* Controls Mesoderm Patterning by Repressing *bmp 4* Expression in the Spemann Organizer", Developmental Dynamics 2001 222:368-376.
Guo et al., "Expression of Bone Morphogenetic Proteins and Receptors in Sarcomas", Clin. Orthop. 1999 1(365):175-183.
Hatakeyama et al., "Expression of Bone Morphogenetic Proteins of Human Neoplastic Epithelial Cells", Biochemistry and Molecular Biology International 1997 42(3):497-505.
Hollnagel et al., "*Id* Genes Are Direct Targets of Bone Morphogenetic Protein Induction in Embryonic Stem Cells", Journal Biological Chemistry 1999 274(28)19838-19845.
Kleeff et al., "Bone Morphogenetic Protein 2 Exerts Diverse Effects on Cell Growth In Vitro and Is Expressed in Human Pancreatic Cancer in Vivo", Gastroenterology 1999 116:1202-1216.
Liu et al., "Angiogenin Activates Erk ½ in Human Umbilical Vein Endothelial Cells", Biochemical and Biophysical Research Communications 2001 287:305-310.
Lockliin et al., "Assessment of Gene Regulation by Bone Morphogenetic Protein 2 in Human Marrow Stromal Cells Using Gene Array Technology", Journal of Bone and Mineral Research 2001 16(12):2192-2204.
Millet et al., "The human *chordin* gene encodes several differentially expressed spliced variants with distinct BMP opposing activities", Mechanisms of Development 2001 106:85-96.
Ogata et al., "Bone morphogenetic protein 2 transiently enhances expression of a gene, Id(inhibitor of differentiation), encoding a helix-loop-helix molecule", Proc. Natl. Acad. Sci. USA 1993 90:9219-9222.

(Continued)

*Primary Examiner*—Stephen L Rawlings
(74) *Attorney, Agent, or Firm*—Licata & Tyrrell P.C.

(57) ABSTRACT

The present invention pertains to the use of BMP-2, which is overexpressed in most common cancers, as 1) a target for cancer treatment therapies and 2) a means to diagnose cancer. The therapeutic component of this invention involves administering to a patient a composition that inhibits bone morphogenetic-2 activity. Such inhibition may be accomplished by ligands or antibodies that bind to BMP-2 or BMP-2 receptors. It may also be achieved by preventing the processing of pro-BMP-2, or blocking transcription or replication of BMP-2 DNA or translation of BMP-2 mRNA. The diagnostic component of the invention involves measuring the BMP-2 level in biological samples from both a patient and a subject and comparing those levels. Elevated levels of BMP-2 in the patient compared to the non-cancerous subject indicate cancer.

1 Claim, 30 Drawing Sheets

OTHER PUBLICATIONS

Schindl et al., "Level of Id-1 Protein Expression Correlates with Poor Differentiation, Enhanced Malignant Potential, and More Aggressive Clinical Behavior of Epithelial Ovarian Tumors", Clinical Cancer Research 2003 9:779-785.

Tucker et al., "Transformation of Tooth Type Induced by Inhibition of BMP Signaling", Science 1998 282:1136-1138.

Weaver et al., "Bmp signaling regulates proximal-distal differentiation of endoderm in mouse lung development", Development 1999 126:4005-4015.

Willette et al., "BMP-2 Gene Expression and Effects on Human Vascular Smooth Muscle Cells", J Vasc Res 1999 36:120-125.

Zebedee et al., "Id proteins in cell cycle control and cellular senescene", Onogene 2001 20:8317-8325.

Zimmerman et al., "The Spemann Organizer Signal noggin Binds and Inactivates Bone Morphogenetic Protein 4", Cell 1996 86:599-606.

Benezra et al., "The Id proteins and angiogenesis", Oncogene 2001 20:8334-8341.

Cameron et al., "Polyarginines Are Potent Furin Inhibitors", J. Biol. Chem. 2000 275(47):36741-36749.

Deckers et al., "Bone Morphogenetic Proteins Stimulate Angiogenesis through Osteoblast-Derived Vascular Endothelial Growth Factor A", Endocrinology 2002 143(4):1545-1553.

Gerber et al., "Angiogenesis and Bone Growth", Trends Cardiovasc Med 2000 10:223-228.

Hay et al., "Bone Morphogenetic Protein-2 Promotes Osteoblast Apoptosis through a Smad-independent, Protein Kinase C-dependent Signaling Pathway", J. Biol. Chem. 2001 276(31):29028-29036.

Ide et al., "Cloning of human bone morphogenetic protein type IB receptor (BMPR-IB) and its expression in prostate cancer in comparison with other BMPRs", Oncogene 1997 14:1377-1382.

Izumi et al., "Bone Morphogenetic Protein-2 Inhibits Serum Deprivation-induced Apoptosis of Neonatal Cardiac Myocytes through Activation of the Smad1 Pathway", J. Biol. Chem. 2001 276(33):31133-31141.

Kirsch et al., "BMP-2 antagonists emerge from alterations in the low-affinity binding epitope for receptor BMPR-II", The EMBO Journal 2000 19(13):3314-3324.

Korchynskyi et al., "Identification and Functional Characterization of Distinct Critically Important Bone Morphogenetic Protein-specific Response Elements in the Id1 Promoter", J. Biol. Chem. 2002 277 (7):4883-4891.

Liu et al., "Human Type II Receptor for Bone Morphogenic Proteins (BMPs):Extension of the Two-Kinase Receptor Model to the BMPs", Molecular and Cellular Biology 1995 15(7):3479-3486.

Oro et al., "Basal Cell Carcinomas in Mice Overexpressing Sonic Hedgehog", Science 1997 276:817-821.

Sloan et al., "Stimulation of the dentine-pulp complex of rat incisor teeth by transforming growth factor-$\beta$ isoforms 1-3 in vitro", Archives of Oral Biology 1999 44:149-156.

Wu et al., "Utilization of Distinct Signaling Pathways by Receptors for Vascular Endothelial Cell Growth Factor and Other Mitogens in the Induction of Endothelial Cell Proliferation", J. Biol. Chem. 2000 275(7):5096-5103.

Yeh et al., "Osteogenic protein-1 increases gene expression of vascular endothelial growth factor in primary cultures of fetal rat calvaria cells", Molecular and Cellular Endocrinology 1999 153:113-124.

Zetter et al., "Angiogenesis and Tumor Metastasis", Annu. Rev. Med. 1998 49:407-424.

Meric et al., "Zd 1839 "Iressa"", Bull Cancer 2000 87(12):873-876.

* cited by examiner c

1. Alpha-1-antitrypsin

2. Bone Morphogenetic Protein 2

3. Cytokeratin 6

4. Lambda Light Chain

RT-PCR for BMP-2 in Human Lung Tumors

Western Blot of Serum Samples of Lung Cancer Patients

BMP Enhances Blood Vessel Formation as Compared to Controls

BMP-2 Enhances Tumor Vasculature

BMP-2 Regulated Sonic Hedgehog

12(a)

12(b)

FIGURE 13 (c) and 13 (d)
13(c)
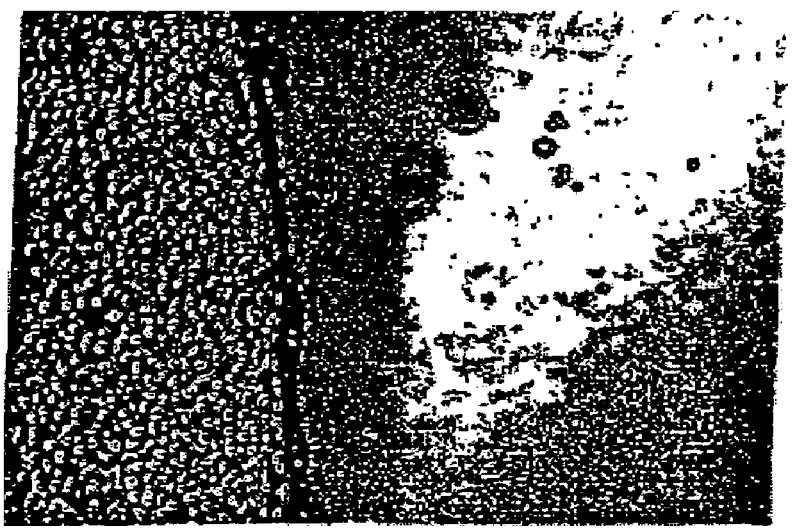
13(d)
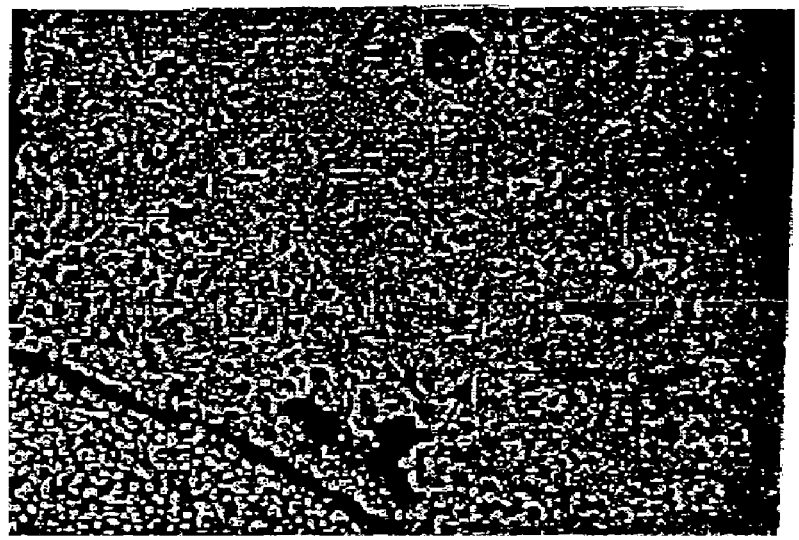

Noggin Inhibits VEGF Expression in the A549 Lung Cancer Cell Line

15(a)

15(b)

| | Secreted VEGF (ng/ml) |
|---|---|
| A540 + PBS | 13,333 |
| A549 + 300 ng/ml noggin | 9,442 |
| A549 + 500 ng/ml noggin | 8,219 |

|  | HAEC<br>% Cells w/ Smad 1/5/8 Nuclear Staining | HUVEC<br>% Cells w/ Smad 1/5/8 Nuclear Staining |
|---|---|---|
| Vehicle Control | 8.0 | 12.5 |
| 15 Min | 17.2 | 20.4 |
| 30 Min | 44.9 | 43.8 |
| 45 Min | 19.4 | 18.4 |
| 60 Min | 9.0 | 11.4 |

|  | 5% FCS<br><br>% Cells with Smad 1/5/8 Nuclear Staining | LHC-8 SFM<br><br>% Cells with Smad 1/5/8 Nuclear Staining |
|---|---|---|
| Vehicle Control | 3.3 | 2.0 |
| 15 Minutes | 6.9 | 1.9 |
| 30 Minutes | 18.0 | 2.5 |
| 120 Minutes | 4.5 | 1.8 |

SEQUENCE LISTING

```
<160> NUMBER OF SEQ ID NOS: 20

<210> SEQ ID NO 1
<211> LENGTH: 1547
<212> TYPE: DNA
<213> ORGANISM: Homo sapiens
<220> FEATURE:
<221> NAME/KEY: source
<222> LOCATION: (1)..(1547)
<223> OTHER INFORMATION: Homo sapiens:  Taxon:9606
<220> FEATURE:
<221> NAME/KEY: gene
<222> LOCATION: (1)..(1547)
<223> OTHER INFORMATION: BMP2
<220> FEATURE:
<221> NAME/KEY: CDS
<222> LOCATION: (324)..(1514)
<220> FEATURE:
<221> NAME/KEY: misc_feature
<222> LOCATION: (429)..(1127)
<223> OTHER INFORMATION: Region:  TGF-beta propeptide
<220> FEATURE:
<221> NAME/KEY: variation
<222> LOCATION: (432)..(432)
<223> OTHER INFORMATION: Allele = "T"; Allele = "G"
<220> FEATURE:
<221> NAME/KEY: variation
<222> LOCATION: (584)..(584)
<223> OTHER INFORMATION: Allele = "A"; Allele = "G"
<220> FEATURE:
<221> NAME/KEY: variation
<222> LOCATION: (893)..(893)
<223> OTHER INFORMATION: Allele = "T"; Allele = "A"
<220> FEATURE:
<221> NAME/KEY: misc_feature
<222> LOCATION: (1209)..(1511)
<223> OTHER INFORMATION: TGF-beta; Region:  Transforming growth factor
     beta like domain
<220> FEATURE:
<221> NAME/KEY: misc_feature
<222> LOCATION: (1209)..(1511)
<223> OTHER INFORMATION: TGFB; Region:  Transforming growth factor-
     beta (TGF-beta) family

<400> SEQUENCE: 1
```

-continued

```
ggggacttct tgaacttgca gggagaataa cttgcgcacc ccactttgcg ccggtgcctt      60
tgccccagcg gagcctgctt cgccatctcc gagccccacc gccctccac tcctcggcct     120 tgcccgacac tgagacgctg ttcccagcgt gaaagagag actgcgcggc cggcacccgg     180
gagaaggagg aggcaaagaa aaggaacgga cattcggtcc ttgcgccagg tccttttgacc    240 agagttttc catgtggacg ctctttcaat ggacgtgtcc ccgcgtgctt cttagacgga     300
ctgcggtctc ctaaaggtcg acc atg gtg gcc ggg acc cgc tgt ctt cta gcg    353
                        Met Val Ala Gly Thr Arg Cys Leu Leu Ala
                         1               5                  10
```

| | | | | | | | | | | |
|---|---|---|---|---|---|---|---|---|---|---|
| ttg | ctg | ctt | ccc | cag | gtc | ctc | ctg | ggc | ggc | gcg | gct | ggc | ctc | gtt | ccg | 401 |

Leu Leu Leu Pro Gln Val Leu Leu Gly Gly Ala Ala Gly Leu Val Pro
            15                  20                  25 gag ctg ggc cgc agg aag ttc gcg gcg gcg tcg tcg ggc cgc ccc tca      449
Glu Leu Gly Arg Arg Lys Phe Ala Ala Ala Ser Ser Gly Arg Pro Ser
         30                  35                  40 tcc cag ccc tct gac gag gtc ctg agc gag ttc gag ttg cgg ctg ctc      497
Ser Gln Pro Ser Asp Glu Val Leu Ser Glu Phe Glu Leu Arg Leu Leu
         45                  50                  55 agc atg ttc ggc ctg aaa cag aga ccc acc ccc agc agg gac gcc gtg      545
Ser Met Phe Gly Leu Lys Gln Arg Pro Thr Pro Ser Arg Asp Ala Val
 60                  65                  70 gtg ccc ccc tac atg cta gac ctg tat cgc agg cac tca ggt cag ccg      593
Val Pro Pro Tyr Met Leu Asp Leu Tyr Arg Arg His Ser Gly Gln Pro
75                  80                  85                  90 ggc tca ccc gcc cca gac cac cgg ttg gag agg gca gcc agc cga gcc      641
Gly Ser Pro Ala Pro Asp His Arg Leu Glu Arg Ala Ala Ser Arg Ala
             95                 100                 105 aac act gtg cgc agc ttc cac cat gaa gaa tct ttg gaa gaa cta cca      689
Asn Thr Val Arg Ser Phe His His Glu Glu Ser Leu Glu Glu Leu Pro
            110                 115                 120 gaa acg agt ggg aaa aca acc cgg aga ttc ttc ttt aat tta agt tct      737
Glu Thr Ser Gly Lys Thr Thr Arg Arg Phe Phe Phe Asn Leu Ser Ser
        125                 130                 135 atc ccc acg gag gag ttt atc acc tca gca gag ctt cag gtt ttc cga      785
Ile Pro Thr Glu Glu Phe Ile Thr Ser Ala Glu Leu Gln Val Phe Arg
    140                 145                 150 gaa cag atg caa gat gct tta gga aac aat agc agt ttc cat cac cga      833
Glu Gln Met Gln Asp Ala Leu Gly Asn Asn Ser Ser Phe His His Arg
155                 160                 165                 170 att aat att tat gaa atc ata aaa cct gca aca gcc aac tcg aaa ttc      881
Ile Asn Ile Tyr Glu Ile Ile Lys Pro Ala Thr Ala Asn Ser Lys Phe
                175                 180                 185 ccc gtg acc aga ctt ttg gac acc agg ttg gtg aat cag aat gca agc      929
Pro Val Thr Arg Leu Leu Asp Thr Arg Leu Val Asn Gln Asn Ala Ser
            190                 195                 200 agg tgg gaa agt ttt gat gtc acc ccc gct gtg atg cgg tgg act gca      977
Arg Trp Glu Ser Phe Asp Val Thr Pro Ala Val Met Arg Trp Thr Ala
        205                 210                 215 cag gga cac gcc aac cat gga ttc gtg gtg gaa gtg gcc cac ttg gag     1025
Gln Gly His Ala Asn His Gly Phe Val Val Glu Val Ala His Leu Glu
    220                 225                 230 gag aaa caa ggt gtc tcc aag aga cat gtt agg ata agc agg tct ttg     1073
Glu Lys Gln Gly Val Ser Lys Arg His Val Arg Ile Ser Arg Ser Leu
235                 240                 245                 250 cac caa gat gaa cac agc tgg tca cag ata agg cca ttg cta gta act     1121
His Gln Asp Glu His Ser Trp Ser Gln Ile Arg Pro Leu Leu Val Thr
                255                 260                 265 ttt ggc cat gat gga aaa ggg cat cct ctc cac aaa aga gaa aaa cgt     1169

```
                                                                                  1217
caa gcc aaa cac aaa cag cgg aaa cgc ctt aag tcc agc tgt aag aga
Gln Ala Lys His Lys Gln Arg Lys Arg Leu Lys Ser Ser Cys Lys Arg
        285                 290                 295

1265
cac cct ttg tac gtg gac ttc agt gac gtg ggg tgg aat gac tgg att
His Pro Leu Tyr Val Asp Phe Ser Asp Val Gly Trp Asn Asp Trp Ile
    300                 305                 310

1313
gtg gct ccc ccg ggg tat cac gcc ttt tac tgc cac gga gaa tgc cct
Val Ala Pro Pro Gly Tyr His Ala Phe Tyr Cys His Gly Glu Cys Pro
315                 320                 325                 330

1361
ttt cct ctg gct gat cat ctg aac tcc act aat cat gcc att gtt cag
Phe Pro Leu Ala Asp His Leu Asn Ser Thr Asn His Ala Ile Val Gln
                335                 340                 345

1409
acg ttg gtc aac tct gtt aac tct aag att cct aag gca tgc tgt gtc
Thr Leu Val Asn Ser Val Asn Ser Lys Ile Pro Lys Ala Cys Cys Val
            350                 355                 360

1457
ccg aca gaa ctc agt gct atc tcg atg ctg tac ctt gac gag aat gaa
Pro Thr Glu Leu Ser Ala Ile Ser Met Leu Tyr Leu Asp Glu Asn Glu
        365                 370                 375

1505
aag gtt gta tta aag aac tat cag gac atg gtt gtg gag ggt tgt ggg
Lys Val Val Leu Lys Asn Tyr Gln Asp Met Val Val Glu Gly Cys Gly
    380                 385                 390

1547
tgt cgc tag tacagcaaaa ttaaatacat aaatatatat ata
Cys Arg
395

<210> SEQ ID NO 2
<211> LENGTH: 396
<212> TYPE: PRT
<213> ORGANISM: Homo sapiens

<400> SEQUENCE: 2

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190
```

```
Asp Thr Arg Leu Val Asn Gln Asn Ala Ser Arg Trp Glu Ser Phe Asp
        195                 200                 205
Val Thr Pro Ala Val Met Arg Trp Thr Ala Gln Gly His Ala Asn His
210                 215                 220
Gly Phe Val Val Glu Val Ala His Leu Glu Glu Lys Gln Gly Val Ser
225                 230                 235                 240
Lys Arg His Val Arg Ile Ser Arg Ser Leu His Gln Asp Glu His Ser
                245                 250                 255
Trp Ser Gln Ile Arg Pro Leu Leu Val Thr Phe Gly His Asp Gly Lys
            260                 265                 270
Gly His Pro Leu His Lys Arg Glu Lys Arg Gln Ala Lys His Lys Gln
        275                 280                 285
Arg Lys Arg Leu Lys Ser Ser Cys Lys Arg His Pro Leu Tyr Val Asp
290                 295                 300
Phe Ser Asp Val Gly Trp Asn Asp Trp Ile Val Ala Pro Pro Gly Tyr
305                 310                 315                 320
His Ala Phe Tyr Cys His Gly Glu Cys Pro Phe Pro Leu Ala Asp His
                325                 330                 335
Leu Asn Ser Thr Asn His Ala Ile Val Gln Thr Leu Val Asn Ser Val
            340                 345                 350
Asn Ser Lys Ile Pro Lys Ala Cys Cys Val Pro Thr Glu Leu Ser Ala
        355                 360                 365
Ile Ser Met Leu Tyr Leu Asp Glu Asn Glu Lys Val Val Leu Lys Asn
370                 375                 380
Tyr Gln Asp Met Val Val Glu Gly Cys Gly Cys Arg
385                 390                 395

<210> SEQ ID NO 3
<211> LENGTH: 699
<212> TYPE: DNA
<213> ORGANISM: Homo sapiens
<220> FEATURE:
<221> NAME/KEY: source
<222> LOCATION: (1)..(699)
<223> OTHER INFORMATION: Homo sapiens:  Taxon:9606
<220> FEATURE:
<221> NAME/KEY: gene
<222> LOCATION: (1)..(699)
<223> OTHER INFORMATION: NOG
<220> FEATURE:
<221> NAME/KEY: sig_peptide
<222> LOCATION: (1)..(57)
<220> FEATURE:
<221> NAME/KEY: CDS
<222> LOCATION: (1)..(699)
<223> OTHER INFORMATION: Noggin, mouse, homolog of
<300> PUBLICATION INFORMATION:
<301> AUTHORS: Valenzuela,D.M., Economides,A.N., Rojas,E., Lamb,T.M.,
       Nunez,L., Jones,P., Ip,N.Y., Espinosa,R., Brannan,C.I., Gilbert,
       D.J., Copeland,N.G., Jenkins,N.A., LeBeau,M.M., Harland,R.M. and
       Yancopoulos,G.D.
<302> TITLE: Identification of mammalian noggin and its expression in
       the adult nervous system
<303> JOURNAL: J. Neurosci.
<304> VOLUME: 15
<305> ISSUE: 9
<306> PAGES: 6077-6084
<307> DATE: 1995
<308> DATABASE ACCESSION NUMBER: NM_005450
<309> DATABASE ENTRY DATE: 2000-11-01
<313> RELEVANT RESIDUES: (1)..(699)
<300> PUBLICATION INFORMATION:
<301> AUTHORS: McMahon,J.A., Takada,S., Zimmerman,L.B., Fan,C.M.,
       Harland,R.M. and McMahon,A.P.
<302> TITLE: Noggin-mediated antagonism of BMP signaling is required for
       growth and patterning of the neural tube and somite
```

```
<303> JOURNAL: Genes Dev.
<304> VOLUME: 12
<305> ISSUE: 10
<306> PAGES: 1438-1452
<307> DATE: 1998
<308> DATABASE ACCESSION NUMBER: NM_005450
<309> DATABASE ENTRY DATE: 2000-11-01
<313> RELEVANT RESIDUES: (1)..(699)
<300> PUBLICATION INFORMATION:
<301> AUTHORS: Brunet,L.J., McMahon,J.A., McMahon,A.P. and Harland,R.M.
<302> TITLE: Noggin, cartilage morphogenesis, and joint formation in the
       mammalian skeleton
<303> JOURNAL: Science
<304> VOLUME: 280
<305> ISSUE: 5368
<306> PAGES: 1455-1457
<307> DATE: 1998
<308> DATABASE ACCESSION NUMBER: NM_005450
<309> DATABASE ENTRY DATE: 2000-11-01
<313> RELEVANT RESIDUES: (1)..(699)
<300> PUBLICATION INFORMATION:
<301> AUTHORS: Smith, W.C.
<302> TITLE: TGF beta inhibitors. New and unexpected requirements in
       vertebrate development
<303> JOURNAL: Trends Genet.
<304> VOLUME: 15
<305> ISSUE: 1
<306> PAGES: 3-5
<307> DATE: 1999
<308> DATABASE ACCESSION NUMBER: NM_005450
<309> DATABASE ENTRY DATE: 2000-11-01
<313> RELEVANT RESIDUES: (1)..(699)
<300> PUBLICATION INFORMATION:
<301> AUTHORS: Gong,Y., Krakow,D., Marcelino,J., Wilkin,D., Chitayat,D.,
       Babul-Hirji,R., Hudgins,L., Cremers,C.W., Cremers,F.P.,
       Brunner,H.G., Reinker,K., Rimoin,D.L., Cohn,D.H., Goodman,F.R.,
       Reardon,W., Patton,M., Francomano,C.A. and Warman,M.L.
<302> TITLE: Heterozygous mutations in the gene encoding noggin affect
       human joint morphogenesis
<303> JOURNAL: Nat. Genet.
<304> VOLUME: 21
<305> ISSUE: 3
<306> PAGES: 302-304
<307> DATE: 1999
<308> DATABASE ACCESSION NUMBER: NM_005450
<309> DATABASE ENTRY DATE: 2000-11-01
<313> RELEVANT RESIDUES: (1)..(699)

<400> SEQUENCE: 3 atg gag cgc tgc ccc agc cta ggg gtc acc ctc tac gcc ctg gtg gtg      48
Met Glu Arg Cys Pro Ser Leu Gly Val Thr Leu Tyr Ala Leu Val Val
1               5                   10                  15 gtc ctg ggg ctg cgg gcg aca ccg gcc ggc ggc cag cac tat ctc cac      96
Val Leu Gly Leu Arg Ala Thr Pro Ala Gly Gly Gln His Tyr Leu His
            20                  25                  30 atc cgc ccg gca ccc agc gac aac ctg ccc ctg gtg gac ctc atc gaa     144
Ile Arg Pro Ala Pro Ser Asp Asn Leu Pro Leu Val Asp Leu Ile Glu
        35                  40                  45 cac cca gac cct atc ttt gac ccc aag gaa aag gat ctg aac gag acg     192
His Pro Asp Pro Ile Phe Asp Pro Lys Glu Lys Asp Leu Asn Glu Thr
50                  55                  60 ctg ctg cgc tcg ctg ctc ggg ggc cac tac gac cca ggc ttc atg gcc     240
Leu Leu Arg Ser Leu Leu Gly Gly His Tyr Asp Pro Gly Phe Met Ala
65                  70                  75                  80 acc tcg ccc ccc gag gac cgg ccc ggg ggc ggg ggt gca gct ggg         288
Thr Ser Pro Pro Glu Asp Arg Pro Gly Gly Gly Gly Ala Ala Gly
                85                  90                  95 ggc gcg gag gac ctg gcg gag ctg gac cag ctg ctg cgg cag cgg ccg     336
Gly Ala Glu Asp Leu Ala Glu Leu Asp Gln Leu Leu Arg Gln Arg Pro
            100                 105                 110 tcg ggg gcc atg ccg agc gag atc aaa ggg cta gag ttc tcc gag ggc     384
```

```
Ser Gly Ala Met Pro Ser Glu Ile Lys Gly Leu Glu Phe Ser Glu Gly
        115                 120                 125 ttg gcc cag ggc aag aag cag cgc cta agc aag aag ctg cgg agg aag    432
Leu Ala Gln Gly Lys Lys Gln Arg Leu Ser Lys Lys Leu Arg Arg Lys
    130                 135                 140 tta cag atg tgg ctg tgg tcg cag aca ttc tgc ccc gtg ctg tac gcg    480
Leu Gln Met Trp Leu Trp Ser Gln Thr Phe Cys Pro Val Leu Tyr Ala
145                 150                 155                 160 tgg aac gac ctg ggc agc cgc ttt tgg ccg cgc tac gtg aag gtg ggc    528
Trp Asn Asp Leu Gly Ser Arg Phe Trp Pro Arg Tyr Val Lys Val Gly
                165                 170                 175 agc tgc ttc agt aag cgc tcg tgc tcc gtg ccc gag ggc atg gtg tgc    576
Ser Cys Phe Ser Lys Arg Ser Cys Ser Val Pro Glu Gly Met Val Cys
            180                 185                 190 aag ccg tcc aag tcc gtg cac ctc acg gtg ctg cgg tgg cgc tgt cag    624
Lys Pro Ser Lys Ser Val His Leu Thr Val Leu Arg Trp Arg Cys Gln
        195                 200                 205 cgg cgc ggg ggc cag cgc tgc ggc tgg att ccc atc cag tac ccc atc    672
Arg Arg Gly Gly Gln Arg Cys Gly Trp Ile Pro Ile Gln Tyr Pro Ile
    210                 215                 220 att tcc gag tgc aag tgc tcg tgc tag                                699
Ile Ser Glu Cys Lys Cys Ser Cys
225                 230

<210> SEQ ID NO 4
<211> LENGTH: 232
<212> TYPE: PRT
<213> ORGANISM: Homo sapiens

<400> SEQUENCE: 4

Met Glu Arg Cys Pro Ser Leu Gly Val Thr Leu Tyr Ala Leu Val Val
1               5                   10                  15

Val Leu Gly Leu Arg Ala Thr Pro Ala Gly Gly Gln His Tyr Leu His
            20                  25                  30

Ile Arg Pro Ala Pro Ser Asp Asn Leu Pro Leu Val Asp Leu Ile Glu
        35                  40                  45

His Pro Asp Pro Ile Phe Asp Pro Lys Glu Lys Asp Leu Asn Glu Thr
    50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Ala Ala Gly
                85                  90                  95

Gly Ala Glu Asp Leu Ala Glu Leu Asp Gln Leu Leu Arg Gln Arg Pro
                100                 105                 110

Ser Gly Ala Met Pro Ser Glu Ile Lys Gly Leu Glu Phe Ser Glu Gly
        115                 120                 125

Leu Ala Gln Gly Lys Lys Gln Arg Leu Ser Lys Lys Leu Arg Arg Lys
    130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

Ser Cys Phe Ser Lys Arg Ser Cys Ser Val Pro Glu Gly Met Val Cys
            180                 185                 190

Lys Pro Ser Lys Ser Val His Leu Thr Val Leu Arg Trp Arg Cys Gln
        195                 200                 205

Arg Arg Gly Gly Gln Arg Cys Gly Trp Ile Pro Ile Gln Tyr Pro Ile
```

```
                      210                 215                 220
Ile Ser Glu Cys Lys Cys Ser Cys
225                 230

<210> SEQ ID NO 5
<211> LENGTH: 699
<212> TYPE: DNA
<213> ORGANISM: Mus musculus
<220> FEATURE:
<221> NAME/KEY: gene
<222> LOCATION: (1)..(699)
<223> OTHER INFORMATION: nog
<220> FEATURE:
<221> NAME/KEY: CDS
<222> LOCATION: (1)..(699)
<223> OTHER INFORMATION: nog

<400> SEQUENCE: 5 atg gag cgc tgc ccc agc ctg ggg gtc acc ctc tac gcc ctg gtg gtg        48
Met Glu Arg Cys Pro Ser Leu Gly Val Thr Leu Tyr Ala Leu Val Val
1               5                   10                  15 gtc ctg ggg ctg cgg gca gca cca gcc ggc ggc cag cac tat cta cac        96
Val Leu Gly Leu Arg Ala Ala Pro Ala Gly Gly Gln His Tyr Leu His
            20                  25                  30 atc cgc cca gca ccc agc gac aac ctg ccc ttg gtg gac ctc atc gaa       144
Ile Arg Pro Ala Pro Ser Asp Asn Leu Pro Leu Val Asp Leu Ile Glu
        35                  40                  45 cat cca gac cct atc ttt gac cct aag gag aag gat ctg aac gag acg       192
His Pro Asp Pro Ile Phe Asp Pro Lys Glu Lys Asp Leu Asn Glu Thr
    50                  55                  60 ctg ctg cgc tcg ctg ctc ggg ggc cac tac gac ccg ggc ttt atg gcc       240
Leu Leu Arg Ser Leu Leu Gly Gly His Tyr Asp Pro Gly Phe Met Ala
65                  70                  75                  80 act tcg ccc cca gag gac cga ccc gga ggg ggc ggg gga ccg gct gga       288
Thr Ser Pro Pro Glu Asp Arg Pro Gly Gly Gly Gly Gly Pro Ala Gly
                85                  90                  95 ggt gcc gag gac ctg gcg gag ctg gac cag ctg ctg cgg cag cgg ccg       336
Gly Ala Glu Asp Leu Ala Glu Leu Asp Gln Leu Leu Arg Gln Arg Pro
            100                 105                 110 tcg ggg gcc atg ccg agc gag atc aaa ggg ctg gag ttc tcc gag ggc       384
Ser Gly Ala Met Pro Ser Glu Ile Lys Gly Leu Glu Phe Ser Glu Gly
        115                 120                 125 ttg gcc caa ggc aag aaa cag cgc ctg agc aag aag ctg agg agg aag       432
Leu Ala Gln Gly Lys Lys Gln Arg Leu Ser Lys Lys Leu Arg Arg Lys
    130                 135                 140 tta cag atg tgg ctg tgg tca cag acc ttc tgc ccg gtg ctg tac gcg       480
Leu Gln Met Trp Leu Trp Ser Gln Thr Phe Cys Pro Val Leu Tyr Ala
145                 150                 155                 160 tgg aat gac cta ggc agc cgc ttt tgg cca cgc tac gtg aag gtg ggc       528
Trp Asn Asp Leu Gly Ser Arg Phe Trp Pro Arg Tyr Val Lys Val Gly
                165                 170                 175 agc tgc ttc agc aag cgc tcc tgc tct gtg ccc gag ggc atg gtg tgt       576
Ser Cys Phe Ser Lys Arg Ser Cys Ser Val Pro Glu Gly Met Val Cys
            180                 185                 190 aag cca tcc aag tct gtg cac ctc acg gtg ctg cgg tgg cgc tgt cag       624
Lys Pro Ser Lys Ser Val His Leu Thr Val Leu Arg Trp Arg Cys Gln
        195                 200                 205 cgg cgc ggg ggt cag cgc tgc ggc tgg att ccc atc cag tac ccc atc       672
Arg Arg Gly Gly Gln Arg Cys Gly Trp Ile Pro Ile Gln Tyr Pro Ile
    210                 215                 220 att tcc gag tgt aag tgt tcc tgc tag                                   699
Ile Ser Glu Cys Lys Cys Ser Cys
```

```
225                 230

<210> SEQ ID NO 6
<211> LENGTH: 232
<212> TYPE: PRT
<213> ORGANISM: Mus musculus

<400> SEQUENCE: 6

Met Glu Arg Cys Pro Ser Leu Gly Val Thr Leu Tyr Ala Leu Val Val
1               5                   10                  15

Val Leu Gly Leu Arg Ala Ala Pro Ala Gly Gly Gln His Tyr Leu His
            20                  25                  30

Ile Arg Pro Ala Pro Ser Asp Asn Leu Pro Leu Val Asp Leu Ile Glu
        35                  40                  45

His Pro Asp Pro Ile Phe Asp Pro Lys Glu Lys Asp Leu Asn Glu Thr
    50                  55                  60

Leu Leu Arg Ser Leu Leu Gly His Tyr Asp Pro Gly Phe Met Ala
65                  70                  75                  80

Thr Ser Pro Pro Glu Asp Arg Pro Gly Gly Gly Gly Pro Ala Gly
                85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
            115                 120                 125

Leu Ala Gln Gly Lys Lys Gln Arg Leu Ser Lys Leu Arg Arg Lys
130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                165                 170                 175

Ser Cys Phe Ser Lys Arg Ser Cys Ser Val Pro Glu Gly Met Val Cys
            180                 185                 190

Lys Pro Ser Lys Ser Val His Leu Thr Val Leu Arg Trp Arg Cys Gln
            195                 200                 205

Arg Arg Gly Gly Gln Arg Cys Gly Trp Ile Pro Ile Gln Tyr Pro Ile
    210                 215                 220

Ile Ser Glu Cys Lys Cys Ser Cys
225                 230

<210> SEQ ID NO 7
<211> LENGTH: 3547
<212> TYPE: DNA
<213> ORGANISM: Homo sapiens
<220> FEATURE:
<221> NAME/KEY: source
<222> LOCATION: (1)..(3547)
<223> OTHER INFORMATION: Taxon:9606
<220> FEATURE:
<221> NAME/KEY: gene
<222> LOCATION: (1)..(3547)
<223> OTHER INFORMATION: CHRD
<220> FEATURE:
<221> NAME/KEY: CDS
<222> LOCATION: (247)..(3114)
<223> OTHER INFORMATION: Alternatively spliced
<300> PUBLICATION INFORMATION:
<301> AUTHORS: Millet, C., Lemaire, P., Orsetti, B., Guglielmi, P., and
      Francois, V.
<302> TITLE: The human chordin gene encodes several differentially
      expressed spliced variants with distinct BMP opposing activities
<303> JOURNAL: Mech. Dev.
<304> VOLUME: 106
```

```
<305> ISSUE: 1
<306> PAGES: 85-96
<307> DATE: 2001
<308> DATABASE ACCESSION NUMBER: AF209928
<309> DATABASE ENTRY DATE: 2001-08-03
<313> RELEVANT RESIDUES: (1)..(3547)
<300> PUBLICATION INFORMATION:
<301> AUTHORS: Millet, C., and Francois, V.
<302> TITLE: Direct Submission
<303> JOURNAL: Institut de Genetique Humaine
<304> VOLUME: 1
<305> ISSUE: 1
<306> PAGES: 1-2
<307> DATE: 1999-11-30
<308> DATABASE ACCESSION NUMBER: AF209928
<309> DATABASE ENTRY DATE: 2001-08-03
<313> RELEVANT RESIDUES: (1)..(3547)

<400> SEQUENCE: 7
```

| | |
|---|---|
| cccgggtcag cgcccgcccg cccgcgctcc tcccggccgc tcctcccgcc ccgcccggcc | 60 |
| cggcgccgac tctgcggccg cccgacgagc cctcgcggc actgcccccgg ccccggcccc | 120 |
| ggccccggcc ccctcccgcc gcaccgcccc cggcccggcc ctccgccctc cgcactcccg | 180 |
| cctccctccc tccgcccgct cccgcgccct cctccctccc tcctcccag ctgtcccgtt | 240 |

```
cgcgtc atg ccg agc ctc ccg gcc ccg ccg gcc ccg ctg ctg ctc ctc       288
       Met Pro Ser Leu Pro Ala Pro Pro Ala Pro Leu Leu Leu Leu
       1               5                  10 ggg ctg ctg ctg ctc ggc tcc cgg ccg gcc cgc ggc gcc ggc ccc gag       336
Gly Leu Leu Leu Leu Gly Ser Arg Pro Ala Arg Gly Ala Gly Pro Glu
15                  20                  25                  30 ccc ccc gtg ctg ccc atc cgt tct gag aag gag ccg ctg ccc gtt cgg       384
Pro Pro Val Leu Pro Ile Arg Ser Glu Lys Glu Pro Leu Pro Val Arg
                35                  40                  45 gga gcg gca ggc tgc acc ttc ggc ggg aag gtc tat gcc ttg gac gag       432
Gly Ala Ala Gly Cys Thr Phe Gly Gly Lys Val Tyr Ala Leu Asp Glu
        50                  55                  60 acg tgg cac ccg gac cta ggg gag cca ttc ggg gtg atg cgc tgc gtg       480
Thr Trp His Pro Asp Leu Gly Glu Pro Phe Gly Val Met Arg Cys Val
65                  70                  75 ctg tgc gcc tgc gag gcg cct cag tgg ggt cgc cgt acc agg ggc cct       528
Leu Cys Ala Cys Glu Ala Pro Gln Trp Gly Arg Arg Thr Arg Gly Pro
            80                  85                  90 ggc agg gtc agc tgc aag aac atc aaa cca gag tgc cca acc ccg gcc       576
Gly Arg Val Ser Cys Lys Asn Ile Lys Pro Glu Cys Pro Thr Pro Ala
95                  100                 105                 110 tgt ggg cag ccg cgc cag ctg ccg gga cac tgc tgc cag acc tgc ccc       624
Cys Gly Gln Pro Arg Gln Leu Pro Gly His Cys Cys Gln Thr Cys Pro
                115                 120                 125 cag gag cgc agc agt tcg gag cgg cag ccg agc ggc ctg tcc ttc gag       672
Gln Glu Arg Ser Ser Ser Glu Arg Gln Pro Ser Gly Leu Ser Phe Glu
        130                 135                 140 tat ccg cgg gac ccg gag cat cgc agt tat agc gac cgc ggg gag cca       720
Tyr Pro Arg Asp Pro Glu His Arg Ser Tyr Ser Asp Arg Gly Glu Pro
145                 150                 155 ggc gct gag gag cgg gcc cgt ggt gac ggc cac acg gac ttc gtg gcg       768
Gly Ala Glu Glu Arg Ala Arg Gly Asp Gly His Thr Asp Phe Val Ala
            160                 165                 170 ctg ctg aca ggg ccg agg tcg cag gcg gtg gca cga gcc cga gtc tcg       816
Leu Leu Thr Gly Pro Arg Ser Gln Ala Val Ala Arg Ala Arg Val Ser
175                 180                 185                 190 ctg ctg cgc tct agc ctc cgc ttc tct atc tcc tac agg cgg ctg gac       864
Leu Leu Arg Ser Ser Leu Arg Phe Ser Ile Ser Tyr Arg Arg Leu Asp
                195                 200                 205
```

```
cgc cct acc agg atc cgc ttc tca gac tcc aat ggc agt gtc ctg ttt       912
Arg Pro Thr Arg Ile Arg Phe Ser Asp Ser Asn Gly Ser Val Leu Phe
        210                 215                 220 gag cac cct gca gcc ccc acc caa gat ggc ctg gtc tgt ggg gtg tgg       960
Glu His Pro Ala Ala Pro Thr Gln Asp Gly Leu Val Cys Gly Val Trp
225                 230                 235 cgg gca gtg cct cgg ttg tct ctg cgg ctc ctt agg gca gaa cag ctg      1008
Arg Ala Val Pro Arg Leu Ser Leu Arg Leu Leu Arg Ala Glu Gln Leu
        240                 245                 250 cat gtg gca ctt gtg aca ctc act cac cct tca ggg gag gtc tgg ggg      1056
His Val Ala Leu Val Thr Leu Thr His Pro Ser Gly Glu Val Trp Gly
255                 260                 265                 270 cct ctc atc cgg cac cgg gcc ctg gct gca gag acc ttc agt gcc atc      1104
Pro Leu Ile Arg His Arg Ala Leu Ala Ala Glu Thr Phe Ser Ala Ile
            275                 280                 285 ctg act cta gaa ggc ccc cca cag cag ggc gta ggg ggc atc acc ctg      1152
Leu Thr Leu Glu Gly Pro Pro Gln Gln Gly Val Gly Gly Ile Thr Leu
        290                 295                 300 ctc act ctc agt gac aca gag gac tcc ttg cat ttt ttg ctg ctc ttc      1200
Leu Thr Leu Ser Asp Thr Glu Asp Ser Leu His Phe Leu Leu Leu Phe
        305                 310                 315 cga ggg ctg ctg gaa ccc agg agt ggg gga cta acc cag gtt ccc ttg      1248
Arg Gly Leu Leu Glu Pro Arg Ser Gly Gly Leu Thr Gln Val Pro Leu
320                 325                 330 agg ctc cag att cta cac cag ggg cag cta ctg cga gaa ctt cag gcc      1296
Arg Leu Gln Ile Leu His Gln Gly Gln Leu Leu Arg Glu Leu Gln Ala
335                 340                 345                 350 aat gtc tca gcc cag gaa cca ggc ttt gct gag gtg ctg ccc aac ctg      1344
Asn Val Ser Ala Gln Glu Pro Gly Phe Ala Glu Val Leu Pro Asn Leu
            355                 360                 365 aca gtc cag gag atg gac tgg ctg gtg ctg ggg gag ctg cag atg gcc      1392
Thr Val Gln Glu Met Asp Trp Leu Val Leu Gly Glu Leu Gln Met Ala
        370                 375                 380 ctg gag tgg gca ggc agg cca ggg ctg cgc atc agt gga cac att gct      1440
Leu Glu Trp Ala Gly Arg Pro Gly Leu Arg Ile Ser Gly His Ile Ala
385                 390                 395 gcc agg aag agc tgc gac gtc ctg caa agt gtc ctt tgt ggg gct gat      1488
Ala Arg Lys Ser Cys Asp Val Leu Gln Ser Val Leu Cys Gly Ala Asp
400                 405                 410 gcc ctg atc cca gtc cag acg ggt gct gcc ggc tca gcc agc ctc acg      1536
Ala Leu Ile Pro Val Gln Thr Gly Ala Ala Gly Ser Ala Ser Leu Thr
415                 420                 425                 430 ctg cta gga aat ggc tcc ctg atc tat cag gtg caa gtg gta ggg aca      1584
Leu Leu Gly Asn Gly Ser Leu Ile Tyr Gln Val Gln Val Val Gly Thr
            435                 440                 445 agc agt gag gtg gtg gcc atg aca ctg gag acc aag cct cag cgg agg      1632
Ser Ser Glu Val Val Ala Met Thr Leu Glu Thr Lys Pro Gln Arg Arg
        450                 455                 460 gat cag cgc act gtc ctg tgc cac atg gct gga ctc cag cca gga gga      1680
Asp Gln Arg Thr Val Leu Cys His Met Ala Gly Leu Gln Pro Gly Gly
465                 470                 475 cac acg gcc gtg ggt atc tgc cct ggg ctg ggt gcc cga ggg gct cat      1728
His Thr Ala Val Gly Ile Cys Pro Gly Leu Gly Ala Arg Gly Ala His
480                 485                 490 atg ctg ctg cag aat gag ctc ttc ctg aat gtg ggc acc aag gac ttc      1776
Met Leu Leu Gln Asn Glu Leu Phe Leu Asn Val Gly Thr Lys Asp Phe
495                 500                 505                 510 cca gac gga gag ctt cgg ggg cac gtg gct gcc ctg ccc tac tgt ggg      1824
Pro Asp Gly Glu Leu Arg Gly His Val Ala Ala Leu Pro Tyr Cys Gly
```

-continued

| | | |
|---|---|---|
| 515 | 520 | 525 |

```
cat agc gcc cgc cat gac acg ctg ccc gtg ccc cta gca gga gcc ctg    1872
His Ser Ala Arg His Asp Thr Leu Pro Val Pro Leu Ala Gly Ala Leu
            530                 535                 540 gtg cta ccc cct gtg aag agc caa gca gca ggg cac gcc tgg ctt tcc    1920
Val Leu Pro Pro Val Lys Ser Gln Ala Ala Gly His Ala Trp Leu Ser
        545                 550                 555 ttg gat acc cac tgt cac ctg cac tat gaa gtg ctg ctg gct ggg ctt    1968
Leu Asp Thr His Cys His Leu His Tyr Glu Val Leu Leu Ala Gly Leu
    560                 565                 570 ggt ggc tca gaa caa ggc act gtc act gcc cac ctc ctt ggg cct cct    2016
Gly Gly Ser Glu Gln Gly Thr Val Thr Ala His Leu Leu Gly Pro Pro
575                 580                 585                 590 gga acg cca ggg cct cgg cgg ctg ctg aag gga ttc tat ggc tca gag    2064
Gly Thr Pro Gly Pro Arg Arg Leu Leu Lys Gly Phe Tyr Gly Ser Glu
                595                 600                 605 gcc cag ggt gtg gtg aag gac ctg gag ccg gaa ctg ctg cgg cac ctg    2112
Ala Gln Gly Val Val Lys Asp Leu Glu Pro Glu Leu Leu Arg His Leu
            610                 615                 620 gca aaa ggc atg gcc tcc ctg ctg atc acc acc aag ggt agc ccc aga    2160
Ala Lys Gly Met Ala Ser Leu Leu Ile Thr Thr Lys Gly Ser Pro Arg
        625                 630                 635 ggg gag ctc cga ggg cag gtg cac ata gcc aac caa tgt gag gtt ggc    2208
Gly Glu Leu Arg Gly Gln Val His Ile Ala Asn Gln Cys Glu Val Gly
    640                 645                 650 gga ctg cgc ctg gag gcg gcc ggg gcc gag ggg gtg cgg gcg ctg ggg    2256
Gly Leu Arg Leu Glu Ala Ala Gly Ala Glu Gly Val Arg Ala Leu Gly
655                 660                 665                 670 gct ccg gat aca gcc tct gct gcg ccg cct gtg gtg cct ggt ctc ccg    2304
Ala Pro Asp Thr Ala Ser Ala Ala Pro Pro Val Val Pro Gly Leu Pro
                675                 680                 685 gcc cta gcg ccc gcc aaa cct ggt ggt cct ggg cgg ccc cga gac ccc    2352
Ala Leu Ala Pro Ala Lys Pro Gly Gly Pro Gly Arg Pro Arg Asp Pro
            690                 695                 700 aac aca tgc ttc ttc gag ggg cag cag cgc ccc cac ggg gct cgc tgg    2400
Asn Thr Cys Phe Phe Glu Gly Gln Gln Arg Pro His Gly Ala Arg Trp
        705                 710                 715 gcg ccc aac tac gac ccg ctc tgc tca ctc tgc acc tgc cag aga cga    2448
Ala Pro Asn Tyr Asp Pro Leu Cys Ser Leu Cys Thr Cys Gln Arg Arg
    720                 725                 730 acg gtg atc tgt gac ccg gtg gtg tgc cca ccg ccc agc tgc cca cac    2496
Thr Val Ile Cys Asp Pro Val Val Cys Pro Pro Pro Ser Cys Pro His
735                 740                 745                 750 ccg gtg cag gct ccc gac cag tgc tgc cct gtt tgc cct gag aaa caa    2544
Pro Val Gln Ala Pro Asp Gln Cys Cys Pro Val Cys Pro Glu Lys Gln
                755                 760                 765 gat gtc aga gac ttg cca ggg ctg cca agg agc cgg gac cca gga gag    2592
Asp Val Arg Asp Leu Pro Gly Leu Pro Arg Ser Arg Asp Pro Gly Glu
            770                 775                 780 ggc tgc tat ttt gat ggt gac cgg agc tgg cgg gca gcg ggt acg cgg    2640
Gly Cys Tyr Phe Asp Gly Asp Arg Ser Trp Arg Ala Ala Gly Thr Arg
        785                 790                 795 tgg cac ccc gtt gtg ccc ccc ttt ggc tta att aag tgt gct gtc tgc    2688
Trp His Pro Val Val Pro Pro Phe Gly Leu Ile Lys Cys Ala Val Cys
    800                 805                 810 acc tgc aag ggg ggc act gga gag gtg cac tgt gag aag gtg cag tgt    2736
Thr Cys Lys Gly Gly Thr Gly Glu Val His Cys Glu Lys Val Gln Cys
815                 820                 825                 830 ccc cgg ctg gcc tgt gcc cag cct gtg cgt gtc aac ccc acc gac tgc    2784
```

```
Pro Arg Leu Ala Cys Ala Gln Pro Val Arg Val Asn Pro Thr Asp Cys
                835                 840                 845 tgc aaa cag tgt cca gtg ggg tcg ggg gcc cac ccc cag ctg ggg gac      2832
Cys Lys Gln Cys Pro Val Gly Ser Gly Ala His Pro Gln Leu Gly Asp
            850                 855                 860 ccc atg cag gct gat ggg ccc cgg ggc tgc cgt ttt gct ggg cag tgg      2880
Pro Met Gln Ala Asp Gly Pro Arg Gly Cys Arg Phe Ala Gly Gln Trp
        865                 870                 875 ttc cca gag agt cag agc tgg cac ccc tca gtg ccc cct ttt gga gag      2928
Phe Pro Glu Ser Gln Ser Trp His Pro Ser Val Pro Pro Phe Gly Glu
    880                 885                 890 atg agc tgt atc acc tgc aga tgt ggg gca ggg gtg cct cac tgt gag      2976
Met Ser Cys Ile Thr Cys Arg Cys Gly Ala Gly Val Pro His Cys Glu
895                 900                 905                 910 cgg gat gac tgt tca ctg cca ctg tcc tgt ggc tcg ggg aag gag agt      3024
Arg Asp Asp Cys Ser Leu Pro Leu Ser Cys Gly Ser Gly Lys Glu Ser
                915                 920                 925 cga tgc tgt tcc cgc tgc acg gcc cac cgg cgg cca gcc cca gag acc      3072
Arg Cys Cys Ser Arg Cys Thr Ala His Arg Arg Pro Ala Pro Glu Thr
            930                 935                 940 aga act gat cca gag ctg gag aaa gaa gcc gaa ggc tct tag              3114
Arg Thr Asp Pro Glu Leu Glu Lys Glu Ala Glu Gly Ser
        945                 950                 955 ggagcagcca gagggccaag tgaccaagag gatggggcct gagctgggga aggggtggca    3174
tcgaggacct tcttgcattc tcctgtggga agcccagtgc ctttgctcct ctgtcctgcc    3234
tctactccca cccccactac ctctgggaac cacagctcca caaggggag aggcagctgg     3294 gccagaccga ggtcacagcc actccaagtc ctgccctgcc accctcggcc tctgtcctgg    3354
aagccccacc ccttttcctcc tgtacataat gtcactggct tgttgggatt tttaatttat   3414
cttcactcag caccaagggc ccccgacact ccactcctgc tgcccctgag ctgagcagag    3474
tcattattgg agagttttgt atttattaaa acatttcttt ttcagtcaaa aaaaaaaaa     3534 aaaaaaaaaa aaa                                                       3547

<210> SEQ ID NO 8
<211> LENGTH: 955
<212> TYPE: PRT
<213> ORGANISM: Homo sapiens

<400> SEQUENCE: 8

Met Pro Ser Leu Pro Ala Pro Ala Pro Leu Leu Leu Gly Leu
1               5                   10                  15

Leu Leu Leu Gly Ser Arg Pro Ala Arg Gly Ala Gly Pro Glu Pro Pro
                20                  25                  30

Val Leu Pro Ile Arg Ser Glu Lys Glu Pro Leu Pro Val Arg Gly Ala
            35                  40                  45

Ala Gly Cys Thr Phe Gly Gly Lys Val Tyr Ala Leu Asp Glu Thr Trp
        50                  55                  60

His Pro Asp Leu Gly Glu Pro Phe Gly Val Met Arg Cys Val Leu Cys
65                  70                  75                  80

Ala Cys Glu Ala Pro Gln Trp Gly Arg Arg Thr Arg Gly Pro Gly Arg
                85                  90                  95

Val Ser Cys Lys Asn Ile Lys Pro Glu Cys Pro Thr Pro Ala Cys Gly
            100                 105                 110

Gln Pro Arg Gln Leu Pro Gly His Cys Cys Gln Thr Cys Pro Gln Glu
        115                 120                 125
```

-continued

```
Arg Ser Ser Ser Glu Arg Gln Pro Ser Gly Leu Ser Phe Glu Tyr Pro
    130                 135                 140

Arg Asp Pro Glu His Arg Ser Tyr Ser Asp Arg Gly Glu Pro Gly Ala
145                 150                 155                 160

Glu Glu Arg Ala Arg Gly Asp Gly His Thr Asp Phe Val Ala Leu Leu
                165                 170                 175

Thr Gly Pro Arg Ser Gln Ala Val Ala Arg Ala Arg Val Ser Leu Leu
                180                 185                 190

Arg Ser Ser Leu Arg Phe Ser Ile Ser Tyr Arg Arg Leu Asp Arg Pro
    195                 200                 205

Thr Arg Ile Arg Phe Ser Asp Ser Asn Gly Ser Val Leu Phe Glu His
    210                 215                 220

Pro Ala Ala Pro Thr Gln Asp Gly Leu Val Cys Gly Val Trp Arg Ala
225                 230                 235                 240

Val Pro Arg Leu Ser Leu Arg Leu Leu Arg Ala Glu Gln Leu His Val
                245                 250                 255

Ala Leu Val Thr Leu Thr His Pro Ser Gly Glu Val Trp Gly Pro Leu
                260                 265                 270

Ile Arg His Arg Ala Leu Ala Ala Glu Thr Phe Ser Ala Ile Leu Thr
    275                 280                 285

Leu Glu Gly Pro Pro Gln Gln Gly Val Gly Gly Ile Thr Leu Leu Thr
    290                 295                 300

Leu Ser Asp Thr Glu Asp Ser Leu His Phe Leu Leu Phe Arg Gly
305                 310                 315                 320

Leu Leu Glu Pro Arg Ser Gly Gly Leu Thr Gln Val Pro Leu Arg Leu
                325                 330                 335

Gln Ile Leu His Gln Gly Gln Leu Leu Arg Glu Leu Gln Ala Asn Val
    340                 345                 350

Ser Ala Gln Glu Pro Gly Phe Ala Glu Val Leu Pro Asn Leu Thr Val
    355                 360                 365

Gln Glu Met Asp Trp Leu Val Leu Gly Glu Leu Gln Met Ala Leu Glu
370                 375                 380

Trp Ala Gly Arg Pro Gly Leu Arg Ile Ser Gly His Ile Ala Ala Arg
385                 390                 395                 400

Lys Ser Cys Asp Val Leu Gln Ser Val Leu Cys Gly Ala Asp Ala Leu
                405                 410                 415

Ile Pro Val Gln Thr Gly Ala Ala Gly Ser Ala Ser Leu Thr Leu Leu
    420                 425                 430

Gly Asn Gly Ser Leu Ile Tyr Gln Val Gln Val Val Gly Thr Ser Ser
    435                 440                 445

Glu Val Val Ala Met Thr Leu Glu Thr Lys Pro Gln Arg Arg Asp Gln
    450                 455                 460

Arg Thr Val Leu Cys His Met Ala Gly Leu Gln Pro Gly Gly His Thr
465                 470                 475                 480

Ala Val Gly Ile Cys Pro Gly Leu Gly Ala Arg Gly Ala His Met Leu
                485                 490                 495

Leu Gln Asn Glu Leu Phe Leu Asn Val Gly Thr Lys Asp Phe Pro Asp
                500                 505                 510

Gly Glu Leu Arg Gly His Val Ala Ala Leu Pro Tyr Cys Gly His Ser
                515                 520                 525

Ala Arg His Asp Thr Leu Pro Val Pro Leu Ala Gly Ala Leu Val Leu
    530                 535                 540

Pro Pro Val Lys Ser Gln Ala Ala Gly His Ala Trp Leu Ser Leu Asp
```

```
                545                 550                 555                 560
Thr His Cys His Leu His Tyr Glu Val Leu Leu Ala Gly Leu Gly Gly
                    565                 570                 575
Ser Glu Gln Gly Thr Val Thr Ala His Leu Leu Gly Pro Pro Gly Thr
                580                 585                 590
Pro Gly Pro Arg Arg Leu Leu Lys Gly Phe Tyr Gly Ser Glu Ala Gln
            595                 600                 605
Gly Val Val Lys Asp Leu Glu Pro Glu Leu Leu Arg His Leu Ala Lys
        610                 615                 620
Gly Met Ala Ser Leu Leu Ile Thr Thr Lys Gly Ser Pro Arg Gly Glu
625                 630                 635                 640
Leu Arg Gly Gln Val His Ile Ala Asn Gln Cys Glu Val Gly Gly Leu
                    645                 650                 655
Arg Leu Glu Ala Ala Gly Ala Glu Gly Val Arg Ala Leu Gly Ala Pro
                660                 665                 670
Asp Thr Ala Ser Ala Ala Pro Val Val Pro Gly Leu Pro Ala Leu
            675                 680                 685
Ala Pro Ala Lys Pro Gly Gly Pro Gly Arg Pro Arg Asp Pro Asn Thr
        690                 695                 700
Cys Phe Phe Glu Gly Gln Gln Arg Pro His Gly Ala Arg Trp Ala Pro
705                 710                 715                 720
Asn Tyr Asp Pro Leu Cys Ser Leu Cys Thr Cys Gln Arg Arg Thr Val
                    725                 730                 735
Ile Cys Asp Pro Val Val Cys Pro Pro Pro Ser Cys Pro His Pro Val
                740                 745                 750
Gln Ala Pro Asp Gln Cys Cys Pro Val Cys Pro Glu Lys Gln Asp Val
            755                 760                 765
Arg Asp Leu Pro Gly Leu Pro Arg Ser Arg Asp Pro Gly Glu Gly Cys
        770                 775                 780
Tyr Phe Asp Gly Asp Arg Ser Trp Arg Ala Ala Gly Thr Arg Trp His
785                 790                 795                 800
Pro Val Val Pro Pro Phe Gly Leu Ile Lys Cys Ala Val Cys Thr Cys
                    805                 810                 815
Lys Gly Gly Thr Gly Glu Val His Cys Glu Lys Val Gln Cys Pro Arg
                820                 825                 830
Leu Ala Cys Ala Gln Pro Val Arg Val Asn Pro Thr Asp Cys Cys Lys
            835                 840                 845
Gln Cys Pro Val Gly Ser Gly Ala His Pro Gln Leu Gly Asp Pro Met
        850                 855                 860
Gln Ala Asp Gly Pro Arg Gly Cys Arg Phe Ala Gly Gln Trp Phe Pro
865                 870                 875                 880
Glu Ser Gln Ser Trp His Pro Ser Val Pro Pro Phe Gly Glu Met Ser
                    885                 890                 895
Cys Ile Thr Cys Arg Cys Gly Ala Gly Val Pro His Cys Glu Arg Asp
                900                 905                 910
Asp Cys Ser Leu Pro Leu Ser Cys Gly Ser Gly Lys Glu Ser Arg Cys
            915                 920                 925
Cys Ser Arg Cys Thr Ala His Arg Arg Pro Ala Pro Glu Thr Arg Thr
        930                 935                 940
Asp Pro Glu Leu Glu Lys Glu Ala Glu Gly Ser
945                 950                 955

<210> SEQ ID NO 9
```

```
<211> LENGTH: 3299
<212> TYPE: DNA
<213> ORGANISM: Homo sapiens
<220> FEATURE:
<221> NAME/KEY: source
<222> LOCATION: (1)..(3299)
<223> OTHER INFORMATION: small intestine
<220> FEATURE:
<221> NAME/KEY: gene
<222> LOCATION: (1)..(3299)
<223> OTHER INFORMATION: DRM
<220> FEATURE:
<221> NAME/KEY: CDS
<222> LOCATION: (130)..(684)
<223> OTHER INFORMATION: DRM
<300> PUBLICATION INFORMATION:
<301> AUTHORS: Topol, L.Z., Modi, W.S., Koochekpour, S., and Blair, D.G.
<302> TITLE: DRM/Gremlin (CKTSF1B1) maps to human chromosome 15 adn is
       highly expressed in adult and fetal brain
<303> JOURNAL: Cytogenet. Cell Genet.
<304> VOLUME: 89
<305> ISSUE: 1
<306> PAGES: 79-84
<307> DATE: 2000
<308> DATABASE ACCESSION NUMBER: AF154054
<309> DATABASE ENTRY DATE: 2000-10-18
<313> RELEVANT RESIDUES: (1)..(3299)
<300> PUBLICATION INFORMATION:
<301> AUTHORS: Topol, L.Z., Marx, M., Calothy, G., and Blair, D.G.
<302> TITLE: Direct Submission
<303> JOURNAL: Oncogene Mechanisms Section, Basic Research Laboratory,
       NIH/NCI
<304> VOLUME: 1
<305> ISSUE: 1
<306> PAGES: 1
<307> DATE: 1999-05-25
<308> DATABASE ACCESSION NUMBER: AF154054
<309> DATABASE ENTRY DATE: 2000-10-18
<313> RELEVANT RESIDUES: (1)..(3299)

<400> SEQUENCE: 9
ataataatta ggccaagcgt tgaatagtac gggggggggg ggggggcgag ccccggcggc      60
tctggccgcg gccgcactca gcgccacgcg tcgaaagcgc aggccccgag gacccgccgc     120 actgacagt atg agc cgc aca gcc tac acg gtg gga gcc ctg ctt ctc ctc   171
          Met Ser Arg Thr Ala Tyr Thr Val Gly Ala Leu Leu Leu Leu
          1               5                  10 ttg ggg acc ctg ctg ccg gct gct gaa ggg aaa aag aaa ggg tcc caa     219
Leu Gly Thr Leu Leu Pro Ala Ala Glu Gly Lys Lys Lys Gly Ser Gln
15                  20                  25                  30 ggt gcc atc ccc ccg cca gac aag gcc cag cac aat gac tca gag cag     267
Gly Ala Ile Pro Pro Pro Asp Lys Ala Gln His Asn Asp Ser Glu Gln
                35                  40                  45 act cag tcg ccc cag cag cct ggc tcc agg aac cgg ggg cgg ggc caa     315
Thr Gln Ser Pro Gln Gln Pro Gly Ser Arg Asn Arg Gly Arg Gly Gln
            50                  55                  60 ggg cgg ggc act gcc atg ccc ggg gag gag gtg ctg gag tcc agc caa     363
Gly Arg Gly Thr Ala Met Pro Gly Glu Glu Val Leu Glu Ser Ser Gln
65                  70                  75 gag gcc ctg cat gtg acg gag cgc aaa tac ctg aag cga gac tgg tgc     411
Glu Ala Leu His Val Thr Glu Arg Lys Tyr Leu Lys Arg Asp Trp Cys
        80                  85                  90 aaa acc cag ccg ctt aag cag acc atc cac gag gaa ggc tgc aac agt     459
Lys Thr Gln Pro Leu Lys Gln Thr Ile His Glu Glu Gly Cys Asn Ser
95                  100                 105                 110 cgc acc atc atc aac cgc ttc tgt tac ggc cag tgc aac tct ttc tac     507
Arg Thr Ile Ile Asn Arg Phe Cys Tyr Gly Gln Cys Asn Ser Phe Tyr
                115                 120                 125 atc ccc agg cac atc cgg aag gag gaa ggt tcc ttt cag tcc tgc tcc     555
```

```
Ile Pro Arg His Ile Arg Lys Glu Glu Gly Ser Phe Gln Ser Cys Ser
            130                 135                 140 ttc tgc aag ccc aag aaa ttc act acc atg atg gtc aca ctc aac tgc    603
Phe Cys Lys Pro Lys Lys Phe Thr Thr Met Met Val Thr Leu Asn Cys
            145                 150                 155 cct gaa cta cag cca cct acc aag aag aag aga gtc aca cgt gtg aag    651
Pro Glu Leu Gln Pro Pro Thr Lys Lys Lys Arg Val Thr Arg Val Lys
            160                 165                 170 cag tgt cgt tgc ata tcc atc gat ttg gat taa gccaaatcca ggtgcaccca   704
Gln Cys Arg Cys Ile Ser Ile Asp Leu Asp
175                 180 gcatgtccta ggaatgcaga cccaggaagt cccagaccta aacaaccag attcttactt    764
ggcttaaacc tagaggccag aagaacccc agctgcctcc tggcaggagc ctgcttgtgc    824
gtagttcgtg tgcatgagtg tggatgggtg cctgtgggtg ttttagaca ccagagaaaa    884
cacagtctct gctagagagc acttcctatt ttgtaaacct atctgcttta atggggatgt    944
accagaaacc cacctcaccc cggctcacat ctaaaggggc ggggccgtgg tctggttctg   1004
actttgtgtt tttgtgccct cctggggacc agaatctcct ttcggaatga atgttcatgg   1064
aagaggctcc tctgagggca agagacctgt tttagtgctg cattcgacat ggaaaagtcc   1124
ttttaacctg tgcttgcatc ctcctttcct cctcctcctc acaatccatc tcttcttaag   1184
ttgacagtga ctatgtcagt ctaatctctt gtttgccagg gttcctaaat taattcactt   1244
aaccatgatg caaatgtttt tcatttggtg aagacctcca gactctggga gaggctggtg   1304
tgggcaagga caagcaggat agtggagtga aaagggagg gtggagggtg aggccaaatc   1364
aggtccagca aaagtcagta gggacattgc agaagcttga aaggccaata ccagaacaca   1424
ggctgatgct tctgagaaag tcttttccta gtatttaaca aaacccaagt gaacagagga   1484
gaaatgagat tgccagaaag tgattaactt tggccgttgc aatctgctca aacctaacac   1544
caaactgaaa acataaatac tgaccactcc tatgttcgga cccaagcaag ttagctaaac   1604
caaaccaact cctctgcttt gtccctcagg tggaaaagag aggtagttta gaactctctg   1664
catagggtg ggaattaatc aaaaacctca gaggctgaaa ttcctaatac cttttccttta   1724
tcgtggttat agtcagctca tttccattcc actatttccc ataatgcttc tgagagccac   1784
taacttgatt gataaagatc ctgcctctgc tgagtgtacc tgacagtagt ctaagatgag   1844
agagtttagg gactactctg ttttaacaag aaatattttg ggggtctttt tgttttaact   1904
attgtcagga gattgggcta agagaagac gacgagagta aggaaataaa gggaattgcc   1964
tctggctaga gagtagttag gtgttaatac ctggtagaga tgtaagggat atgacctccc   2024
tttctttatg tgctcacttg aggatctgag gggaccctgt taggagagca tagcatcatg   2084
atgtattagc tgttcatctg ctactggttg gatggacata actattgtaa ctattcagta   2144
tttactggta ggcactgtcc tctgattaaa cttggcctac tggcaatggc tacttaggat   2204
tgatctaagg gccaaagtgc agggtgggtg aactttattg tactttggat ttggttaacc   2264
tgttttcctc aagcctgagg ttttatatac aaactccctg aatactcttt ttgccttgtt   2324
acttctcagc ctcctagcca agtcctatgt aatatggaaa acaaacactg cagacttgag   2384
attcagttgc cgatcaaggc tctggcattc agagaaccct tgcaactcga aagctgttt    2444
ttgatttcgt ttttgttttg aaccggtgct ctcccatcta caactaaca aggaccattt    2504
ccaggcggga gatatttaa acacccaaaa tgtgggtct gatttccaaa cttttaaact    2564
cactactgat gattctcacg ctaggcgaat ttgtccaaac acatagtgtg tgtgttttgt   2624
```

| | |
|---|---|
| atacactgta tgaccccacc ccaaatcttt gtattgtcca cattctccaa caataaagca | 2684 |
| cagagtggat ttaattaagc acacaaatgc taaggcagaa ttttgagggt gggagagaag | 2744 |
| aaaagggaaa gaagctgaaa atgtaaaacc acaccaggga ggaaaaatga cattcagaac | 2804 |
| caccaaacac tgaatttctc ttgttgtttt aactctccca caagaatgca atttcgttaa | 2864 |
| tggagatgac ttaagttggc agcagtaatc ttcttttagg agcttgtacc acagtcttgc | 2924 |
| acataagtgc agatttgccc caagtaaaga gaatttcctc aacactaact tcacggggat | 2984 |
| aatcaccacg taactaccct taaagcatat cactagccaa agagggaat atctgttctt | 3044 |
| cttactgtgc ctatattaag actagtacaa atgtggtgtg tcttccaact ttcattgaaa | 3104 |
| atgccatatc tataccatat tttattcgag tcactgatga tgtaatgata tatttttca | 3164 |
| ttattatagt agaatatttt tatggcaaga gatttgtggt cttgatcata cctattaaaa | 3224 |
| taatgccaaa caccaaatat gaatttatg atgtacactt tgtgcttggc attaaaagaa | 3284 |
| aaaaacacac acgcc | 3299 |

<210> SEQ ID NO 10
<211> LENGTH: 184
<212> TYPE: PRT
<213> ORGANISM: Homo sapiens

<400> SEQUENCE: 10

Met Ser Arg Thr Ala Tyr Thr Val Gly Ala Leu Leu Leu Leu Gly
1               5                   10                  15

Thr Leu Leu Pro Ala Ala Glu Gly Lys Lys Gly Ser Gln Gly Ala
            20                  25                  30

Ile Pro Pro Asp Lys Ala Gln His Asn Asp Ser Glu Gln Thr Gln
        35                  40                  45

Ser Pro Gln Gln Pro Gly Ser Arg Asn Arg Gly Arg Gly Gln Gly Arg
    50                  55                  60

Gly Thr Ala Met Pro Gly Glu Glu Val Leu Glu Ser Ser Gln Glu Ala
65                  70                  75                  80

Leu His Val Thr Glu Arg Lys Tyr Leu Lys Arg Asp Trp Cys Lys Thr
                85                  90                  95

Gln Pro Leu Lys Gln Thr Ile His Glu Glu Gly Cys Asn Ser Arg Thr
            100                 105                 110

Ile Ile Asn Arg Phe Cys Tyr Gly Gln Cys Asn Ser Phe Tyr Ile Pro
        115                 120                 125

Arg His Ile Arg Lys Glu Glu Gly Ser Phe Gln Ser Cys Ser Phe Cys
    130                 135                 140

Lys Pro Lys Lys Phe Thr Thr Met Met Val Thr Leu Asn Cys Pro Glu
145                 150                 155                 160

Leu Gln Pro Pro Thr Lys Lys Arg Val Thr Arg Val Lys Gln Cys
                165                 170                 175

Arg Cys Ile Ser Ile Asp Leu Asp
            180

<210> SEQ ID NO 11
<211> LENGTH: 804
<212> TYPE: DNA
<213> ORGANISM: Homo sapiens
<220> FEATURE:
<221> NAME/KEY: source
<222> LOCATION: (1)..(804)
<220> FEATURE:
<221> NAME/KEY: gene
<222> LOCATION: (1)..(804)

```
<223> OTHER INFORMATION: CER1
<220> FEATURE:
<221> NAME/KEY: CDS
<222> LOCATION: (1)..(804)
<223> OTHER INFORMATION: cerberus-related 1; cerberus 1 (Xenopus
      laevis) homolog (cysteine knot superfamily)
<220> FEATURE:
<221> NAME/KEY: misc_feature
<222> LOCATION: (361)..(741)
<223> OTHER INFORMATION: DAN domain
<220> FEATURE:
<221> NAME/KEY: misc_feature
<222> LOCATION: (484)..(723)
<223> OTHER INFORMATION: Cysteine knot region
<220> FEATURE:
<221> NAME/KEY: misc_feature
<222> LOCATION: (490)..(723)
<223> OTHER INFORMATION: C-terminal cysteine knot-like domain
<300> PUBLICATION INFORMATION:
<301> AUTHORS: Lah, M., Brodnicki, T., Maccarone, P., Nash, A.,
      Stanley, E., and Harvey, R.P.
<302> TITLE: Human cerberus related gene CER1 maps to chromosome 9
<303> JOURNAL: Genomics
<304> VOLUME: 55
<305> ISSUE: 3
<306> PAGES: 364-366
<307> DATE: 1999
<308> DATABASE ACCESSION NUMBER: NM_005454
<309> DATABASE ENTRY DATE: 2001-12-20
<313> RELEVANT RESIDUES: (1)..(804)

<400> SEQUENCE: 11 atg cat ctc ctc tta ttt cag ctg ctg gta ctc ctg cct cta gga aag        48
Met His Leu Leu Leu Phe Gln Leu Leu Val Leu Leu Pro Leu Gly Lys
1               5                   10                  15 acc aca cgg cac cag gat ggc cgc cag aat cag agt tct ctt tcc ccc        96
Thr Thr Arg His Gln Asp Gly Arg Gln Asn Gln Ser Ser Leu Ser Pro
            20                  25                  30 gta ctc ctg cca agg aat caa aga gag ctt ccc aca ggc aac cat gag       144
Val Leu Leu Pro Arg Asn Gln Arg Glu Leu Pro Thr Gly Asn His Glu
        35                  40                  45 gaa gct gag gag aag cca gat ctg ttt gtc gca gtg cca cac ctt gta       192
Glu Ala Glu Glu Lys Pro Asp Leu Phe Val Ala Val Pro His Leu Val
50                  55                  60 gcc acc agc cct gca ggg gaa ggc cag agg cag aga gag aag atg ctg       240
Ala Thr Ser Pro Ala Gly Glu Gly Gln Arg Gln Arg Glu Lys Met Leu
65                  70                  75                  80 tcc aga ttt ggc agg ttc tgg aag aag cct gag aga gaa atg cat cca       288
Ser Arg Phe Gly Arg Phe Trp Lys Lys Pro Glu Arg Glu Met His Pro
                85                  90                  95 tcc agg gac tca gat agt gag ccc ttc cca cct ggg acc cag tcc ctc       336
Ser Arg Asp Ser Asp Ser Glu Pro Phe Pro Pro Gly Thr Gln Ser Leu
            100                 105                 110 atc cag ccg ata gat gga atg aaa atg gag aaa tct cct ctt cgg gaa       384
Ile Gln Pro Ile Asp Gly Met Lys Met Glu Lys Ser Pro Leu Arg Glu
        115                 120                 125 gaa gcc aag aaa ttc tgg cac cac ttc atg ttc aga aaa act ccg gct       432
Glu Ala Lys Lys Phe Trp His His Phe Met Phe Arg Lys Thr Pro Ala
130                 135                 140 tct cag ggg gtc atc ttg ccc atc aaa agc cat gaa gta cat tgg gag       480
Ser Gln Gly Val Ile Leu Pro Ile Lys Ser His Glu Val His Trp Glu
145                 150                 155                 160 acc tgc agg aca gtg ccc ttc agc cag act ata acc cac gaa ggc tgt       528
Thr Cys Arg Thr Val Pro Phe Ser Gln Thr Ile Thr His Glu Gly Cys
                165                 170                 175 gaa aaa gta gtt gtt cag aac aac ctt tgc ttt ggg aaa tgc ggg tct       576
Glu Lys Val Val Val Gln Asn Asn Leu Cys Phe Gly Lys Cys Gly Ser
```

```
                    180              185              190
gtt cat ttt cct gga gcc gcg cag cac tcc cat acc tcc tgc tct cac      624
Val His Phe Pro Gly Ala Ala Gln His Ser His Thr Ser Cys Ser His
        195                 200                 205 tgt ttg cct gcc aag ttc acc acg atg cac ttg cca ctg aac tgc act      672
Cys Leu Pro Ala Lys Phe Thr Thr Met His Leu Pro Leu Asn Cys Thr
210                 215                 220 gaa ctt tcc tcc gtg atc aag gtg gtg atg ctg gtg gag gag tgc cag      720
Glu Leu Ser Ser Val Ile Lys Val Val Met Leu Val Glu Glu Cys Gln
225                 230                 235                 240 tgc aag gtg aag acg gag cat gaa gat gga cac atc cta cat gct ggc      768
Cys Lys Val Lys Thr Glu His Glu Asp Gly His Ile Leu His Ala Gly
                245                 250                 255 tcc cag gat tcc ttt atc cca gga gtt tca gct tga                      804
Ser Gln Asp Ser Phe Ile Pro Gly Val Ser Ala
            260                 265
```

<210> SEQ ID NO 12
<211> LENGTH: 267
<212> TYPE: PRT
<213> ORGANISM: Homo sapiens

<400> SEQUENCE: 12

```
Met His Leu Leu Leu Phe Gln Leu Leu Val Leu Leu Pro Leu Gly Lys
1               5                   10                  15

Thr Thr Arg His Gln Asp Gly Arg Gln Asn Gln Ser Ser Leu Ser Pro
            20                  25                  30

Val Leu Leu Pro Arg Asn Gln Arg Glu Leu Pro Thr Gly Asn His Glu
        35                  40                  45

Glu Ala Glu Glu Lys Pro Asp Leu Phe Val Ala Val Pro His Leu Val
    50                  55                  60

Ala Thr Ser Pro Ala Gly Glu Gly Gln Arg Gln Arg Glu Lys Met Leu
65                  70                  75                  80

Ser Arg Phe Gly Arg Phe Trp Lys Lys Pro Glu Arg Glu Met His Pro
                85                  90                  95

Ser Arg Asp Ser Asp Ser Glu Pro Phe Pro Pro Gly Thr Gln Ser Leu
            100                 105                 110

Ile Gln Pro Ile Asp Gly Met Lys Met Glu Lys Ser Pro Leu Arg Glu
        115                 120                 125

Glu Ala Lys Lys Phe Trp His His Phe Met Phe Arg Lys Thr Pro Ala
    130                 135                 140

Ser Gln Gly Val Ile Leu Pro Ile Lys Ser His Glu Val His Trp Glu
145                 150                 155                 160

Thr Cys Arg Thr Val Pro Phe Ser Gln Thr Ile Thr His Glu Gly Cys
                165                 170                 175

Glu Lys Val Val Val Gln Asn Asn Leu Cys Phe Gly Lys Cys Gly Ser
            180                 185                 190

Val His Phe Pro Gly Ala Ala Gln His Ser His Thr Ser Cys Ser His
        195                 200                 205

Cys Leu Pro Ala Lys Phe Thr Thr Met His Leu Pro Leu Asn Cys Thr
210                 215                 220

Glu Leu Ser Ser Val Ile Lys Val Val Met Leu Val Glu Glu Cys Gln
225                 230                 235                 240

Cys Lys Val Lys Thr Glu His Glu Asp Gly His Ile Leu His Ala Gly
                245                 250                 255

Ser Gln Asp Ser Phe Ile Pro Gly Val Ser Ala
```

-continued

```
                   260             265

<210> SEQ ID NO 13
<211> LENGTH: 2032
<212> TYPE: DNA
<213> ORGANISM: Homo sapiens
<220> FEATURE:
<221> NAME/KEY: source
<222> LOCATION: (1)..(2032)
<223> OTHER INFORMATION: Homo sapiens:  Taxon:9606
<220> FEATURE:
<221> NAME/KEY: gene
<222> LOCATION: (1)..(2032)
<223> OTHER INFORMATION: BMPR1B
<220> FEATURE:
<221> NAME/KEY: CDS
<222> LOCATION: (274)..(1782)
<223> OTHER INFORMATION: Serine/threonine receptor kinase
<220> FEATURE:
<221> NAME/KEY: misc_feature
<222> LOCATION: (367)..(606)
<223> OTHER INFORMATION: Activin_recp; Region:  Activin types I and II
<220> FEATURE:
<221> NAME/KEY: misc_feature
<222> LOCATION: (883)..(1746)
<223> OTHER INFORMATION: pkinase; Region:  Eukaryotic protein kinase
      domain
<220> FEATURE:
<221> NAME/KEY: misc_feature
<222> LOCATION: (883)..(1746)
<223> OTHER INFORMATION: TyrKc; Region:  Tyrosina kinase, catalytic
      domain
<220> FEATURE:
<221> NAME/KEY: misc_feature
<222> LOCATION: (883)..(1725)
<223> OTHER INFORMATION: TKc; Region:  Serine/Threonine protein
      kinases, catalytic domain
<300> PUBLICATION INFORMATION:
<301> AUTHORS: ten Dijke, P., Yamashita, H., Ichijo, H., Franzen, P.,
      Laiho, M., Miyazono, K., and Heldin, C.H.
<302> TITLE: Characterization of type I receptors for transforming
      growth factor-beta and activin
<303> JOURNAL: Science
<304> VOLUME: 264
<305> ISSUE: 5155
<306> PAGES: 101-104
<307> DATE: 1994
<308> DATABASE ACCESSION NUMBER: NM_001203
<309> DATABASE ENTRY DATE: 2000-10-31
<313> RELEVANT RESIDUES: (1)..(2032)
<300> PUBLICATION INFORMATION:
<301> AUTHORS: Ide, H., Katoh, M., Sasaki, H., Yoshida, T., Aoki, K.,
      Nawa, Y., Osada, Y., Sugimura, T., and Terada, M.
<302> TITLE: Cloning of human bone morphogenetic protein type IB
      receptor (BMPR-IB) and its expression in prostate cancer in
      comparison with other BMPRs
<303> JOURNAL: Oncogene
<304> VOLUME: 14
<305> ISSUE: 11
<306> PAGES: 1377-1382
<307> DATE: 1997
<308> DATABASE ACCESSION NUMBER: NM_001203
<309> DATABASE ENTRY DATE: 2000-10-31
<313> RELEVANT RESIDUES: (1)..(2032)
<300> PUBLICATION INFORMATION:
<301> AUTHORS: Ide, H., Saito-Ohara, P., Ohnami, S., Osada, Y.,
      Ikeuchi, T., Yoshida, T., and Terada, M.
<302> TITLE: Assignment of the BMPR1A and BMPR1B genes to human
      chromosome 10q22.3 and
<302> TITLE: 4q23?q24 by in situ hybridization and radiation hybrid
      mapping
<303> JOURNAL: Cytogenet. Cell. Genet.
<304> VOLUME: 81
<305> ISSUE: 3
<306> PAGES: 285-286
<307> DATE: 1998
<308> DATABASE ACCESSION NUMBER: NM_001203
<309> DATABASE ENTRY DATE: 2000-10-31
```

-continued

```
<313> RELEVANT RESIDUES: (1)..(2032)
<300> PUBLICATION INFORMATION:
<301> AUTHORS: Astrom, A.K., Jin, D., Imamura, T., Roijer, E.,
       Rosenzweig, B., Miyazono, K., ten Dijke, P., and Stenman, G.
<302> TITLE: Chromosomal localization of three human genes encoding
       bone
       morphogenetic protein receptors
<303> JOURNAL: Mamm. Genome
<304> VOLUME: 10
<305> ISSUE: 3
<306> PAGES: 299-302
<307> DATE: 1999
<308> DATABASE ACCESSION NUMBER: NM_001203
<309> DATABASE ENTRY DATE: 2000-10-31
<313> RELEVANT RESIDUES: (1)..(2032)

<400> SEQUENCE: 13
```

| | |
|---|---:|
| cgcggggcgc ggagtcggcg gggcctcgcg ggacgcgggc agtgcggaga ccgcggcgct | 60 |
| gaggacgcgg gagccgggag cgcacgcgcg gggtggagtt cagcctactc tttcttagat | 120 |
| gtgaaaggaa aggaagatca tttcatgcct tgttgataaa ggttcagact tctgctgatt | 180 |
| cataaccatt tggctctgag ctatgacaag agaggaaaca aaagttaaa cttacaagcc | 240 |
| tgccataagt gagaagcaaa cttccttgat aac atg ctt ttg cga agt gca gga | 294 |
|                                                  Met Leu Leu Arg Ser Ala Gly<br>                                                  1             5 | |
| aaa tta aat gtg ggc acc aag aaa gag gat ggt gag agt aca gcc ccc<br>Lys Leu Asn Val Gly Thr Lys Lys Glu Asp Gly Glu Ser Thr Ala Pro<br>         10                   15                  20 | 342 |
| acc ccc cgt cca aag gtc ttg cgt tgt aaa tgc cac cac cat tgt cca<br>Thr Pro Arg Pro Lys Val Leu Arg Cys Lys Cys His His His Cys Pro<br>25                   30                   35 | 390 |
| gaa gac tca gtc aac aat att tgc agc aca gac gga tat tgt ttc acg<br>Glu Asp Ser Val Asn Asn Ile Cys Ser Thr Asp Gly Tyr Cys Phe Thr<br>40                 45                   50                  55 | 438 |
| atg ata gaa gag gat gac tct ggg ttg cct gtg gtc act tct ggt tgc<br>Met Ile Glu Glu Asp Asp Ser Gly Leu Pro Val Val Thr Ser Gly Cys<br>                   60                   65                   70 | 486 |
| cta gga cta gaa ggc tca gat ttt cag tgt cgg gac act ccc att cct<br>Leu Gly Leu Glu Gly Ser Asp Phe Gln Cys Arg Asp Thr Pro Ile Pro<br>         75                   80                   85 | 534 |
| cat caa aga aga tca att gaa tgc tgc aca gaa agg aac gaa tgt aat<br>His Gln Arg Arg Ser Ile Glu Cys Cys Thr Glu Arg Asn Glu Cys Asn<br>                   90                   95                 100 | 582 |
| aaa gac cta cac cct aca ctg cct cca ttg aaa aac aga gat ttt gtt<br>Lys Asp Leu His Pro Thr Leu Pro Pro Leu Lys Asn Arg Asp Phe Val<br>105                 110                115 | 630 |
| gat gga cct ata cac cac agg gct tta ctt ata tct gtg act gtc tgt<br>Asp Gly Pro Ile His His Arg Ala Leu Leu Ile Ser Val Thr Val Cys<br>120                 125                130                135 | 678 |
| agt ttg ctc ttg gtc ctt ata ata tta ttt tgt tac ttc cgg tat aaa<br>Ser Leu Leu Leu Val Leu Ile Ile Leu Phe Cys Tyr Phe Arg Tyr Lys<br>                   140                  145                150 | 726 |
| aga caa gaa acc aga cct cga tac agc att ggg tta gaa cag gat gaa<br>Arg Gln Glu Thr Arg Pro Arg Tyr Ser Ile Gly Leu Glu Gln Asp Glu<br>                   155                  160                165 | 774 |
| act tac att cct cct gga gaa tcc ctg aga gac tta att gag cag tct<br>Thr Tyr Ile Pro Pro Gly Glu Ser Leu Arg Asp Leu Ile Glu Gln Ser<br>         170                   175                  180 | 822 |
| cag agc tca gga agt gga tca ggc ctc cct ctg ctg gtc caa agg act<br>Gln Ser Ser Gly Ser Gly Ser Gly Leu Pro Leu Leu Val Gln Arg Thr<br>185                 190                195 | 870 |
| ata gct aag cag att cag atg gtg aaa cag att gga aaa ggt cgc tat | 918 |

```
                Ile Ala Lys Gln Ile Gln Met Val Lys Gln Ile Gly Lys Gly Arg Tyr
                200                 205                 210                 215 ggg aaa gtt tgg atg gga aag tgg cgt ggc gaa aag gta gct gtg aaa            966
Gly Glu Val Trp Met Gly Lys Trp Arg Gly Glu Lys Val Ala Val Lys
                    220                 225                 230 gtg ttc ttc acc aca gag gaa gcc agc tgg ttc aga gag aca gaa ata          1014
Val Phe Phe Thr Thr Glu Glu Ala Ser Trp Phe Arg Glu Thr Glu Ile
                235                 240                 245 tat cag aca gtg ttg atg agg cat gaa aac att ttg ggt ttc att gct          1062
Tyr Gln Thr Val Leu Met Arg His Glu Asn Ile Leu Gly Phe Ile Ala
            250                 255                 260 gca gat atc aaa ggg aca ggg tcc tgg acc cag ttg tac cta atc aca          1110
Ala Asp Ile Lys Gly Thr Gly Ser Trp Thr Gln Leu Tyr Leu Ile Thr
        265                 270                 275 gac tat cat gaa aat ggt tcc ctt tat gat tat ctg aag tcc acc acc          1158
Asp Tyr His Glu Asn Gly Ser Leu Tyr Asp Tyr Leu Lys Ser Thr Thr
280                 285                 290                 295 cta gac gct aaa tca atg ctg aag tta gcc tac tct tct gtc agt ggc          1206
Leu Asp Ala Lys Ser Met Leu Lys Leu Ala Tyr Ser Ser Val Ser Gly
                    300                 305                 310 tta tgt cat tta cac aca gaa atc ttt agt act caa ggc aaa cca gca          1254
Leu Cys His Leu His Thr Glu Ile Phe Ser Thr Gln Gly Lys Pro Ala
                315                 320                 325 att gcc cat cga gat ctg aaa agt aaa aac att ctg gtg aag aaa aat          1302
Ile Ala His Arg Asp Leu Lys Ser Lys Asn Ile Leu Val Lys Lys Asn
            330                 335                 340 gga act tgc tgt att gct gac ctg ggc ctg gct gtt aaa ttt att agt          1350
Gly Thr Cys Cys Ile Ala Asp Leu Gly Leu Ala Val Lys Phe Ile Ser
        345                 350                 355 gat aca aat gaa gtt gac ata cca cct aac act cga gtt ggc acc aaa          1398
Asp Thr Asn Glu Val Asp Ile Pro Pro Asn Thr Arg Val Gly Thr Lys
360                 365                 370                 375 cgc tat atg cct cca gaa gtg ttg gac gag agc ttg aac aga aat cac          1446
Arg Tyr Met Pro Pro Glu Val Leu Asp Glu Ser Leu Asn Arg Asn His
                    380                 385                 390 ttc cag tct tac atc atg gct gac atg tat agt ttt ggc ctc atc ctt          1494
Phe Gln Ser Tyr Ile Met Ala Asp Met Tyr Ser Phe Gly Leu Ile Leu
                395                 400                 405 tgg gag gtt gct agg aga tgt gta tca gga ggt ata gtg gaa gaa tac          1542
Trp Glu Val Ala Arg Arg Cys Val Ser Gly Gly Ile Val Glu Glu Tyr
            410                 415                 420 cag ctt cct tat cat gac cta gtg ccc agt gac ccc tct tat gag gac          1590
Gln Leu Pro Tyr His Asp Leu Val Pro Ser Asp Pro Ser Tyr Glu Asp
        425                 430                 435 atg agg gag att gtg tgc atc aag aag tta cgc ccc tca ttc cca aac          1638
Met Arg Glu Ile Val Cys Ile Lys Lys Leu Arg Pro Ser Phe Pro Asn
440                 445                 450                 455 cgg tgg agc agt gat gag tgt cta agg cag atg gga aaa ctc atg aca          1686
Arg Trp Ser Ser Asp Glu Cys Leu Arg Gln Met Gly Lys Leu Met Thr
                    460                 465                 470 gaa tgc tgg gct cac aat cct gca tca agg ctg aca gcc ctg cgg gtt          1734
Glu Cys Trp Ala His Asn Pro Ala Ser Arg Leu Thr Ala Leu Arg Val
                475                 480                 485 aag aaa aca ctt gcc aaa atg tca gag tcc cag gac att aaa ctc tga          1782
Lys Lys Thr Leu Ala Lys Met Ser Glu Ser Gln Asp Ile Lys Leu
            490                 495                 500 taggagagga aaagtaagca tctctgcaga aagccaacag gtactcttct gtttgtgggc        1842
agagcaaaag acatcaaata agcatccaca gtacaagcct tgaacatcgt cctgcttccc       1902
```

```
agtgggttca gacctcacct ttcagggagc gacctgggca aagacagaga agctcccaga    1962
aggagagatt gatccgtgtc tgtttgtagg cggagaaacc gttgggtaac ttgttcaaga    2022
tatgatgcat                                                           2032
```

<210> SEQ ID NO 14
<211> LENGTH: 502
<212> TYPE: PRT
<213> ORGANISM: Homo sapiens

<400> SEQUENCE: 14

```
Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Asp Ser Gly Leu
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
    210                 215                 220

Gly Glu Lys Val Ala Val Lys Val Phe Phe Thr Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
            260                 265                 270

Thr Gln Leu Tyr Leu Ile Thr Asp Tyr His Glu Asn Gly Ser Leu Tyr
        275                 280                 285

Asp Tyr Leu Lys Ser Thr Thr Leu Asp Ala Lys Ser Met Leu Lys Leu
    290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
            340                 345                 350
```

```
Leu Ala Val Lys Phe Ile Ser Asp Thr Asn Glu Val Asp Ile Pro Pro
            355                 360                 365

Asn Thr Arg Val Gly Thr Lys Arg Tyr Met Pro Pro Glu Val Leu Asp
        370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
                405                 410                 415

Gly Gly Ile Val Glu Glu Tyr Gln Leu Pro Tyr His Asp Leu Val Pro
            420                 425                 430

Ser Asp Pro Ser Tyr Glu Asp Met Arg Glu Ile Val Cys Ile Lys Lys
        435                 440                 445

Leu Arg Pro Ser Phe Pro Asn Arg Trp Ser Ser Asp Glu Cys Leu Arg
    450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
                485                 490                 495

Ser Gln Asp Ile Lys Leu
            500

<210> SEQ ID NO 15
<211> LENGTH: 20
<212> TYPE: DNA
<213> ORGANISM: Homo sapiens

<400> SEQUENCE: 15
acgagagctc tcactggtcc                                               20

<210> SEQ ID NO 16
<211> LENGTH: 20
<212> TYPE: DNA
<213> ORGANISM: Homo sapiens

<400> SEQUENCE: 16
cattccggat tacatgaggg                                               20

<210> SEQ ID NO 17
<211> LENGTH: 19
<212> TYPE: DNA
<213> ORGANISM: Homo sapiens

<400> SEQUENCE: 17
cctgagcgag ttcgagttg                                                19

<210> SEQ ID NO 18
<211> LENGTH: 19
<212> TYPE: DNA
<213> ORGANISM: Homo sapiens

<400> SEQUENCE: 18
cactcgtttc tggtagttc                                                19

<210> SEQ ID NO 19
<211> LENGTH: 19
<212> TYPE: DNA
<213> ORGANISM: Homo sapiens

<400> SEQUENCE: 19
```

```
tacctgagac gggaagaaa                                              19

<210> SEQ ID NO 20
<211> LENGTH: 20
<212> TYPE: DNA
<213> ORGANISM: Homo sapiens

<400> SEQUENCE: 20
ccagactgaa gccggtaaag                                             20
```

BONE MORPHOGENETIC PROTEIN-2 IN THE TREATMENT AND DIAGNOSIS OF CANCER

PRIORITY CLAIM

This present application is a divisional of U.S. application Ser. No. 10/692,824 filed Oct. 23, 2003, now abandoned, which is a continuation-in-part of US application. Ser. No. 10/044,716 filed Jan. 11, 2002, now abandoned, which is a converted utility application claiming the benefit of U.S. Provisional Application No. 60/261,252 (Langenfeld), filed Jan. 12, 2001, all of which are incorporated by reference in their entirety herein.

FIELD OF USE

The present invention relates to the fields of molecular biology, immunology, and medicine and provides methods for the treatment and diagnosis of cancer. Specifically, it relates to the use of bone morphogenetic protein-2 (BMP-2), as a target for tumor and cancer treatment therapies, a marker to diagnose cancer, and as using antagonists to BMP-2 to reduce neoangiogenesis and continued vascularization of tumors.

BACKGROUND OF THE INVENTION

Various publications or patents are referred to in parentheses throughout this application. Each of these publications or patents is incorporated by reference herein. Complete citations of scientific publications are set forth in the text or at the end of the specification.

Lung cancer is the leading cause of cancer deaths in the United States with an estimated 157,000 people expected to die from the disease in 2003. (1) Despite improvements in diagnosis and treatment, only 15% of lung cancer patients survive five years (1) with the majority of patients succumbing due to spread of the cancer to other parts of the body. The genes that induce the invasion and metastasis of lung cancers are still poorly understood.

The bone morphogenetic proteins (BMPs) are members of the transforming growth factor (TGF) superfamily, which are a phytogenetically conserved group of proteins (2). There are 20 isotypes of the BMPs with BMP-2 and BMP-4 sharing 92% homology (3). BMP-2 and BMP-4 are secreted proteins that induce pluripotential mesenchymal differentiation (4, 5, 6) and are required for the normal embryonic development of many organs including lung and bone (7, 8). Animals with functional knockout of BMP-2/4 die between 6.5 and 9.5 days post conception with little to no mesoderm differentiation.

BMP-2 is a powerful morphogenetic protein that has been studied for its ability to induce the cascade of endochondral bone formation. BMP-2 can induce the entire developmental program of endochondral osteogenesis when introduced at an ectopic site (9). BMP-2 and BMP-4 also have chemotactic properties capable of inducing the migration of normal vascular endothelial and mononuclear cells (10, 11).

The BMPs are synthesized as inactive variable length precursor proteins (12, 13). The precursor BMP-2 proteins are proteolytically cleaved, producing a mature C-terminal 14-kDa protein that is the active peptide (9, 12). Mature BMP-2 protein signaling is mediated by transmembrane serine/threonine kinases called type IA, IB, and type II receptors (14-17). The receptor phosphorylates cytoplasmic targets, which includes the Smad family of proteins (18). Smads are a class of proteins that function as intracellular signaling effectors for the TGF-β superfamily of secreted polypeptides. The activated BMP type I receptor then phosphorylates Smad1, Smad 5, and/or Smad 8, inducing its translocation into the nucleus and activating the transcription of target genes.

While BMP-2 expression has been noted in a few cancers, such as sarcomas (19), pancreatic cancer (20), and in cancer cell lines (21), inhibition of BMP-2 activity as a potential cancer treatment has neither been mentioned nor studied in the literature. To the contrary, several articles suggest that BMP-2 has an inhibitory effect on cancer cell proliferation and may be a useful therapeutic agent to treat cancer. (22, 23, 24). Thus, any teaching that BMP-2 is a compound expected to treat cancer or treat the risk of cancer would be new and unexpected.

The development of a blood supply is essential for bone formation. BMPs were thought to promote angiogenesis indirectly in developing bone by inducing the expression of VEGF from osteoblasts. BMP-6 was shown to stimulate the migration and tube formation of bovine aortic endothelial cells (BAEC) (27). Functional knockouts of TGF superfamily members demonstrate their role in vasculogenesis. Mice with a functional knockout of Smad 1 or Smad 5 die at approximately 9.5 to 10.5 weeks and have defects in angiogenesis. Smad 5 mutant embryos had enlarged blood vessels, a decrease in smooth muscle cells, and contained mesenchymal cells, which were unable to direct angiogenesis. Mice lacking TGF receptors died in mid-gestation with defects in angiogenesis. However, the BMPs have never been shown to be associated with the formation of a neovasculature in tumors. This discovery would elucidate a significant relationship.

Id has an important role in mediating an angiogenic response. Mice with a double knockout of ID1-Id3 display vascular abnormalities in the forebrain. ID1±Id3−/− mutant mice failed to support the growth of xenograft tumors, which is thought to occur from the inability to form a neovasculature. Sustained expression of Id cells delays the onset of senescence in human endothelial cells. Id has also been shown to stimulate proliferation of epithelial cells. It was recently shown that ID1 mediates BMP-6 induced migration and possibly also mediates tube formation. (27)

VEGF is the most potent angiogenic factor and is thought to be essential for tumor growth and metastasis. (29, 30) Transgenic mice studies have confirmed that overexpression of sonic hedgehog can cause tissue-targeted cancer. (31)

Noggin, a natural inhibitor of BMP-2, is a secreted protein that binds BMP-2 and BMP-4, thereby preventing their activation of the BMP receptors. (8, 32, 33, 34, 35) Mouse and human noggin are 98% homologous.

The inactivation of Rb by either a point mutation or phosphorylation is thought to occur in 100% of lung carcinomas. When Rb is in a hypophosphorylated state, it is able to block the progression through G1 of the cell cycle. When Rb is inactivated by phosphorylation, this allows progression through G1. Cyclin E is required for progression through G1 of the cell cycle. The expression of cyclin E increases during G1 of the cell cycle. Cyclin E then binds to cyclin dependent kinase 2 (ckd-2) leading to Rb phosphorylation. Cyclin E is frequently over-expressed in lung and other cancers and is thought to contribute to a worse prognosis. Dysregulation of the Ras/Mek/Erk occurs in lung and many other carcinomas. Over-expression of the Ras/Mek/Erk pathway enhances cellular proliferation and promotes transformation. BMP-2 was previously shown to induce Ras/Mek/Erk signaling in osteoblasts.

BMP-2/4 has been shown to induce expression of ID1 in breast carcinoma cell lines, endothelial cells, osteoblasts (45), immortalized human stromal (46), and mouse embryonic stem cells (47). ID1-3 are helix-loop-helix proteins that serve as negative regulators of basic helix-loop-helix transcription factors. ID1 is thought to have an important role in tumorigenesis (48-49). Id1 has been shown to immortalize human keratinocytes through activation of telomerase and Rb inactivation (28). Id1±Id3−/− knockout mice are unable to support xenograft tumor growth, which thought to occur because lack of neoangiogenesis. Id1 and Id2 have been shown to be critical for the progression of G1 of the cell cycle, which occurs at least in part, by inactivation p16, which leads hyperphosphorylation of Rb.

SUMMARY OF THE INVENTION

The present invention is related to the discovery that bone morphogenetic protein-2 (BMP-2) is overexpressed in many common human cancers and is linked to cancer invasion and growth. Further, inhibiting BMP-2 activity reduces the size of cancerous tumors in nude mice and down regulates the expression of VEGF and sonic hedgehog in lung cancer cell lines. Thus, the present invention pertains to the use of BMP-2 as a target for cancer treatment therapies and a means to diagnose cancer. Specifically, the therapeutic component of this invention involves administering to a patient a composition that inhibits bone morphogenetic protein-2 activity. The diagnostic component of the invention involves measuring the BMP-2 level in biological samples from both a patient and a non-cancerous subject and comparing those levels. Elevated levels indicate increased probability of cancer in the patient.

A primary aspect of the present invention is to provide a method for the treatment of cancer by administering to a patient a therapeutically effective amount of a BMP-2 activity inhibitor. Some cancers that may be treated by this method are carcinomas, including, but not limited to, lung cancer, bladder cancer, breast cancer, colon cancer, kidney cancer, lung cancer, ovarian cancer, thyroid cancer, endometrial cancer, omental cancer, testicular cancer, and liver cancer. In a preferred embodiment of this invention, the patient is human.

The BMP-2-inhibitor of this invention may be a polypeptide that binds specifically to bone morphogenetic protein-2 itself, a polypeptide that binds specifically to a BMP-2 receptor, or an antibody that binds specifically to BMP-2 or a portion of BMP-2. The BMP-2 inhibitor may also be an antisense oligonucleotide that binds to a BMP-2 nucleic acid sequence or some portion thereof.

This invention features several particular polypeptides that are BMP-2 inhibitors. Preferred embodiments of this invention feature known antagonists to BMP-2, such as noggin, chordin, cerberus 1 homolog, gremlin, and DAN (2-deoxy-2,3-didehydro-D-N-acetylneuraminic acid). Noggin is particularly preferred. Another aspect of this invention relates to the use of fragments of noggin, chordin, cerberus 1 homolog, gremlin, and DAN as BMP-2 inhibitors.

Another embodiment of this invention provides a method for treating cancer by administering to a patient a therapeutically effective amount of an expression vector encoding a BMP-2 inhibitor, such as a polypeptide that binds BMP-2 or an antisense oligonucleotide that binds to the nucleic acid for BMP-2. Another aspect of this invention includes the expression vector described above in which the nucleic acid sequence for BMP-2 is operably linked to a selective promoter. One preferred selective promoter encompassed by this invention is carcinoembryonic antigen promoter.

This invention also encompasses a kit that includes packaging material, a BMP-2 activity inhibitor, and instructions that indicate that the compound can be used for treating cancer in a patient. One type of cancer that may be treated is carcinoma. Particular carcinomas encompassed by this invention are lung cancer, bladder cancer, breast cancer, colon cancer, kidney cancer, ovarian cancer, thyroid cancer, endometrial cancer, omental cancer, testicular cancer, and liver cancer.

The diagnostic component of this invention includes a method for diagnosing cancer in a patient by obtaining a biological sample from a patient and measuring the level of BMP-2 in the biological sample, with an elevated level of BMP-2 indicating an increased likelihood of cancer in the patient.

Any assay available to measure BMP-2 levels is encompassed by this invention. Particularly preferred are immunoassays. Some examples of immunoassays included in this invention are Enzyme-Linked Immunosorbent Assay (ELISA), Western blot, immunoprecipitation, in situ immunohistochemistry, and immunofluorescence. ELISA is most particularly preferred.

Another aspect of this invention is a method for the diagnosis of cancer in a patient by detecting overexpression of BMP-2 in the patient by (i) quantifying in vivo or in vitro the presence of BMP-2 in a patient or a biological sample obtained from a patient, (ii) comparing the result obtained in step (i) to that of a normal, non-cancerous patient, and (iii) diagnosing the presence of cancer based on an increased level of BMP-2 in step (ii) relative to a normal, non-cancerous patient.

An additional aspect of the present invention demonstrates that BMP-2 stimulates lung tumorigenesis by stimulating angiogenesis of developing tumors. Furthermore, BMP-2 induced angiogenesis involves a direct activation of human endothelial cells. The present invention has discovered that vascular endothelial growth factor (VEGF), which is an active target in cancer therapy, stimulates BMP-2. Thus, BMP-2 enhances tumorigenesis by mediating an angiogenic response.

A therapeutic aspect of the invention comprises administering a therapeutically effective amount of a BMP-2 activity inhibitor to a patient to treat tumors or to treat the risk of developing tumors in a patient by decreasing vascular development and/or angiogenesis. Preferably, the BMP-2 activity inhibitor is administered in a therapeutically effective carrier and the administration is continued until the tumor or risk of the tumor is treated.

BMP-2 also mediates robust tube formation in both human aortic endothelial cells and human umbilical vein endothelial cells, which demonstrates its role in inducing endothelial differentiation. BMP-2 activates cancer cells to express Id, cyclin E, phosphorylation of Rb and Erk ½. BMP-2 also activates PI-3, MEK, and p38, all of which are involved in pathways involved in the transformation of cancers. Thus, another aspect of the present invention comprises a method of decreasing expression of Id, cyclin E, and phosphorylation of Rb and Erk ½ in cancer cells or precancerous cells.

BRIEF DESCRIPTION OF THE DRAWINGS

FIG. 1(a) shows amplification of cDNA prior to subtraction. Lane 1: IHBE cells; lane 2: lung carcinoma. FIG. 1(b) shows the distinct cDNA bands present after the second round of subtraction and amplification. FIG. 1(c) lists the proteins that were identified by a BLAST data base search after the DNA corresponding to each of the bands shown in FIG. 1(b) was isolated and sequenced.

FIG. 3(a) is a representative Western blot showing overexpression of BMP-2 in cancer tissue specimens. Lanes 1-5: normal lung tissue, lane 6: SOAS osteosarcoma cell line, lanes 7-11: non-small lung cell carcinomas. FIG. 3(b) is the corresponding actin immunoblot. FIG. 3(c) is a Western blot of non-small cell lung carcinoma (NSCLC) subtypes. Lanes 1-4: normal lung tissue, lane 5: squamous carcinoma, lane 6: adenocarcinoma, lane 7: bronchoalveolar carcinoma, lane 8: large cell carcinoma. FIG. 3(d) is the actin immunoblot corresponding to FIG. 3(c). FIG. 3(e) is a BMP-2 immunoblot of lane 1: benign lung tumor, lane 2: mesthotheleoma, lane 3: normal lung tissue, lane 4: carcinoid tumor, lane 5: normal lung, lane 6: NSCLC, lane 7: normal lung tissue, lane 8: NSCLC, lane 9: recombinant BMP-4. FIG. 3(f) is a BMP-4-probed Western blot with the same lane contents as FIG. 3(e), except lane 9, which is recombinant BMP-4. FIG. 3(g) is the actin immunoblot corresponding to FIG. 3(f).

FIG. 7(a) is a Western blot showing BMP-2 expression in metastatic tumors. Lane 1: interstitial inflammatory lung disease, lane 2: normal omentum, lane 3: metastatic kidney tumor, lane 4: normal lymph node, lane 5: metastatic breast cancer, lane 6: metastatic kidney tumor, lane 7: metastatic NSCLC, lane 8: omentum carcinoma. FIG. 7(b) is the corresponding actin immunoblot. FIG. 7(c) is a BMPR IA Western blot, while FIG. 7(d) is a BMPR IB Western blot. The contents of the lanes on both blots are the same: lane 1: normal kidney, lanes 2-3: normal lung, lane 4: metastatic kidney carcinoma, lane 5: metastatic breast carcinoma, lane 6: metastatic NSCLC, lanes 7-9: NSCLC. FIG. 7(e) is BMPR IA Western blot and FIG. 7(f) is a BMPR IB Western blot of common human carcinomas. Lane contents are the same on both blots: lane 1: normal kidney, lane 2: normal endometrium, lane 3: omentum, lane 4: normal colon, lane 5: ovarian carcinoma, lane 6: kidney carcinoma, lane 7: endometrial carcinoma, lane 8: omental tumor, lane 9: colon carcinoma.

FIG. 9(a) is the resulting Western blot: lane 1: A549 lysate, lane 2: media without leukocytes, lanes 3-4: media with human leukocytes. FIG. 9(b) is the same immunoblot hybridized with BMP-2 antibody recognizing its N-terminal end. FIG. 9(c) is a Western blot of leukocyte samples probed with anti-furin antibody.

FIG. 11(a) on the left is the control. FIG. 11(b) on the right is BMP-2 treated tissue.

FIG. 12(a) is a Western blot that was probed with anti-sonic hedgehog and shows an increase in sonic hedgehog expression as the amount of recombinant BMP-2 added to the A549 cell culture is increased. Lane 1 is A549 lysate and 100 ng of BMP. Lane 2 is A549 lysate and 10 ng of BMP. Lane 3 is A549 lysate and 1 ng of BMP. Lane 4 is A549 lysate and 500 pg of BMP. Lane 5 is A549 lysate without any BMP. The Western blot on the right, FIG. 12(b), was probed with anti-sonic hedgehog and shows A549 cell culture media without added noggin (Lane 1) and cell culture media with added noggin (Lane 2).

FIG. 13 shows that BMP-2 stimulates the migration of A549 and H7249 human lung cancer cell lines. FIG. 13(c): H7249 cells migrated off cover slips towards Affi-Blue agarose beads containing recombinant BMP-2. FIG. 13(d): H7249 cells did not migrate off cover slips toward AffiBlue agarose beads containing dilution buffer. Similar results were found using the A549 cells. All the above experiments were repeated at least 3 times. Data is presented as mean±standard deviation.

FIG. 15(b) is a chart showing the results of an ELISA.

FIG. 24 is a chart of the percentage of cells with Smad 1/5/8 nuclear staining in two types of media, 5% FCS and LHC-8 SFM, for 15, 30, and 120 minutes. A vehicle is also added for control purposes.

DETAILED DESCRIPTION OF THE INVENTION

Figure 1:
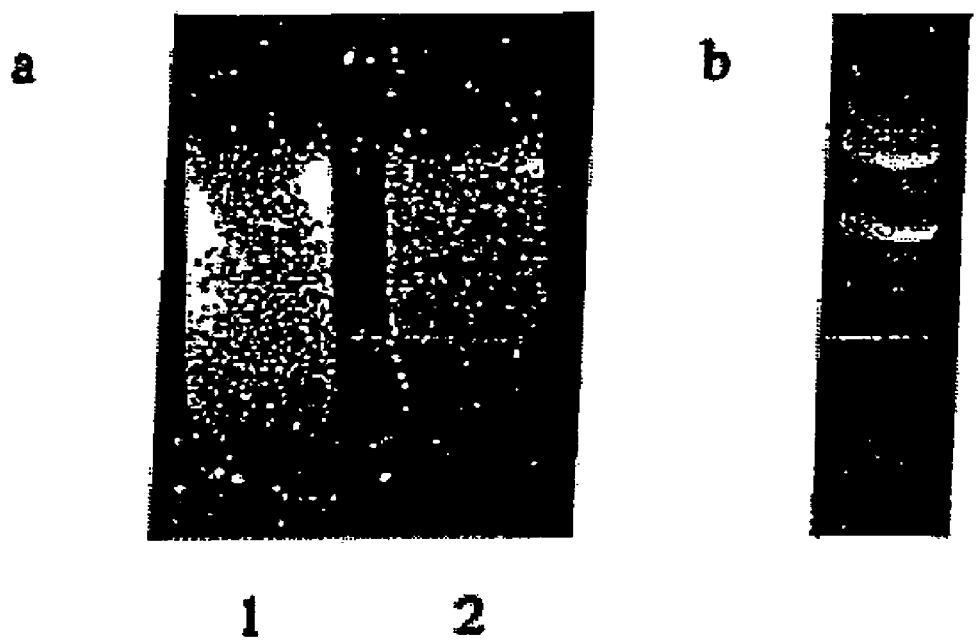
FIG. 1 illustrates representational difference analysis (RDA) subtraction.

The present invention is related to the present discovery that the overexpression of bone morphogenetic protein-2 (BMP-2) is linked to cancer invasion and growth. BMP-2 is overexpressed in many common human cancers and regulates molecular pathways that are involved in the promotion of cancer. Inhibiting BMP-2 activity reduces the size of cancerous tumors in nude mice and down regulates the expression of VEGF and sonic hedgehog, both known cancer promoters, in lung cancer cell lines. Thus, the present invention is directed toward using BMP-2 as a target for cancer treatment therapies and as a means to diagnose cancer.

The therapeutic component of this invention involves administering to a patient a composition that inhibits bone morphogenetic protein-2 activity. Such inhibition may be accomplished by ligands or antibodies that bind to BMP-2 or BMP-2 receptors. It may also be achieved by preventing the processing of pro-BMP-2, or blocking transcription or replication of BMP-2 DNA or translation of BMP-2 mRNA. Delivery of such compositions may be systemic or tissue-targeted. Additionally, decreased vascularization and decreased tumor expression may be achieved by decreasing the expression of Id, cyclin E, and phosphorylation of Rb and Erk ½ and controlling the activity of other tumor enhancing genes.

The diagnostic component of the invention involves measuring the BMP-2 level in biological samples from a patient and determining whether that level is elevated from a normal level. A related aspect of the invention involves measuring the BMP-2 level in biological samples from both a patient and a non-cancerous subject and comparing those levels. Presumably, the levels of BMP-2 in the non-cancerous subject are physiologically normal levels. Preferably, the levels are taken from a study of non-cancerous subjects of a similar age and the level of BMP-2 is from a similar or the same organ, fluid or bodily location. Elevated levels of BMP-2 in the patient compared to the non-cancerous subject indicate cancer.

Although specific embodiments of the present invention will now be described, it should be understood that such embodiments are examples that are merely illustrative of a small number of the many possible specific embodiments that can represent applications of the principles of the present invention. Various modifications obvious to one skilled in the art to which the present invention pertains are within the spirit, scope and contemplation of the present invention as further defined in the appended claims.

DEFINITIONS

A "bone morphogenetic protein-2 activity inhibitor" is a composition that antagonizes the activity of the BMP-2 protein by specifically binding to it or to BMP receptors, blocks the activation of pro-BMP-2, prevents the replication or transcription of the BMP-2 gene, or the translation of BMP-2 mRNA into protein.

"Polypeptide" refers to any peptide or protein comprising two or more amino acids joined to each other by peptide bonds or modified peptide bonds. Polypeptide refers to both short chains, commonly referred to as peptides, oligopeptides or oligomers, and to longer chains, generally referred to as proteins. Polypeptides include amino acid sequences modified either by natural processes, such as posttranslational processing, or by chemical modification techniques that are well known in the art. Such modifications are well-described in basic texts and in more detailed monographs, as well as in a voluminous research literature.

An "expression vector" is a recombinant vector that incorporates the desired gene and associated control sequences that promote and/or regulate expression of the gene. The desired gene is "operably linked" to such control sequences. The term "operably linked" means that the regulatory sequences necessary for expression of the coding sequence are placed in an appropriate position in the expression vector relative to the coding sequence so as to enable expression of the coding sequence. The preparation of such recombinant expression vectors as well as the use of various control sequences is well known to those of skill in the art and described in many references. See, for example, Sambrook, J., et al., *Molecular Cloning: A Laboratory Manual* 2nd ed. (Cold Spring Harbor, N.Y., Cold Spring Harbor Laboratory) (1989).

A "selective promoter" refers to a promoter that is not indiscriminately expressed. Instead, it may only be expressed in certain tissues, certain tumors, in response to certain treatments, or in response to certain events in a cell. Such tissue specific, tumor-selective, treatment-responsive, or tumor endothelium directed promoters are described in Nettlebeck, D. M., et al., "Gene therapy: designer promoters for tumour targeting" *Trends Genet* 16(4); 174-81 (2000).

An "expression vector vehicle" refers to an expression vector paired with a moiety that facilitates delivery of the expression construct to cells in vivo. An expression vector may incorporate genes encoding the delivery moiety. One example of such an expression vector is a viral vector.

The term "antibody" refers to polyclonal and monoclonal antibodies, chimeric, single chain, and humanized antibodies, as well as Fab fragments, including the products of a Fab or other immunoglobulin expression library.

"Polyclonal" refers to antibodies that are heterogeneous populations of antibody molecules derived from the sera of animals immunized with an antigen or antigenic functional derivative thereof. For the production of polyclonal antibodies, various host animals may be immunized by injection with the antigen. Various adjuvants may be used to increase the immunological response, especially when using an entire protein, or a larger section of the protein. The type of adjuvant used will depend on the hosts. Typical adjuvants include Fruend's, Fruend's complete, or oil-in-water emulsions. In these cases, the entire protein or portion thereof can serve as the antigen. When a smaller peptide is utilized, it is advantageous to conjugate the peptide with a larger molecule to make an immunostimulatory conjugate for use as the antigen. Commonly utilized conjugate proteins that are commercially available for such use include bovine serum albumin (BSA) and keyhole limpet hemocyanin (KLH).

"Monoclonal antibodies" are substantially homogeneous populations of antibodies to a particular antigen. They may be obtained by any technique that provides for the production of antibody molecules by continuous cell lines in culture. Such methods are well known to those of ordinary skill in the art and include general hybridoma methods of Kohler and Milstein, *Nature* (1975) 256: 495-497, the trioma technique, the human B-cell hybridoma technique (Kozbor et al., *Immunology Today* 4:72 (1983) and the EBV-hybridoma technique (Cole et al., *Monoclonal Antibodies and Cancer Therapy*, pp. 77-96, Alan R. Liss, Inc. (1985). The basic technique involves injecting a mouse, or other suitable animal, with an antigen. The animal is subsequently sacrificed and cells taken from its spleen are fused with myeloma cells. The result is a hybrid cell, referred to as a hybridoma, which reproduces in vitro. The population of hybridomas is screened to isolate individual clones, each of which secretes a single antibody species to the antigen. The individual antibody species obtained in this way are each the product of a single B cell from the immune animal generated in response to a specific antigenic site recognized on the antigen. Kohler, G. and Milstein, C. *Nature* (London) 256: 495-497 (1975) and *Eur. J. Immunol.* 6: 511-519 (1976).

The term "antibody fragment" refers to a portion of an antibody, often the hyper variable region and portions of the surrounding heavy and light chains, that displays specific binding affinity for a particular molecule. The term antibody fragment also includes single chain antibodies.

An "antisense oligonucleotide" is an oligonucleotide that specifically hybridizes, under cellular conditions, with the cellular mRNA or genomic DNA encoding a BMP-2 protein or some portion of such cellular or genomic DNA, thereby inhibiting: biosynthesis of the BMP-2 protein. The binding may be via conventional base pair complementarity, or, in the case of binding to DNA duplexes, via specific interactions in the major groove of the double helix.

The term "effective amount" refers to the quantity of a compound that is sufficient to yield a desired therapeutic response without undue adverse side effects (such as toxicity, irritation, or allergic response) commensurate with a reasonable benefit/risk ratio when used in the manner of this invention. The specific "effective amount" will obviously vary with such factors as the particular cancer being treated, the physical condition of the patient, the type of mammal being treated, the duration of the treatment, the nature of any concurrent therapy, the specific formulations employed, and the structure of the compounds or their derivatives.

A "patient" is a mammal suspected of having cancer. The patient is preferably human but may also be another mammal, such as a cat, dog, horse, cow, rat, or mouse.

A "biological sample" is a substance obtained from the patient's body. The particular "biological sample" selected will vary based on the purpose and/or assay for which the sample is obtained. For example, if a patient is suspected or known to have cancer, the sample will be the substance most likely to contain cancer. If the sample is taken from a person without cancer, the sample will likely be the same substance that is taken from a patient as a basis for comparison. An "elevated level" means the level of bone morphogenetic protein-2 that is greater than the level of analyte present in a particular biological sample of patient that is not suffering from cancer.

A "carcinoma" is an epithelial cancer. Examples of carcinomas are bladder cancer, breast cancer, colon cancer, kidney cancer, lung cancer, ovarian cancer, thyroid cancer, endometrial cancer, omental cancer, testicular cancer, and liver cancer. The epithelium predominately lines ducts and lining of organs or glands.

BMP-2 as a Target in the Treatment of Cancer

The present invention is directed to the use of BMP-2 as a target in the treatment of cancer. Amino acids #283-396 of SEQ ID NO: 2 constitute the amino acid sequence of mature human BMP-2. Nucleotides #372-1514 of SEQ ID NO: 1 constitute the nucleotide coding sequence for human BMP-2. Any composition that specifically binds BMP-2 or a BMP-2 receptor, thereby antagonizing BMP-2 activity, blocks the processing of pro-BMP-2, and/or prevents the replication or transcription of BMP-2 DNA or the translation of BMP-2 mRNA could be used as a therapy to treat cancer.

A compound that specifically binds to BMP-2 is any compound such as a polypeptide or an antibody that has a binding affinity for any naturally occurring isoform, splice variant, or polymorphism of BMP-2. As one of ordinary skill in the art will appreciate, such "specific" binding compounds may also bind to other closely related proteins that exhibit significant homology (such as greater than 90% identity, more preferably greater than 95% identity, and most preferably greater than 99% identity) with the amino acid sequence of BMP-2. Any compound that binds to BMP-2 sufficiently to suppress BMP-2 activity is contemplated by the present invention.

Similarly, a compound that specifically binds to a BMP receptor is any compound that has a binding affinity for any naturally occurring isoform, splice variant, or polymorphism of the BMP receptor. As one of ordinary skill in the art will appreciate, such "specific" binding compounds may also bind to other closely related proteins that exhibit significant homology (such as greater than 90% identity, more preferably greater than 95% identity, and most preferably greater than 99% identity) with the amino acid sequence of a BMP receptor. The present invention embodies polypeptides that specifically bind to BMP-2, thereby inhibiting its activity, or that specifically bind to BMP receptors, thereby inhibiting BMP-2 activity. Specific embodiments of such polypeptides are described below.

The present invention encompasses known antagonists of BMP-2 activity, including noggin (35) (U.S. Pat. No. 6,075,007, Economides, et al.), chordin (36) (U.S. Pat. No. 5,896,056), gremlin (GENBANK Accession No. AF 154054), cerberus 1 homolog (GENBANK Accession No. NM-005454), and DAN.

Recombinant mouse noggin from R & D Systems (Minneapolis, Minn.) was used in the inhibition experiments described in the Results section below. Mouse and human noggin share 98% homology. Therefore, this invention also relates to use of a polypeptide with the amino acid sequence of mature mouse noggin (amino acids #20-231 of SEQ ID NO: 6) and with the amino acid sequence of mature human noggin (amino acids #20-231 of SEQ ID NO: 4) as a BMP-2 activity inhibitor. The amino acid sequence for human chordin is SEQ ID NO: 8, for human gremlin is SEQ ID NO: 10, and for cerberus 1 homolog is SEQ ID NO; 12. The nucleotide coding sequence for human noggin is SEQ ID NO: 3, for mouse noggin is SEQ ID NO: 5, for human chordin is nucleotides #247-3114 of SEQ ID NO: 7, for human gremlin is nucleotides #130-684 of SEQ ID NO: 9, for human cerberus 1 homolog is SEQ ID NO: 11.

This invention also embodies polypeptide fragments of noggin, chordin, gremlin, cerberus 1 homolog, and DAN that bind BMP-2 and inhibit its activity. Such polypeptides may be tested for inhibitory efficiency by culturing cells transformed with progressively shorter portions of the nucleotide sequences encoding the above proteins, recovering and purifying from the various cultures the resulting polypeptide, and testing those polypeptides for their ability to inhibit BMP-2 activity.

This invention also includes genetically altered BMP receptor proteins that inhibit BMP-2 activity. For example, altered BMP receptors that inhibit the binding effects of BMP-2 are described in U.S. Pat. No. 6,291,206 (Wozney, et al.).

Also included by this invention are polypeptides that bind BMP receptors without activating them. (37, 38) Particularly preferred are ligands that will bind BMP IB receptors, which are a subtype of BMP receptors. Aberrant expression of the BMP IB receptor in many human cancer specimens has been noted, as discussed in the Results section below. (39) The coding sequence for BMP IB precursor is nucleotides #274-1782 of SEQ ID NO: 13. The amino acid sequence for BMP IB is amino acids #14-502 of SEQ ID NO: 14.

This invention also encompasses expression vectors that incorporate a nucleotide sequence encoding an inhibitor of BMP-2 activity operably linked to control sequences that promote and/or regulate expression of the nucleotide sequence. The preparation of such expression vectors, as well as the use of various control sequences, is well known to those of skill in the art and is described in many references, such as Sambrook, et al. (1989). Expression vectors can be derived from bacterial plasmids, from bacteriophages, from transposons, from yeast episomes, from insertion elements, from yeast chromosomal elements, from viruses and from combinations thereof, such as those derived from plasmid and bacteriophage genetic elements, such as cosmids and phagemids. Promoters can be prokaryotic, such as lacI, lacZ, T3, T7, gpt, lambda PR, PL, and trp, or eukaryotic, such as CMV immediate early, HSV thymidine kinase, early and late SV40, LTR's from retrovirus, and mouse metallothionein-1. Selective promoters such as those described in Nettlebeck, D. M., et al., "Gene therapy: designer promoters for tumour targeting" Trends Genet 16(4); 174-81 (2000) that are tissue-specific, tumor-selective, treatment-responsive, or tumor endothelium directed may also be used. For example, the promoter of the carcinoembryonic antigen (CEA) is expressed on many breast, lung, and colorectal cancers.

For introduction of a gene that encodes a protein that antagonizes BMP-2 activity, an expression vector vehicle that will facilitate delivery of the desired gene to the affected cells may be used. One way to facilitate delivery is by using an expression vector derived from virus. Examples of viral vectors that have been successfully used to deliver desired sequences to cells with high infection efficiency are adenoviral, retrovital, vaccinia viral, and adeno-associated viral vectors. Commonly used viral promoters for expression vectors are derived from polyoma, cytomegalovirus, Adenovirus, and Simian Virus 40 (SV40). It is also possible to use promoter or control sequences normally associated with the desired gene sequence, if such control sequences are compatible with the host cell systems.

Non-viral expression vector vehicles are also available. For instance, the expression vector could be associated with one or more lipids. As is known in the art of lipid-based gene delivery, such nucleic acid-lipid complexes can be in a variety of different forms depending generally on the nature of the lipid employed, the ratio of nucleic acid to lipid and/or other possible components, and the method by which the complex is formed. Examples of complexes include liposomes and micelles. Liposome-mediated gene transfer seems to have great potential for certain in vivo applications in animals. Studies have shown that intravenously injected liposomes are taken up essentially in the liver and the spleen, by the macrophages of the reticuloendothelial system. Using a catheter to introduce liposomes coupled to expression vectors to particular cellular sites has also been described. (Nabel, E. G., et al., Science 249:1285-1288 (1990))

Another possible expression vector vehicle consists of a cell receptor-specific ligand and a DNA-binding agent that would bind to the expression vector. (Nishikawa, M. et al., Gene Therapy 7:548-55 (2000)). Such a vehicle could also comprise a cell receptor-specific ligand and the nucleic acid-lipid complex described above. (Nicolau, C. et al., Methods Enzymol 149: 157-76 (1987))

In addition, the present invention embodies antibodies that specifically bind BMP-2 or BMP receptors, thereby inhibiting BMP-2 activity. When raising antibodies to BMP-2 or BMP receptors, the entire protein (either the precursor or the processed protein), or a portion thereof, may be utilized. Information useful in designing an antigen for the production of antibodies to BMP-2 may be deduced by those of skill in the art by homology analysis of SEQ ID NO: 2, especially amino acids #283-396 of SEQ ID NO: 2.

A recombinant human BMP-2 protein is commercially available from R & D Systems (Minneapolis, Minn.) and portions of the BMP-2 protein may be produced by a variety of methods. In order to raise antibodies to particular epitopes, peptides derived from the full BMP-2 sequence may be used. Custom-synthesized peptides in the range of 10-20 amino acids are available from a multitude of vendors, and can be ordered conjugated to KLH or BSA. Alternatively, peptides in excess of 30 amino acids may be synthesized by solid-phase methods, or may be recombinantly produced in a recombinant protein production system. In order to ensure proper protein glycosylation and processing an animal cell system (e.g., Sf9 or other insect cells, CHO or other mammalian cells) is preferred.

Selection of antibodies which alter the activity of BMP-2 may be accomplished in several ways. Antibodies that alter the binding of BMP-2 to a receptor may be detected by well-known binding inhibition assays. For instance, according to standard techniques, the binding of a labeled (e.g., fluorescently or enzyme-labeled) antibody to BMP-2, which has been immobilized in a microtiter well, is assayed for BMP-2 binding in both the presence and absence of the appropriate receptor. The decrease in binding will be indicative of a competitive inhibitor relationship between the antibody and the receptor. In addition, antibodies that are useful for altering the function of BMP-2 may be assayed in functional formats, such as the cell migration assays described in the Results and Examples sections.

This invention also embodies compositions that prevent the processing of inactive BMP-2 precursors. BMP precursors are proteolytically activated by proprotein convertases. For example, BMP-2 is cleaved by furin convertase from human leukocytes Furin inhibitors are known. (40) While the BMP-2 inhibitors discussed above adversely affect BMP-2 activity after it is expressed, it will be readily apparent to one of ordinary skill in the art that specific prevention of BMP-2 biosynthesis will achieve the same goals as more direct inhibition of its activity. Consequently, this invention also encompasses inhibition of BMP-2 biosynthesis as a method for treating cancer. Such inhibition may be achieved by selectively degrading mRNA encoding BMP-2 or BMP-4 or by interfering with transcription or translation of such mRNA. (41) As mentioned above, BMP-2 shares 92% homology with BMP-4.

Inhibition of BMP-2 biosynthesis to treat for cancer could also be achieved through antisense therapy. Antisense therapy is the administration or in situ generation of oligonucleotides that specifically hybridize, under cellular conditions, with the cellular mRNA or genomic DNA encoding a BMP-2 protein or some portion of such cellular or genomic DNA, thereby inhibiting biosynthesis of the BMP-2 protein. Antisense therapy refers generally to the range of techniques known by one of ordinary skill in the art, and includes any therapy that relies on specific binding to oligonucleotide sequences.

Delivery of an antisense oligonucleotide of the present invention can occur in a variety of ways. For example, an antisense oligonucleotide can be delivered as an expression vector that produces RNA, which is complementary to at least a unique portion of the cellular mRNA encoding BMP-2. Such an expression vector could be delivered to cells by one of the expression vector vehicles described above. Alternatively, the antisense oligonucleotide could be generated ex vivo as an oligonucleotide probe which, when introduced to the cell, inhibits biosynthesis of BMP-2 proteins by hybridizing with the mRNA or genomic sequences encoding BMP-2. Such oligonucleotide probes could be modified oligonucleotides that are resistant to endogenous nucleases and therefore are stable in vivo. General methods to construct oligomers useful in antisense therapy are known in the art. (Van der krol, et al., Biotechniques 6:958-976 (1988); Stein, et al., Cancer Res. 48:2659-2668 (1988).

Dosage forms of the BMP-2 inhibitors of this invention include pharmaceutically acceptable carriers known to those of ordinary skill in the art. Pharmaceutically acceptable components are those that are suitable for use with mammals without undue adverse side effects (such as toxicity, irritation, and allergic response) commensurate with a reasonable benefit/risk ratio. The carrier can be a solid or liquid. The type of carrier is generally chosen based on the type of administration being used. The active agent can be co-administered in the form of a tablet or capsule, as an agglomerated powder or in a liquid form. Examples of suitable solid carriers include lactose, sucrose, gelatin and agar. Capsule or tablets can be easily formulated and can be made easy to swallow or chew; other solid forms include granules and bulk powders. Tablets may contain suitable binders, lubricants, diluents, disintegrating agents, coloring agents, flavoring agents, flow-inducing agents and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspension reconstituted from non-effervescent preparations reconstituted from effervescent granules. Such liquid dosage forms may contain, for example, suitable solvents, preservatives, emulsifying agents, suspending agents, diluents, sweeteners, thickeners and melting agents. Parenteral and intravenous forms may also include isotonic salts and other materials to make them compatible with the type of injection or delivery system chosen.

For administration of an antibody to BMP-2, the pharmaceutically acceptable carrier will usually be an aqueous solution, such as normal saline or phosphate-buffered saline (PBS), Ringer's solution, lactate-Ringer's solution, or any isotonic physiologically acceptable solution for administration by the chosen means. In addition to additives for adjusting pH or tonicity, the antibody may be stabilized against aggregation and polymerization with amino acids and non-ionic detergents, polysorbate, and polyethylene glycol. Optionally, additional stabilizers may include various physiologically acceptable carbohydrates and salts. In addition, polyvinylpyrrolidone may be added in addition to the amino acid. Suitable therapeutic immunoglobulin solutions, which are stabilized for storage and administration to humans are described in U.S. Pat. No. 5,945,098. Other agents, such as human serum albumin (HSA), may be added to the pharmaceutical composition to stabilize the antibody conjugates.

The method of administration can be any suitable method that effectively alleviates the particular tumor and/or cancer being treated. Possible methods of administration are oral, rectal, parenteral, enteric, subcutaneous, transdermal, peritoneal, intratumoral, or intravenous.

Any suitable dosage of the compounds may be given in the method of the invention. Dosage levels and requirements are well recognized by those of ordinary skill in the art. As one of ordinary skill in the art will appreciate, an amount constituting an effective amount will vary depending on particular factors. For instance, specific dosage and treatment regimens will depend on facts such as the patient's general health profile, the type of cancer being treated, the severity and course of the patient's disorder, other therapeutics being administered to treat the cancer, and the judgment of the treating physician.

The present invention also provides kits for treating cancer using BMP-2 activity inhibitors. For example, such kits can comprise any one or more of the following materials: packaging material, at least one type of BMP-2 activity inhibitor, and instructions regarding dosage, method of administration, or the like for using the inhibitor to treat cancer.

Detection of BMP-2 to Aid in Diagnosis of Cancer

In addition to its therapeutic aspects, the present invention also relates to a diagnostic method for detecting the presence of elevated levels of BMP-2 in the patient. The inventor has shown that BMP-2 is expressed in many common cancers. Elevated levels of BMP-2 can be detected in various biological samples in mammals, preferably humans. The inventor has further shown the presence of BMP-2 in the blood serum of a human patient with cancer. Biological samples, including but not limited to blood, vitreous humor, sputum, aqueous humor, synovial fluid, urine, ascites, and tissue, will be drawn from the patient using standard techniques. Particularly preferred are serum samples.

The measurement of BMP-2 levels may be monitored using any method possible to detect BMP-2 in biological samples. Immunoassays, such as Enzyme Linked Immunological Assay (ELISA), Western blots, immunoprecipitation, in situ immunohistochemistry, and immunofluorescence assays are preferred. ELISA is particularly preferred. For a review of general immunoassays, see Stites, D. P., et al., eds., Basic and Clinical Immunology, 8th ed. (Appleton & Lange, Norwalk, Conn.) (1994). Immunological binding assays (or immunoassays) typically use an antibody that specifically binds to a protein of choice, BMP-2, in this case. The antibody is generally fixed to a substrate such as a plate or a column via covalent or non-covalent linkages (e.g., streptavidin, protein A, protein G, secondary antibodies). Immunoassays also often use a labeling agent to specifically bind to and label the complex formed by the antibody and antigen. The labeling agent may be a labeled anti-BMP-2 antibody. Alternatively, the labeling agent may be a third moiety, such as a secondary antibody, that specifically binds to the antibody/antigen complex.

The immunoassays of this invention may be competitive or noncompetitive. Noncompetitive immunoassays are assays in which the amount of antigen is directly measured. In a "sandwich" assay, for example, the anti-BMP-2 antibodies can be bound directly to a solid substrate on which they are immobilized. These immobilized antibodies then capture BMP-2 in the test sample. BMP-2 thus immobilized is then bound by a labeling agent, such as a second antibody bearing a label. Alternatively, the second antibody may lack a label, but it may be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety. Methods of binding molecules to a solid support, either covalently or non-covalently, are well known to those of skill in the art. A variety of solid supports known to those of skill in the art, e.g., plate, columns, dipsticks, membranes, and the like, can be used with the present invention.

In competitive assays, the amount of BMP-2 is measured indirectly by measuring the amount of a known modified BMP-2 displaced from a BMP-2 antibody by the unknown BMP-2 in a sample. In one competitive assay, a known amount of modified BMP-2 is added to a sample and the sample is then contacted with an anti-BMP-2 antibody. The amount of known modified BMP-2 bound to the antibody is inversely proportional to the concentration of BMP-2 in the sample. The amount of modified BMP-2 may be detected by providing a labeled modified BMP-2 molecule.

The label used in the assay is not a critical aspect of the invention, so long as it does not significantly interfere with the specific binding antibody used in the assay. The detectable group can be any material having a detectable physical or chemical property. Thus, a label is any composition detectable by spectroscopic, photochemical, biochemical, immunochemical, electrical, optical, or chemical means. Examples of such labels are magnetic beads, fluorescent dyes, radiolabels, enzymes, and calorimetric labels such as colloidal gold or colored glass or plastic beads.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions. Non-radioactive labels are often attached by indirect means. Generally, a ligand molecule, such as biotin, is covalently bound to the molecule. The ligand then binds to another molecule, such as streptavidin, which is either inherently detectable or covalently bound to a signal system, such as a detectable enzyme, a fluorescent compound, or a chemiluminescent compound. The ligands and their targets can be used in any suitable combination with antibodies that recognize BMP-2. The molecules can also be conjugated directly to a signal-generating compound, e.g., by conjugation with an enzyme or fluorophore.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers or the like. Similarly, enzymatic labels may be detected by providing the appropriate substrates for the enzyme and detecting the resulting reaction product. Finally, simple colorimetric labels may be detected simply by observing the color associated with the label.

Some assay formats do not require the use of labeled components. For instance, agglutination assays can be used to detect the presence of the target antibodies.

RESULTS

Experimental results supporting the above uses of BMP-2 and its inhibitors are set forth in detail below. All of the experimental methods mentioned in this section, such as representational difference analysis, Western blot assays, and immunohistochemical studies, are described in detail in the Examples section that follows.

Identification of BMP-2 Using RDA Subtraction Technique

Initially, the inventor performed representational difference analysis (RDA) on cDNA derived from normal and cancerous lung tissue samples to identify genes that were uniquely or highly expressed in human lung cancer in comparison to normal tissue. [FIG. 1(a)] RDA has been described in the literature and allows detection of differences in gene expression between two similar populations. It involves exposing digested tester cDNA ligated to a primer to high concentrations of similarly digested but non-primer bearing driver cDNA, melting the tester and driver cDNA, and allowing them to hybridize.

Subsequent PCR results in exponential amplification of the target cDNA of the tester that hybridizes to other tester cDNA. (Hubank, M., *Nucleic Acids Research* 22:5640-5648 (1994)) Here, a non-small cell lung carcinoma (NSCLC) as the tester and immortalized human bronchial epithelial (IHBE) cells were used as the driver. IHBE cells rather than normal lung tissue were used, as IHBE cells proliferate at a rate that is more similar to human lung carcinomas than to normal lung tissue. Thus, this technique avoided identifying genes involved in the proliferation cascade but that were not by themselves transforming.

After two rounds of subtraction, several distinct bands, which were cloned and sequenced, were present in the amplified tester cDNA. [FIG. 1(b)] A BLAST database search identified BMP-2 expression in the lung tumor tissue specimen as well as expression of alpha-1-antitrypsin, cytokeratin 6, and lambda light. [(FIG. 1(c)]

Expression of BMP-2 in Various Cancer Tissue Specimens, Cancer Cell Lines, and Blood Serum from a Cancer Patient Using reverse transcriptase polymerase chain reaction (RT-PCR), Western blots, and immunohistochemical assays to study the expression of BMP-2 and its receptors in various tissue specimens and in cell lines, it was discovered that BMP-2 was highly expressed in many types of cancers.

Figure 2:
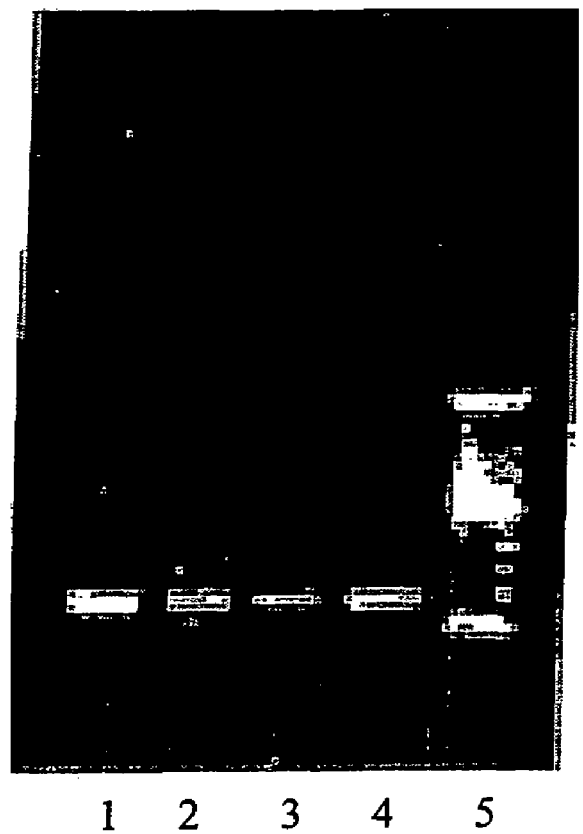
FIG. 2 is an ethidium-stained agarose gel showing the results of RT-PCR performed on human lung cancer specimens. Lanes 1-4 contain the results of the RT-PCR of various specimens, while lane 5 contains a marker.
Figure 3:
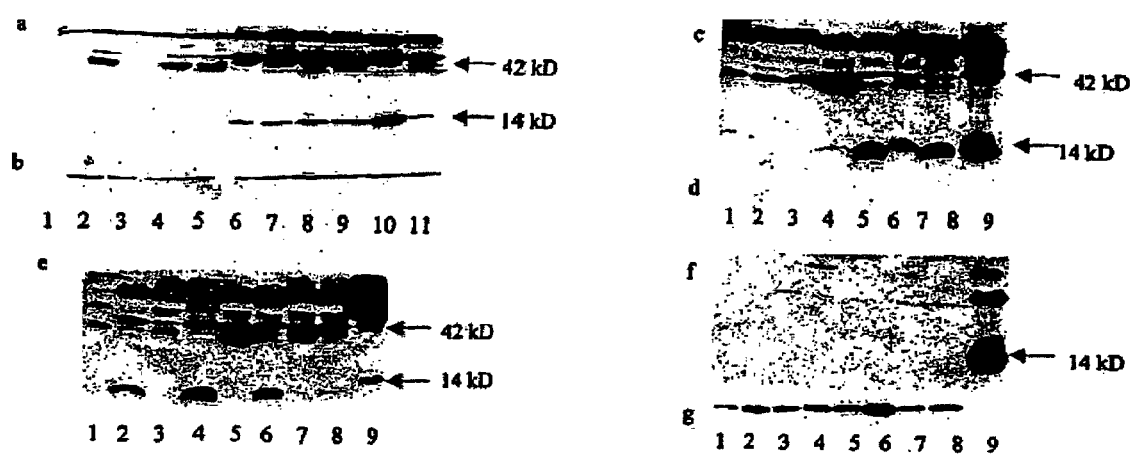
FIG. 3 illustrates Western blots showing mature BMP-2 overexpressed in lung cancer tissue specimens and lung cancer cell lines.

The initial experiments were performed on normal and cancerous lung tissue and lung cancer cell lines. RT-PCR was performed using BMP-2 primers and showed expression of BMP-2 in 9 out of 10 tumors examined. [FIG. 2] Using Western blot analysis, the inventor found that the mature active 14 kD BMP-2 protein was aberrantly expressed in almost all of the 25 non-small cell lung carcinoma (NSCLC) tissue specimens examined. There was little to no expression of BMP-2 in 11 normal lung tissue specimens. A representative Western blot from that experiment is shown in FIG. 3. An anti-actin immunoblot showed near equal loading of the samples, which further confirms the validity of the experiment. [FIG. 3(b)] In addition, BMP-2 was found to be highly expressed in all epithelial derived lung carcinomas of which NSCLC is derived and in the rare malignant neuroendocrine tumor. [FIG. 3(c) and FIG. 3(e), Lane 4, respectively]

Western blot analysis of each of the different cell types comprising NSCLC—adeno, squamous, large cell, and bronchoalveolar carcinomas—revealed that the level of BMP-2 expression was not dependent on the cell type or whether the tumor was well or poorly differentiated. In comparison, the level of BMP-2 expression in benign lung tumors [FIG. 3(e), Lane 1] and inflammatory diseases of the lung [FIG. 3(a), Lane 6] was very low, similar to that seen in normal lung tissue, showing that BMP-2 is not an acute phase protein and that high levels of BMP-2 expression are indicative of malignant tumors. Neither BMP-4 nor BMP-7 expression was detected in the lung tissue specimens or the A549, H7249, IHB, and NBE cell lines by Western analysis. [FIG. 3(f)]

Figure 4:
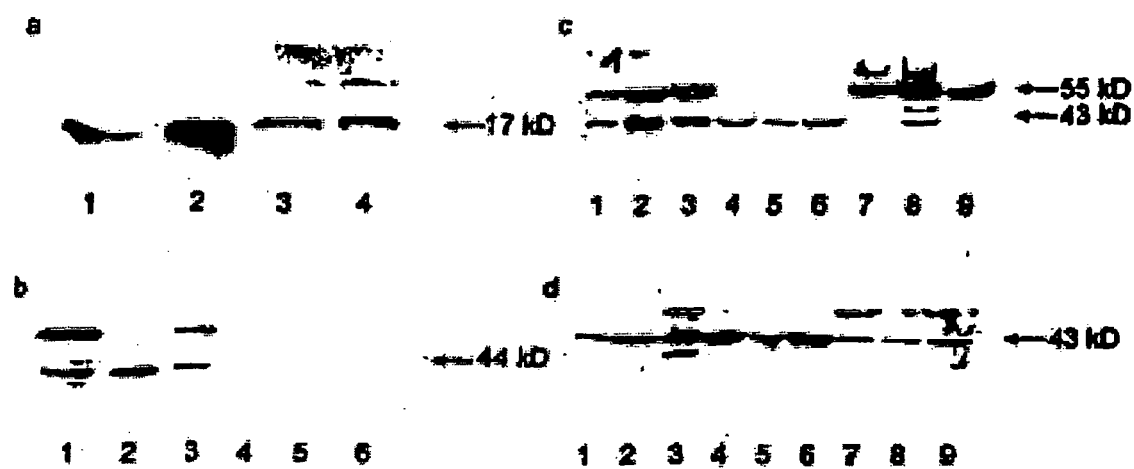
FIG. 4(a) is a Western immunoblot of total cellular protein that demonstrates that normal and malignant human lung cell lines express mature BMP-2 protein. Lanes (1) IHBE; (2) SOAS; (3) H7249; (4) A549.
FIG. 4(b) is a Western blot of cell culture media showing lung cancer cell lines secrete a BMP-2 precursor protein. The lanes are: (1) lung cancer tumor specimen; (2) A549 media; (3) H7249 media; (4) IHBE; (5), NBE media; (6) serum free media alone.
FIG. 4(c) is an immunoblot of BMP type IA receptor. Lanes (1-3) normal lung tissue specimens; (4) IHBE cells; (5) H7249 cells; (6) A549 cells; (7-9) lung cancer tissue specimens.
FIG. 4(d) is an immunoblot of BMP type 1B receptor. (1-3) normal lung tissue specimens; (4) IHBE cells; (5) H7249 cells; (6) A549 cells; (7-9) lung cancer tissue specimens.

Tests were also performed to determine whether there was expression of BMP-2 in various lung cancer and normal cell lines. Although the mature BMP-2 protein was detected in the cell lysate of the A549 and H7249 human lung cancer cell lines, the level of expression was not significantly different from the level of expression in the cell lysate of immortalized normal human bronchial epithelial cells (IHBE). [FIG. 4(a)] Because BMP-2 is a secreted protein, its expression in the cell culture media was also examined. A Western blot of the cell culture media showed the A549 and H7249 cell lines secreted a 43 kD BMP-2 precursor protein. [FIG. 4(b), Lanes 2-3] This BMP-2 precursor was not detected in the media from either the IHBE or normal bronchial epithelial (NBE) cells. FIG. 4(b), Lanes 4-5]

Figure 5:
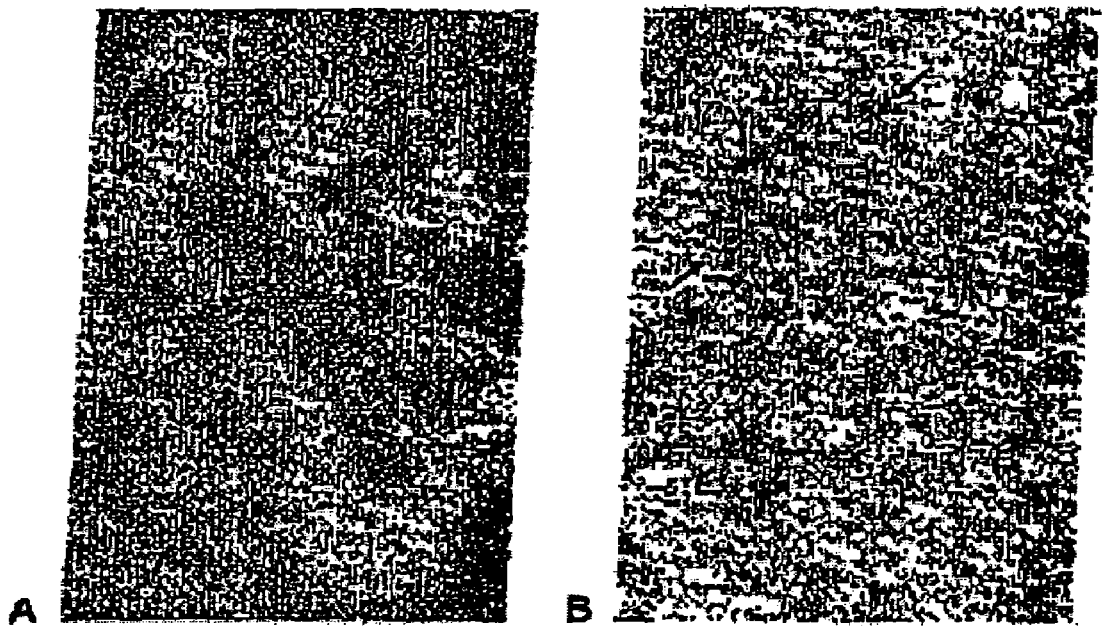
FIG. 5(a) is an immunohistochemistry localizing BMP-2 expression to the tumor cells. BMP-2 expression in a NSCLC demonstrating cytoplasmic staining of the tumor cells (arrowheads). The nuclei (n) of the tumor cells and the interstitium (I) are non-reactive.
FIG. 5(b) shows preabsorption of the BMP-2 antibody with recombinant human BMP-2 is non-reactive with the tumor cells (arrows). Original magnification is 82×.

Immunohistochemistry studies of patient derived NSCLC also localized the expression of BMP-2 to the cancer cells. [FIG. 5(a)] Absorbing the anti-BMP-2 antibody with recombinant human BMP-2 completely inhibited staining of the tumors. [FIG. 5(b)] BMP-2 expression was not detected in normal lung tissue by immunohistochemistry.

Expression of 1A and 1B BMP Receptors

Next, the inventor found that normal and cancer lung tissue specimens and cell lines express both type IA and IB BMP receptors. The lung cancer and normal lung tissue specimens express a 55 kD and 44 kD type IA BMP-2 receptor. The tumor specimens expressed predominately the 55 kD receptor, while normal lung tissue specimens expressed a higher percentage of the 44 kD receptor. The A549, H7249, and. IHBE cells only expressed a 44 kD type IA BMP receptor. [FIG. 4(c)] The tissue specimens and cell lines expressed a 44 kD type IB BMP receptor with normal lung tissue demonstrating more expression than that of the tumor specimens. [FIG. 4(d)]

BMP Overexpression in Many Types of Cancerous Tissue

Figure 6:
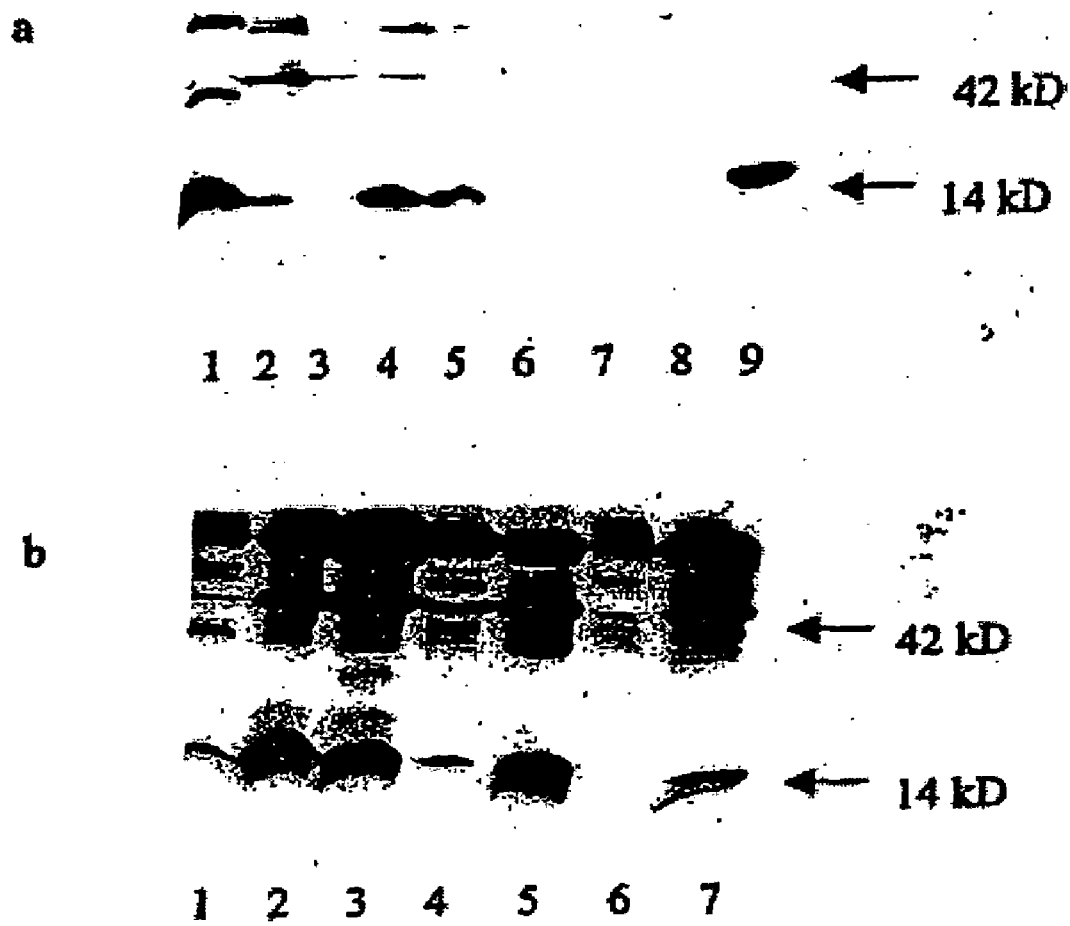
FIG. 6(a) is a BMP-2 Western blot of human breast tumors and corresponding normal tissue. Lane 1: NSCLC, lanes 2-5: breast carcinomas, lanes 6-8: normal breast tissue, lane 9: recombinant BMP-2.
FIG. 6(b) is a BMP-2 Western blot of common human carcinomas and the corresponding normal tissue. Lane 1: normal endometrium, lane 2: endometrial carcinoma, lane 3: ovarian carcinoma, lane 4: normal colon, lane 5: colon carcinoma, lane 6: normal bladder, lane 7: bladder carcinoma.

Similar to the findings with lung tissue, it was found that BMP-2 was expressed in many other common human malignancies but not in their corresponding normal tissues. Western blot analysis revealed that BMP-2 was overexpressed in breast, bladder colon, endometrial, omental, and kidney carcinomas with low levels of BMP-2 expression in the corresponding normal tissue. [FIGS. 6(a) and (b)] BMP-2 was also found to be expressed in ovarian [FIG. 6(b), lane 3], mesothelioma [FIG. 6(e), lane 2], thyroid, hepatoma, and testicular carcinoma.

Figure 7:
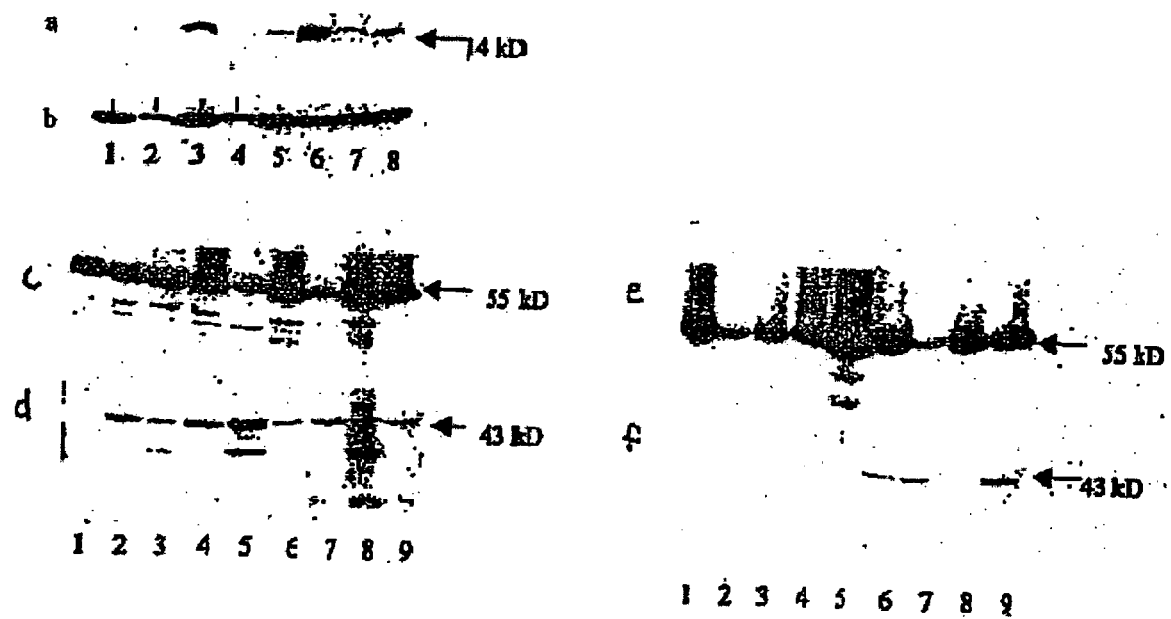
Figure 8:
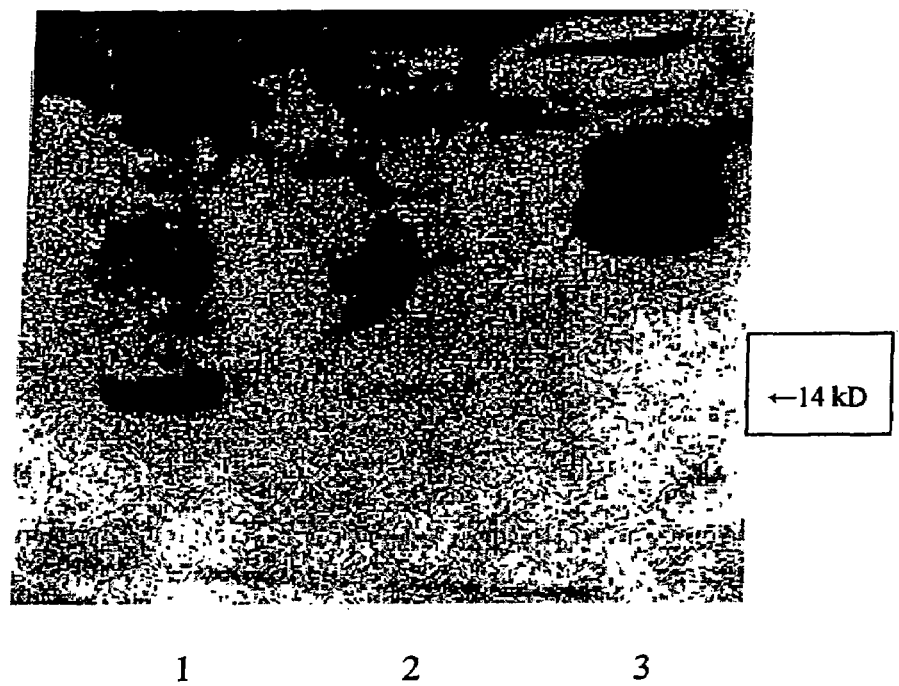
FIG. 8 is a Western blot showing BMP-2 in serum samples from lung cancer patients. Lanes 1-2: serum samples, lane 3: recombinant BMP-2. 14 kD is the size of mature BMP-2.

BMP-2 and its receptors were also examined in both primary and metastatic carcinomas that were surgically removed from patients. BMP-2 was found to be highly expressed in kidney tumors that had metastasized to the lung, a metastatic breast cancer to chest wall cavity, and a NSCLC lung tumor that had metastasized to a regional lymph node. [FIG. 7(a)] The BMP IA receptor was expressed equally between the primary and metastatic carcinomas and the corresponding normal tissue. [FIG. 7] The BMP IB receptor was expressed in all metastatic and primary tumors examined. [FIG. 7] The BMP IB receptor, in contrast to the BMP IA receptor, was not expressed in all the corresponding normal tissues. While it was expressed in normal lung tissue with slight expression in normal endometrium, it was not expressed in normal kidney, colon, and omentum. [FIG. 7(f)] Interestingly, the IB receptor was expressed in both primary and metastatic renal carcinoma, but not in normal kidney tissue. [FIG. 7(f), Lane 6] BMP-2 expression was also found in blood serum samples from lung cancer patients. [FIG. 8]

Processing of Inactive BMP-2 Precursors

Figure 9:
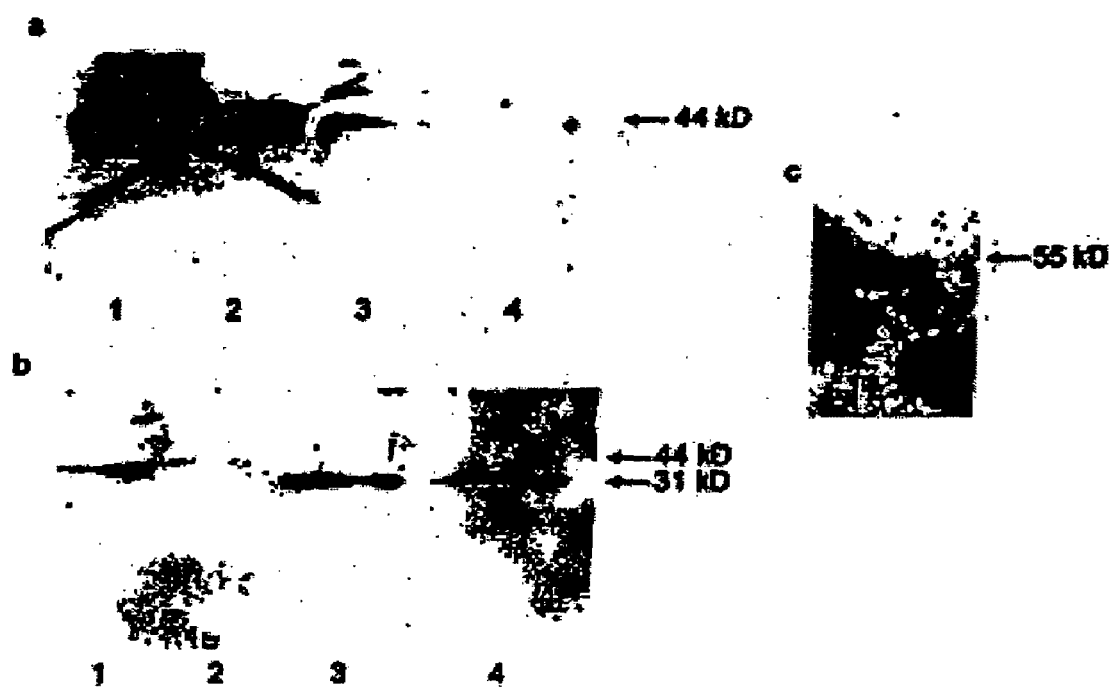
FIG. 9 shows that secreted BMP-2 precursor is proteolytically cleaved by human leukocytes. Cell culture media from the A549 cells incubated with leukocytes for 16 hours is probed with BMP-2 antibody recognizing its mature C-terminal end.

Because BMP precursors are proteolytically activated by proprotein convertases, the inventor studied whether BMP-2 could be processed following secretion, hypothesizing that secreted BMP-2 precursors from tumor cells may be processed by cells present in the tumor stroma. Because leukocytes normally infiltrate the lung and because furin convertase is ubiquitously expressed, the ability of leukocytes to cleave proprotein BMP-2 secreted from A549 cells was examined. First, it was determined that the furin convertase is expressed in human leukocytes isolated from whole blood. [FIG. 9(c)] Human leukocytes were incubated with A549 cell culture media containing the BMP-2 precursor protein. A Western blot of the incubated media samples was probed with an anti-human BMP-2 precursor antibody that recognizes its C-terminal end. The 45 kD BMP-2 precursor protein was consistently decreased following incubation with the leukocytes. [FIG. 9(a)] By probing immunoblots with an anti-human BMP-2 antibody that recognizes its N-terminal end, the inventor identified a 31 kD BMP-2 product present only in the media samples incubated with leukocytes. [FIG. 9(b)] This data shows that BMP-2 precursor proteins are cleaved by human leukocytes.

Effect of BMP-2 on Tumors and Cancer Cell Lines

After determining that BMP-2 was highly expressed in most common cancers, the inventor performed experiments to show that BMP-2 causes cancer invasion and metastasis. The experiments were conducted with lung cancer cell lines and with nude mice injected with A549 cells.

Figure 10:
FIG. 10 shows that BMP-2 treatment enhances formation of blood vessels around a cancerous tumor. Each picture is of tissue from a nude mouse injected either with A549 cells or with A549 cells and BMP-2. The picture in the upper right shows a tumor and surrounding tissue from a nude mouse injected with A549 cells. Upper left: control. Upper right: mouse treated with BMP-2. Lower left: mouse treated with noggin.
Figure 11:
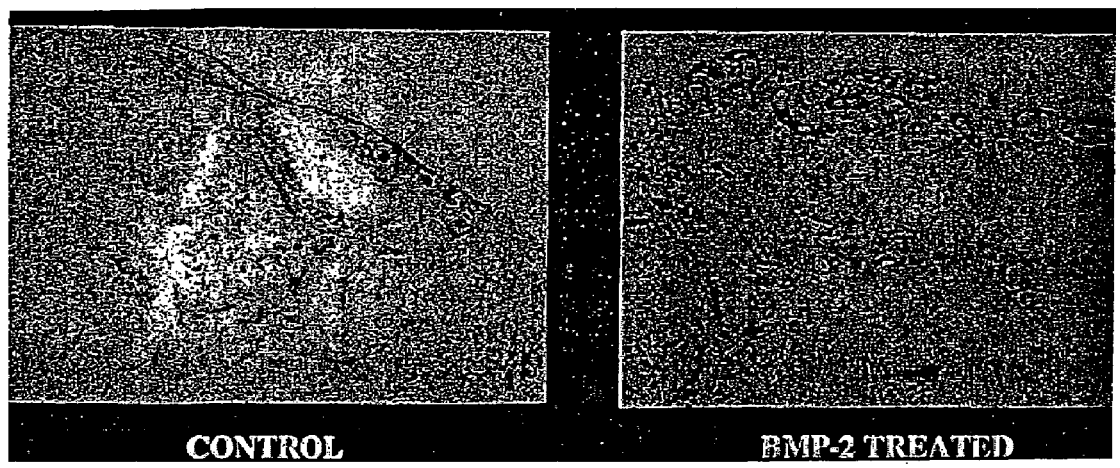
FIG. 11 shows tissue from nude mice injected with A549 cells and nude mice co-injected with A549 cells and BMP-2 stained with anti-CD 31 antibody, which recognizes endothelial cells, viewed from under a microscope.

The experiments with the nude mice showed that BMP-2 treatment enhances blood vessel formation around tumors from nude mice injected with A549 cells. Some of the mice were co-injected with BMP-2. Gross observations of tissue harvested after six days showed that the addition of recombinant BMP-2 to developing tumors in nude mice caused increased blood vessel formation. [FIG. 10] Tissue was also stained with anti-CD31 antibody which recognizes endothelial cells. A person blind to how the tumors were created then observed the tissue through a microscope and counted the number of vessels that had formed in the tumor. This data showed that BMP-2 caused a statistically significant increase in the number of blood vessels in the tumor. [FIG. 11]

Other studies showed that addition of BMP-2 to cancer cell lines increased expression of vascular endothelial growth factor (VEGF) and the oncogene Sonic Hedgehog. The addition of recombinant BMP-2 to human aortic endothelial cells in culture caused an increase in VEGF secretion as determined by ELISA performed on the cell culture media. The concentration of VEGF in the cell culture media before treatment with BMP-2 was 11.2 pg/ml. The VEGF concentration after treatment with 0.500 pg/ml BMP-2 was 233.0 pg/ml and after treatment with 1 ng/ml BMP-2 was 2,969.0 pg/ml. The addition of increasing amounts of BMP-2 to lung A549 lung cancer cells growing in culture also caused a dose responsive increase in the expression of the oncogene Sonic Hedgehog. [FIG. 12]

Figure 13A:
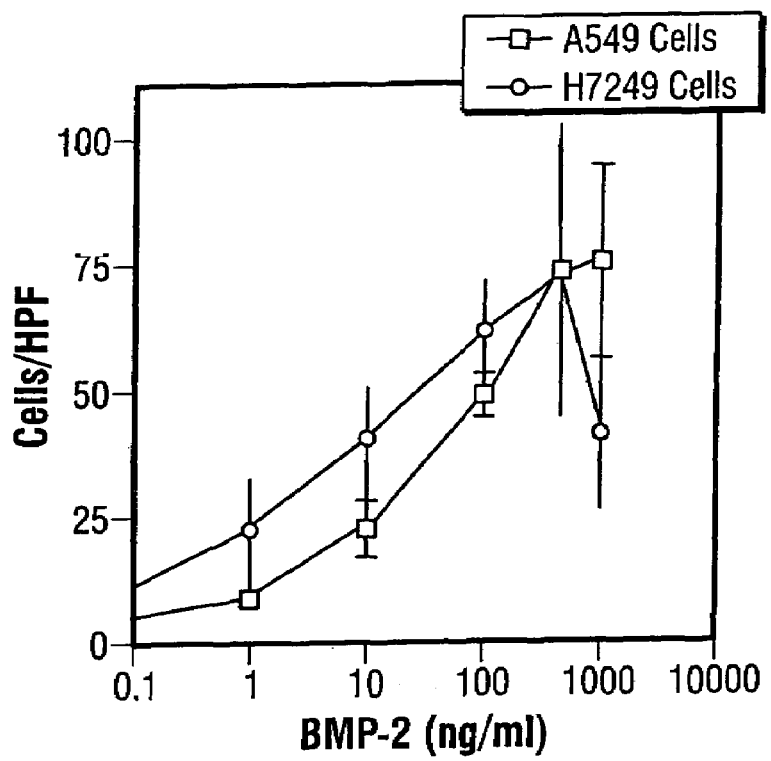
FIG. 13(a): Recombinant human BMP-2, 1 ng/ml, 10 ng/ml, 100 ng/ml, 500 ng/ml, or 1000 ng/ml was added to the lower well of the transwell chamber. Migrated cells were counted using fluorescent microscopy.

In addition, the present experiments showed that BMP-2 stimulates the migration and invasion of the human lung cancer cell lines A549 and H7249. In one assay, recombinant BMP-2 caused a dose responsive increase in migration of cells from transwell migration chambers. [FIG. 13(a)] In another, BMP-2 stimulated the migration of A549 and H7249 cells cultured on glass cover slips toward Affi-blue agarose beads containing recombinant BMP-2. [FIG. 13(c) and (d)] In addition, using transwell chambers coated with MATRIGEL, the inventor also showed that recombinant BMP-2 caused a dose responsive increase in the invasion of both A549 and H7249 cells. [FIG. 13(e)]

Effects of Inhibiting BMP-2 Expression

After finding that BMP-2 enhances cancer invasion and growth, The inventor conducted experiments to determine whether inhibitors of the activity of BMP-2 could be used to treat cancer. In these studies, recombinant mouse noggin (R & D Systems, Minneapolis, Minn.) was used as a representative inhibitor.

The effects of BMP-2 and noggin on tumor growth in vivo were examined by co-injecting the A549 cells subcutaneously into nude mice with Affi-Blue agarose beads coated with either albumin, recombinant human BMP-2, or recombinant human noggin. The animals were then sacrificed and tumors measured at 12 or 19 days. Inhibiting BMP-2 activity with noggin resulted in a statistically significant decrease in tumor growth. Addition of BMP-2 resulted in a statistically significant increase in tumor growth.

Figure 13B:
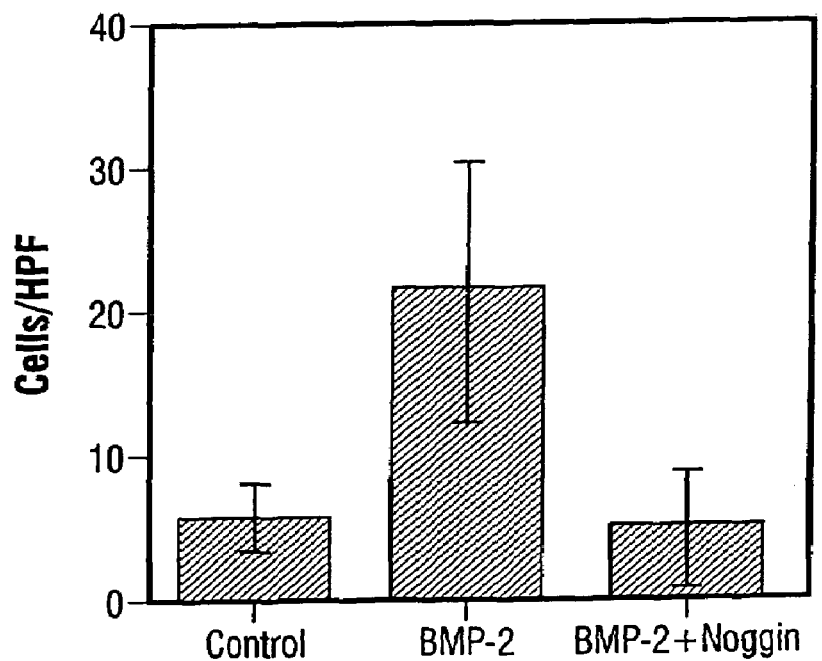
FIG. 13(b): Noggin inhibits BMP-2 induced migration. Lane (1), media alone; (2) recombinant BMP-2 (500 ng/ml); (3) noggin (10 mg/ml) and recombinant BMP-2 (500 ng/ml).
Figure 13E:
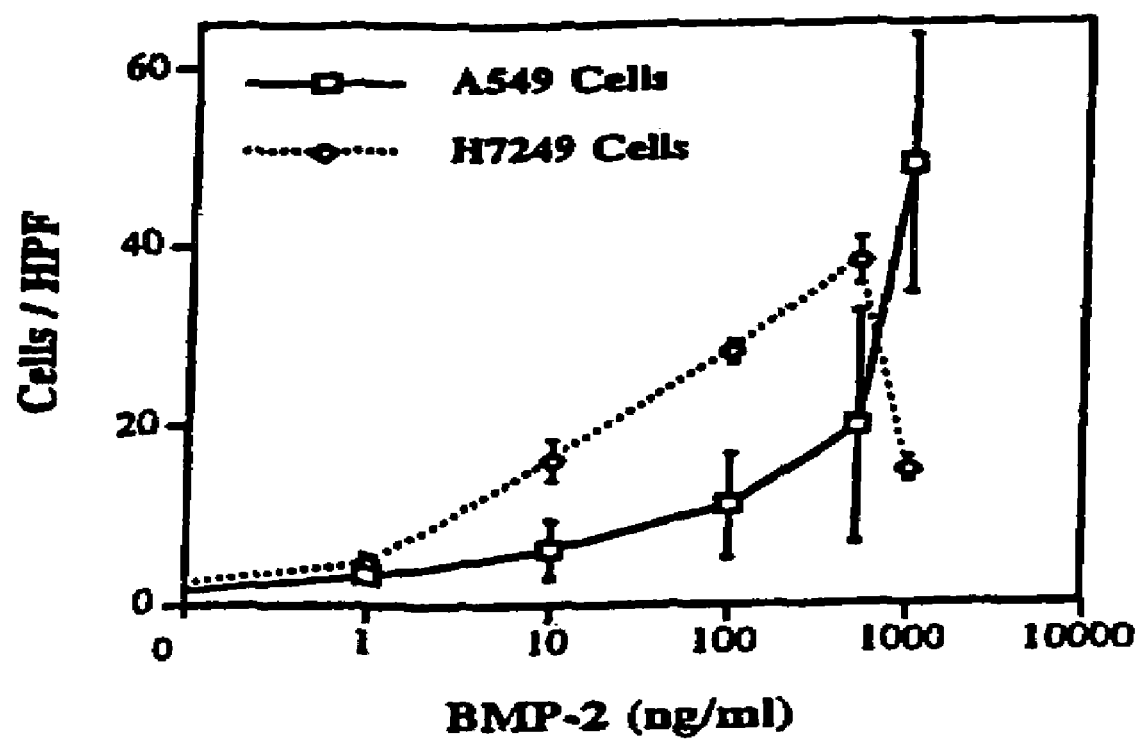
FIG. 13(e): Recombinant human BMP-2 stimulates the invasion of A549 or H7249 cells. Recombinant BMP-2, 1 ng/ml, 10 ng/ml, 100 ng/ml, 500 ng/ml, or 1000 ng/ml was added to the lower wells of a Matrigel invasion chamber. Experiments were repeated at least 3 times. Data was presented as mean±5 standard deviation.
Figure 14:
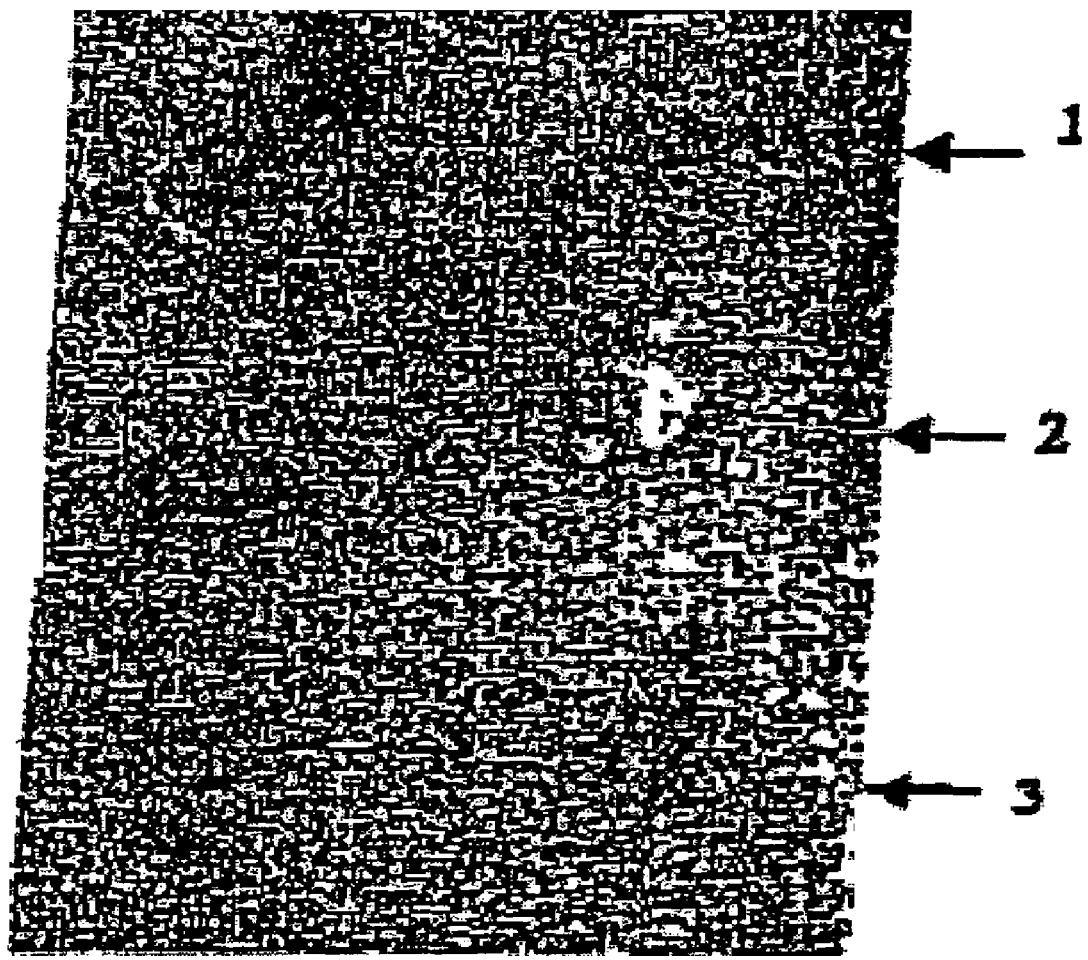
FIG. 14 shows tumor growth after 19 days following the subcutaneous co-injection of A549 lung cancer cells into nude mice with Affi-blue agarose beads coated with (1) 100 ug/ml of albumin, (2) recombinant human BMP-2, or (3) recombinant mouse noggin.

[FIG. 14] The inventor also found that noggin completely inhibited the ability of BMP-2 to enhance the migration of the A549 cells in a transwell chamber. [FIG. 13(b)] Noggin also decreased the expression of VEGF and sonic hedgehog when added to A549 cells.

Figure 12:
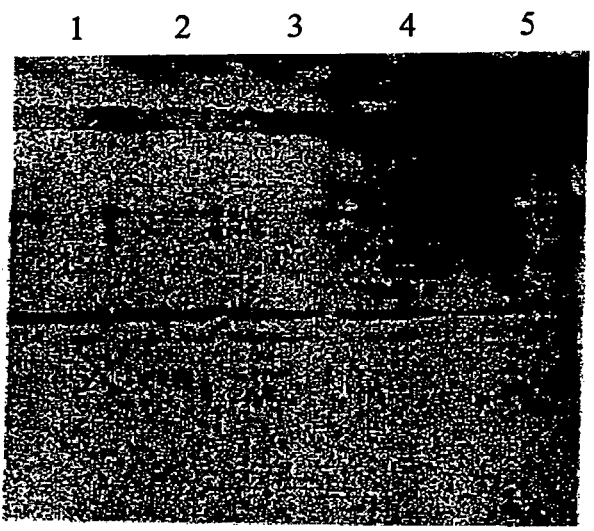
FIG. 12 shows that BMP-2 regulates sonic hedgehog expression.
Figure 12:
Figure 15:
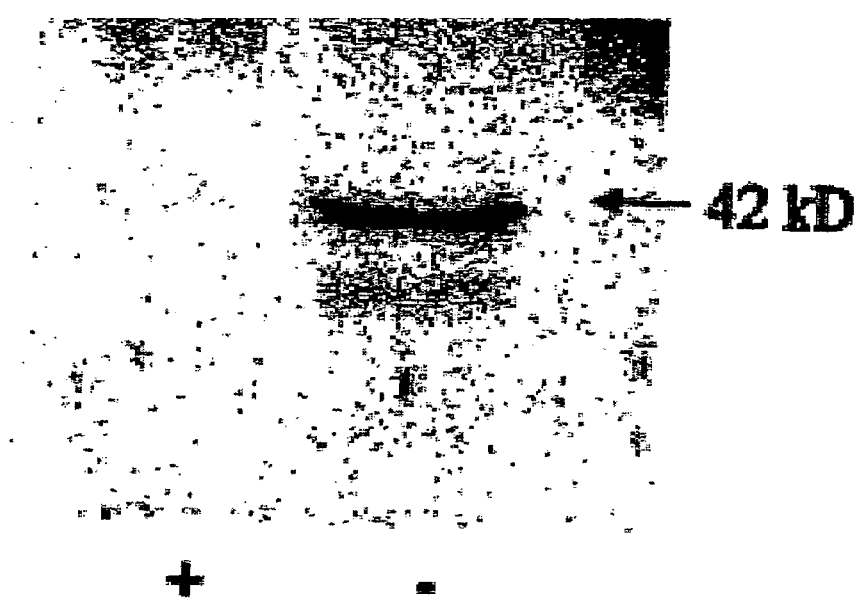
FIG. 15 shows that noggin inhibits VEGF expression in the A549 lung cancer cell line. The Western blot, FIG. 15(a), was probed with anti-VEGF antibody. The lane labeled with a plus was cell culture media from cultures treated with noggin. The lane labeled with a minus was cell culture media from control cultures.

[FIGS. 12 and 15]

Mechanism of BMP-2 Action

The next set of experiments revealed that BMP-2 significantly enhanced neovascularization of developing tumors. Recombinant BMP-2 greatly enhanced blood vessel formation in tumors formed from A549 cells injected subcutaneously into athymic nude mice. Recombinant BMP-2 also stimulated angiogenesis in MATRIGEL containing A549 cells in nude mice. The BMP-2 antagonist noggin abrogated BMP-2 induced angiogenic response. Furthermore, antisense transfection of BMP-2 cDna resulted in a decrease in blood vessel formation in the MATRIGLEL assays.

The present experiments reveal that BMP-2 mediated angiogenesis involves a direct activation of endothelial cells. BMP-2 induces tube like differentiation of both human aortic (HAEC) and umbilical vein endothelial cells. BMP-2 also stimulated proliferation of HAEC. BMP-2 activation of endothelial cells involves a Smad 1/5/8 mediated up-regulation of the proangiogenic factors Id1 and ERK-½.

BMP-2 Stimulates Neoangiogenesis in Tumors

Figure 16:
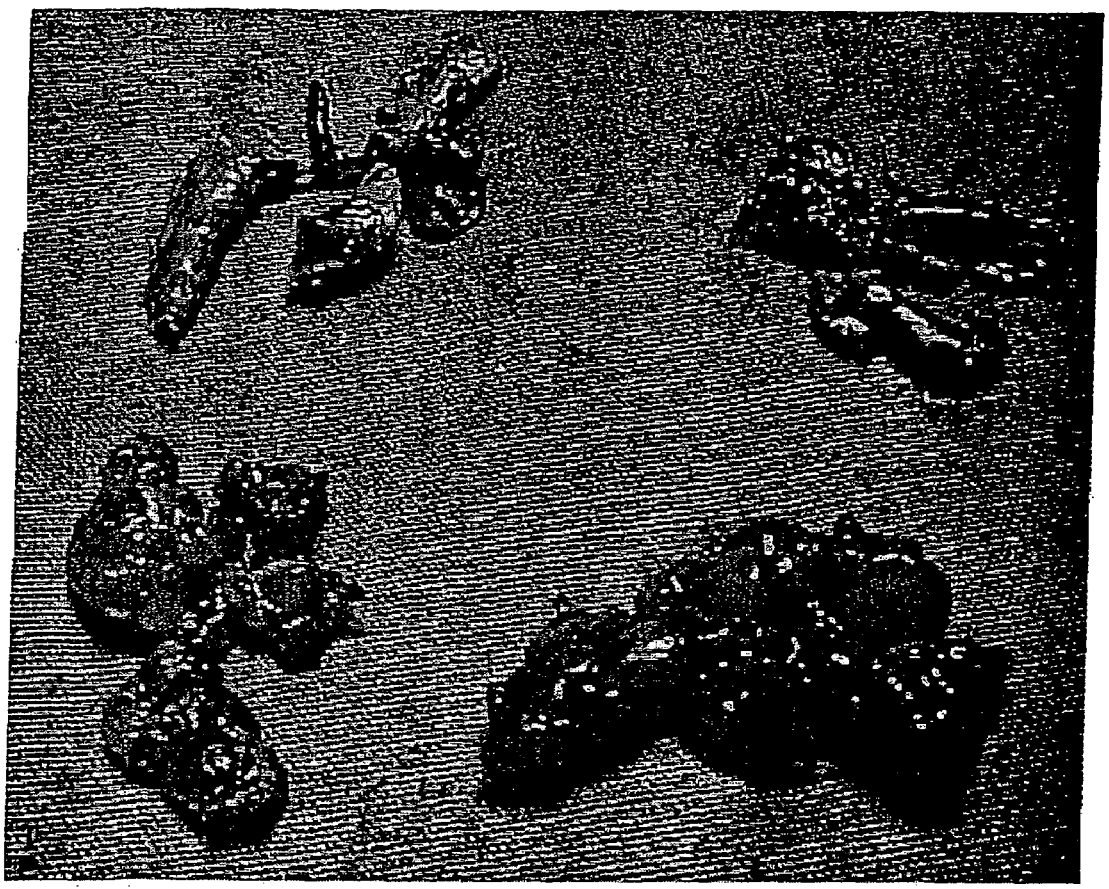
FIG. 16 is a photograph showing excised mouse lungs. The upper set of lungs is controls. The lower set of lungs contains A549 cells with forced expression of BMP-2, which are filled with tumors.

BMP-2 stimulates angiogenesis in developing tumors, which involves the direct activation of endothelial cells. FIG. 16 is a photograph of excised mouse lungs. The top set are controls and the bottom set were subjected to A-549 cells and forced expression of BMP-2. Clearly, the bottom set of lungs is replete of tumors. These data all support the present discovery that the highly expressed BMP-2 significantly enhances lung tumorigenesis by stimulating angiogenesis.

Figure 17:
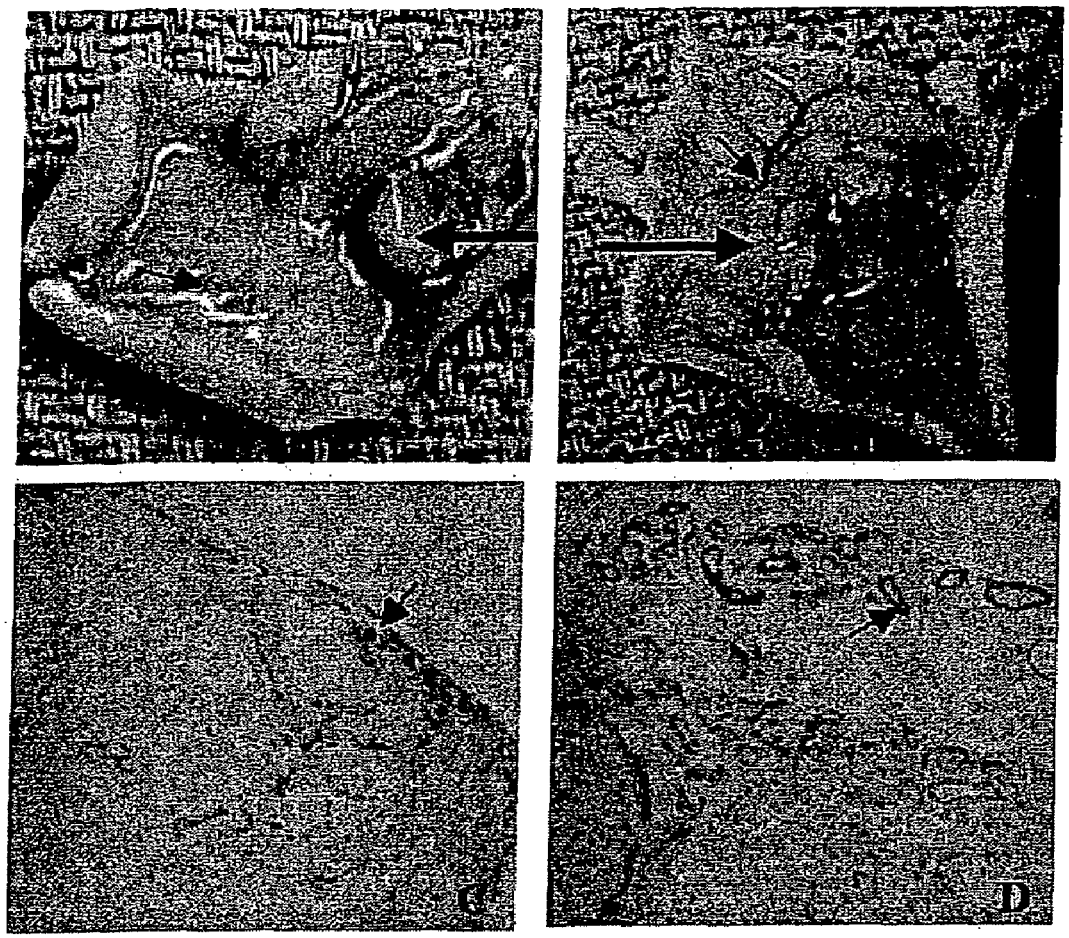
FIG. 17 shows that BMP-2 stimulates tumor neovasculature. A549 cells were co-injected subcutaneously into nude mice with Affi-Blue agarose beads coated with (A) BSA or (B) recombinant human BMP-2. Bold arrow highlights the tumor and smaller arrow a blood vessel feeding the tumor. Endothelial cells within the tumors were measured by immunohistochemistry. Photograph of representative immunohistochemical study showing blood vessels in tumors treated with (C) BSA or (D) recombinant BMP-2. Arrow demonstrating blood vessels that are staining brown. (E) Data showing the number of blood vessels per 40× field in tumors treated for 4-6 or 12-14 days. Data depicts the average of at least 3 experiments per time point. * $p<0.05$
Figure 17:
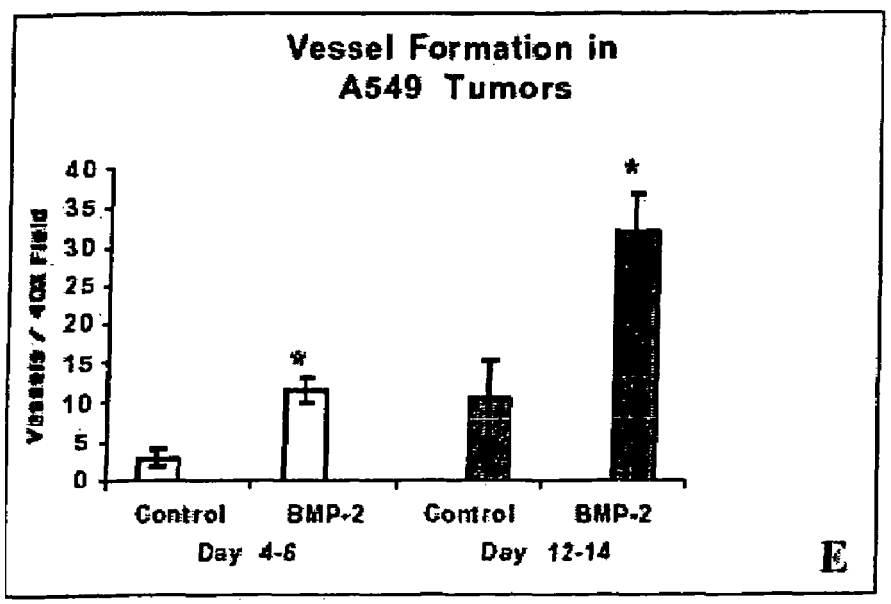

To assess the effects of BMP-2 on blood vessel formation in developing tumors, A549 cells were co-injected with Affi-Blue agarose beads coated with recombinant BMP-2 subcutaneously into athymic nude mice. On visual inspection, tumors treated with BMP-2 [FIG. 17B] had larger and more numerous blood vessels than those treated with BSA. [See FIG. 17A] Immunohistochemistry studies revealed a 6-fold increase in the number of blood vessels that formed within the tumors treated with BMP-2 [FIG. 17D] as opposed to the control. [FIG. 17C] The BMP-2 mediated angiogenic response occurred rapidly demonstrating an increase in blood vessels by the sixth day that persisted until at least the eighteenth day post injection. FIG. 17E is a bar graph illustrating the blood vessel growth in A549 tumors at varying points in time.

Figure 18:
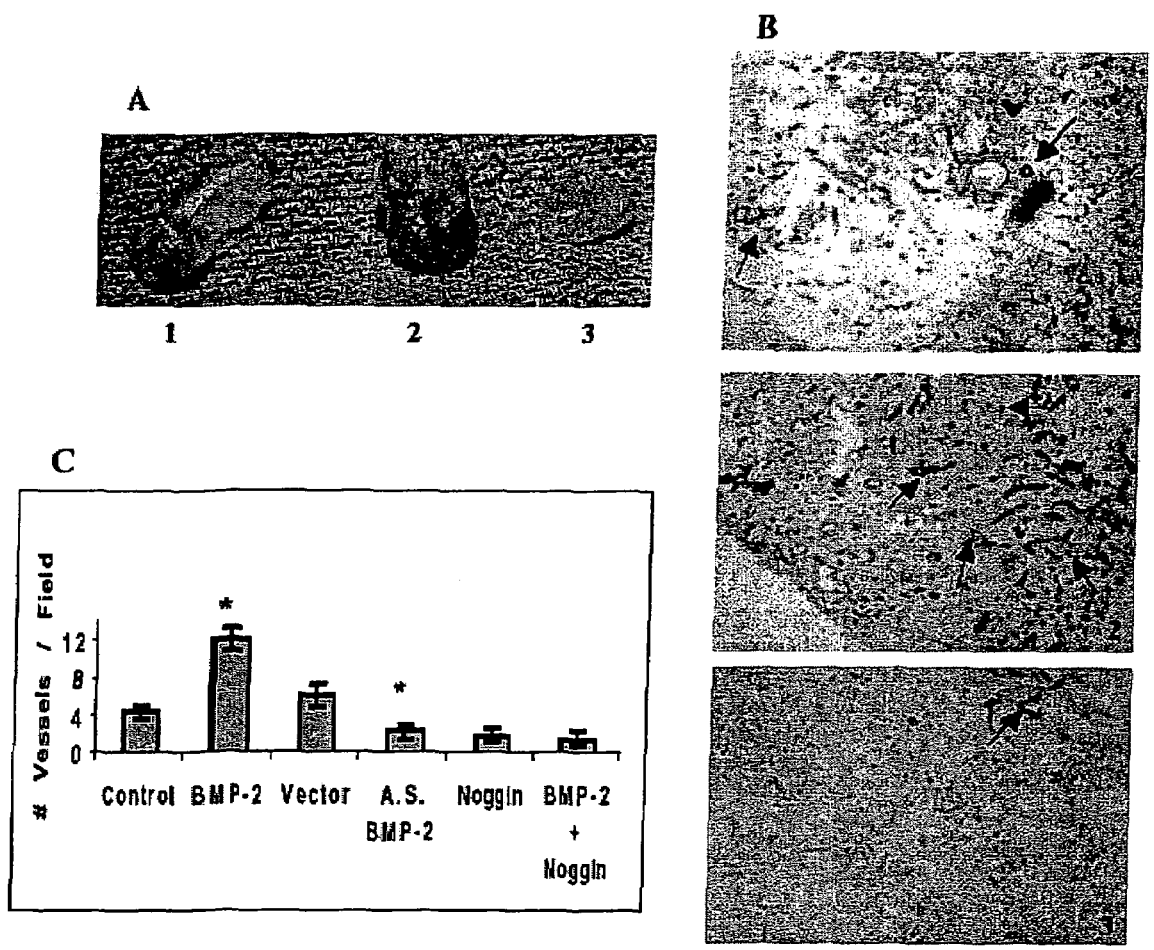
FIG. 18 is a MATRIGEL angiogenesis assay. (A) Photograph of MATRIGEL plugs containing A549 cells supplemented with (A1) BSA or (A2) recombinant BMP-2 or (A 3) MATRIGEL plug containing A549-AS cells alone (AS). (B) Representative photograph of an immunohistochemical study demonstrating endothelial cells within the MATRIGEL plugs. Blood vessels are staining brown. MATRIGEL plugs containing A549 cells supplemented with (B1) BSA (B2) recombinant BMP-2 or (3) A549-AS alone. Experiments were repeated 6 times. (C) Graphic representation of the number of blood vessels per high-powered field. Also shown is the number of blood vessels in MATRIGEL plugs containing BMP-2 preincubated with recombinant noggin and A549 cells transfected with pcDNA3 (vector). *$p<0.05$ compared to control.

To further assess the effects of BMP-2 on tumor neoangiogenesis, A549 cells were mixed in MATRIGLEL supplemented with recombinant BMP-2 or BSA and injected subcutaneously into athymic nude mice. Blood vessel formation induced from A549 cells engineered to secrete less BMP-2 by anti-sense transfection (A549-AS) was also examined. Overall, MATRIGLEL plugs containing BMP-2 [FIG. 18A-2] had more blood vessels than that of controls [FIG. 18A-1]. A549-AS cells showed no evidence of a neovasculature after 6 days [FIG. 18A-3]. Immunohistochemistry also demonstrated significantly more blood vessels within the MATRIGLEL plugs treated with recombinant BMP-2 [FIG. 18B-2]. MATRIGLEL plugs containing A549-AS cells [FIG. 18B-3] had fewer blood vessels than A549 cells treated with BSA [FIG. 18B-1] or A549 cells transfected with vector alone (vector). [FIG. 18C] Inhibiting the activity of BMP-2 with its antagonist noggin, abrogated the angiogenic response induced by recombinant BMP-2 [FIG. 18C].

BMP-2 Activates Smad 1, ID1, and ERK ½

Figure 19:
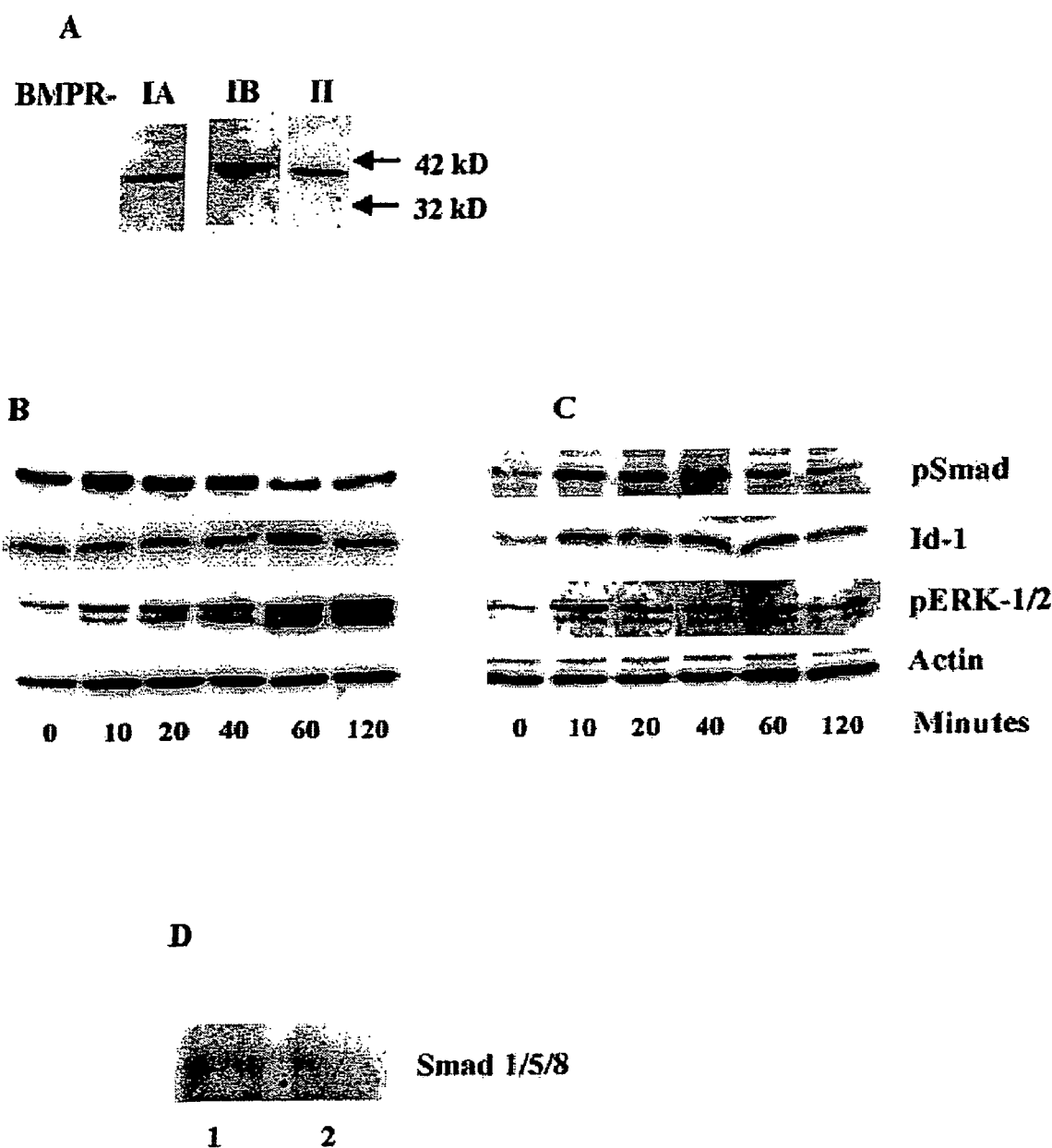
FIG. 19 is four blots demonstrating BMP-2 activates endothelial cells. (A) Western blot analysis was performed on cell lysate from HAEC and probed with antibodies specific for BMP receptors IA, IB, and II. (B) HAEC and (C) HUVEC were treated with recombinant BMP-2 and cell lysates were subjected to Western blot analysis using antibodies specific for phosphorylated Smad1, ID1, and phosphorylated ERK-½. An anti-actin antibody was used as a loading control. Experiments were repeated at least 3 times. (D) HAEC protein was precipitated with an anti-Smad 1/5/8 antibody and Western blot probed with an anti-phosphoserine antibody. HAEC were treated with (1) recombinant BMP-2 or (2) vehicle control.

The next experiment examined whether BMP-2 induced angiogenesis involves the activation of human endothelial cells. Western blot analysis showed the expression of BMP-specific receptors in human aortic endothelial cells (HAEC) [FIG. 19A]. To determine whether BMP-2 activated BMP-specific Smads, an antibody that recognized the phosphorylated form of Smad1 was used. BMP-2 induced the phosphorylation of Smad1 within 10 minutes in both the HAEC [FIG. 19B] and human umbilical vein endothelial cells (HUVEC) [FIG. 19C]. BMP-2 mediated Smad phosphorylation persisted for approximately 40 minutes in both endothelial cell lines. To further assess BMP-2 induced Smad phosphorylation, cell lysate from HAEC treated with and without BMP-2 was immunoprecipitated with an antibody recognizing Smads 1,5, and/or 8 and immunoblots were probed with an antibody recognizing phosphorylated serines [FIG. 19D]. This study also demonstrated that BMP-2 induces the phosphorylation of BMP-2 specific Smads in endothelial cells. An isotype control antibody did not immunoprecipitate Smads 1,5, and/or 8.

It is known that BMP-6 activates ID1 in BAEC and MEEK cells. Id is a negative regulator of basic helix loop transcription factors and was shown to regulate endothelial migration and possibly tube formation. The present experiment found that BMP-2 induces a transient increase in the expression of Id1 in both the HAEC [FIG. 19B] and HUVEC [FIG. 19C].

Because proangiogenic proteins vascular endothelial growth factor (VEGF), fibroblastic growth factor (FGF), epidermal growth factor (EGF), and angiogenin mediate a cellular response in endothelial cells through the activation of extracellular signal-regulated kinase (ERK-½), this experiment examined whether BMP-2 also activates ERK-½. An antibody specific for phosphorylated ERK-½ was used in Western Blot analysis. BMP-2 induced a rapid increase in the phosphorylation of ERK-½ in both the HAEC and HUVEC. A robust increase was seen in the HAEC that persisted for at least 2 hours [FIG. 19B]. Phosphorylation of ERK-½ in the HUVEC was not as robust and persisted for only 60 minutes [FIG. 19C].

BMP-2 Induced Nuclear Translocation of Smad 1, 5, and/or 8

Figure 20A:
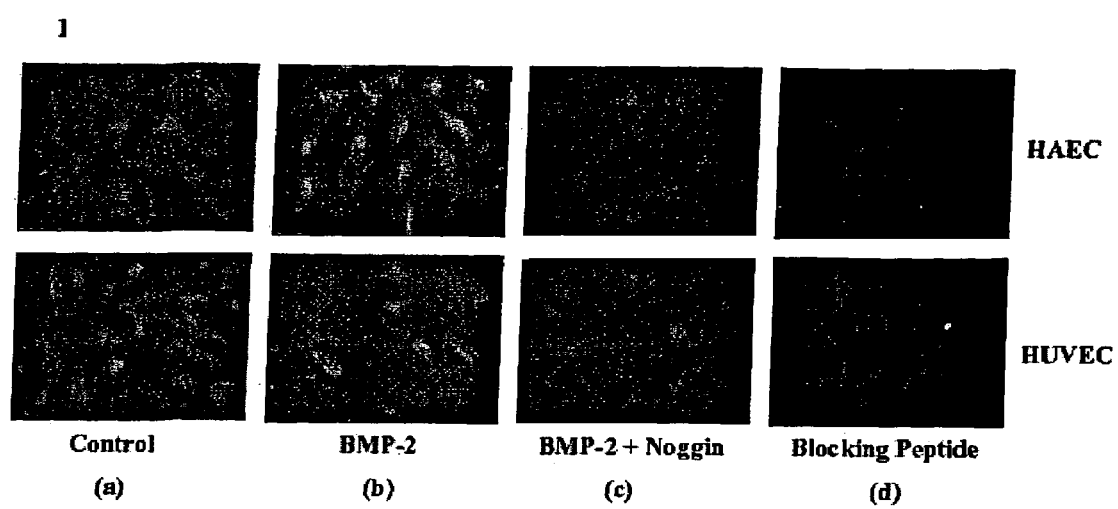
FIG. 20: BMP-2 Induces Nuclear Accumulation of Smad 1/5/8. Localization of Smad 1, 5 and 8 was determined by immunofluorescence microscopy. HAEC or HUVEC were treated for 30 minutes with I(a) vehicle control I(b) recombinant BMP-2 I(c) recombinant BMP-2 and recombinant noggin or I(d) anti-Smad 1/5/8 antibody with blocking peptide.
FIG. 20(b): II. HAEC or HUVEC were treated with recombinant BMP-2 for the designated time points. (II A) Imaging using differential interference contrast microscopy and (II B) immunofluorescent microscopy. (II C) The percentage of HAEC or HUVEC demonstrating nuclear staining after BMP-2 treatment. A minimum of 100 cells were counted. Each study was performed at least 3 times.
Figure 20B:
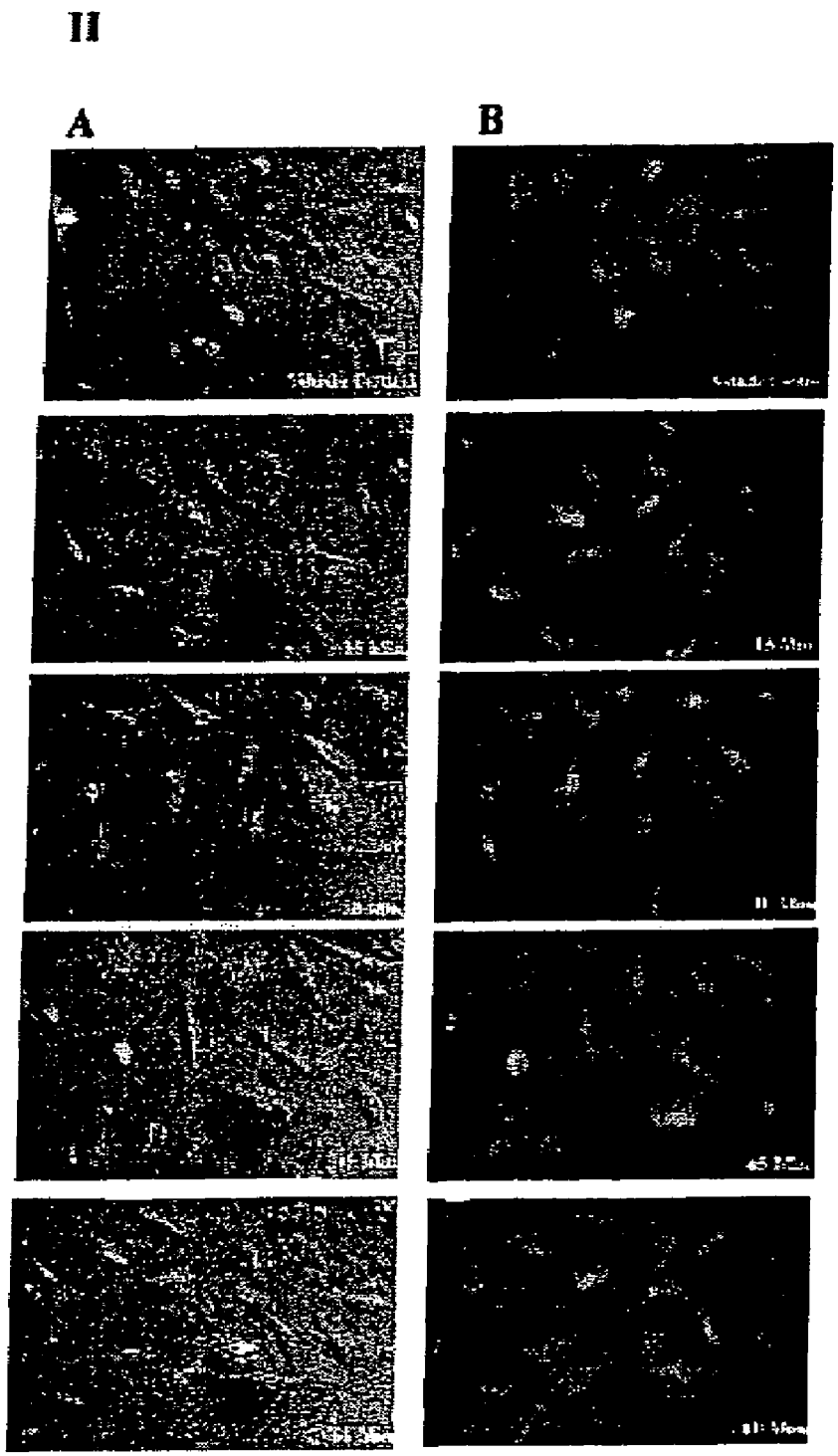

Phosphorylation of Smads 1, 5, and/or 8 stimulates its translocation from the cytoplasm into the nucleus, which then induces transcription of target genes. Using immunofluorescence, the next experiment examined whether BMP-2 stimulates the translocation of Smads 1/5/8 into the nucleus in human endothelial cells. The findings indicate that BMP-2 increases nuclear expression of Smads 1,5, and/or 8 in both HAEC and HUVEC (FIG. 20A). Noggin completely antagonized recombinant BMP-2 and induced nuclear accumulation of Smad 1/5/8 [FIG. 20A]. Pre-incubating the anti-Smad 1, 5, and/or 8 antibody with a peptide recognized by this antibody abrogated all fluorescent signals [FIG. 20A]. Nuclear staining of Smad 1/5/8 corresponded to the BMP-2 induced phosphorylation of Smad 1 found by Western blot analysis. BMP-2 mediated influx of Smads 1/5/8 into the nucleus was greatest after 30 minutes and returned to baseline levels within 60 minutes [FIGS. 20B and 20C].

BMP-2 Stimulates Endothelial Cell Proliferation and Tube Formation

Figure 21:
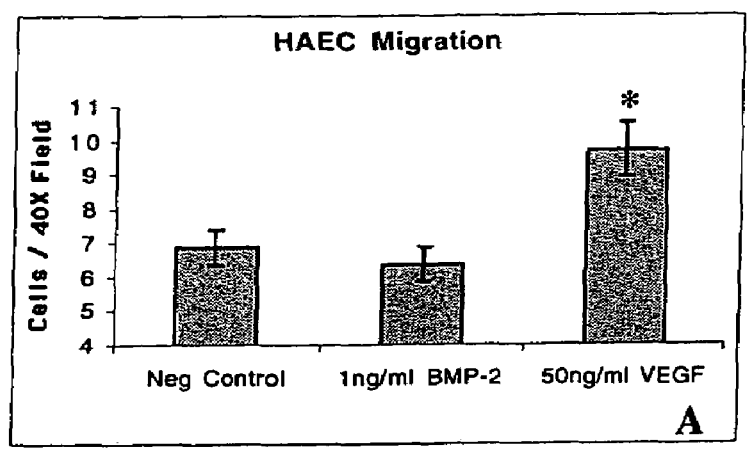
FIG. 21 is a series of three bar graphs illustrating that BMP-2 stimulates proliferation, but not migration of endothelial cells. (A) Migration of HAEC treated with vehicle control, BMP-2, or VEGF. The rate of DNA synthesis was determined by measuring incorporated H3-thymidine. (B) The rate of DNA synthesis of HAEC treated with recombinant BMP-2. (C) The rate of DNA synthesis of HUVEC treated with recombinant BMP-2. Values reported represent the average of 3 independent experiments performed in duplicate. *$p<0.05$.
Figure 21:
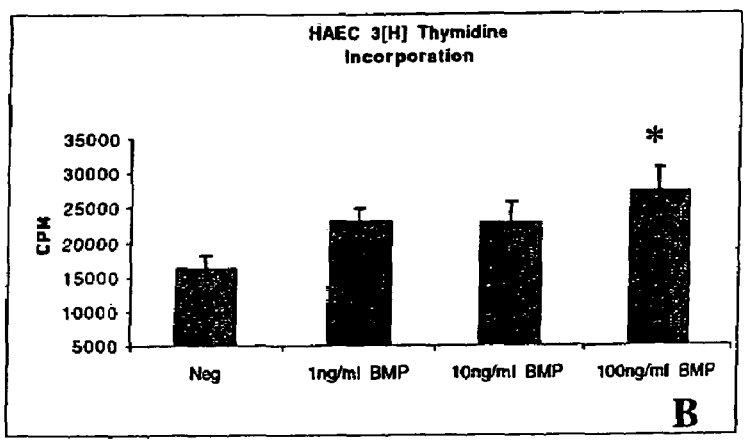
Figure 21:
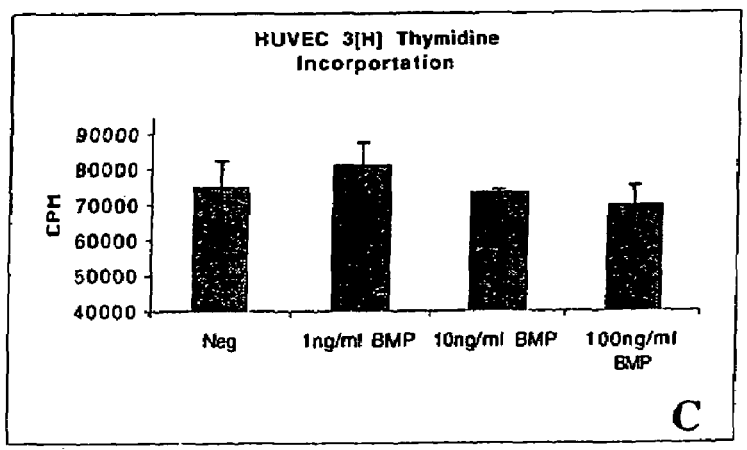
Figure 22:
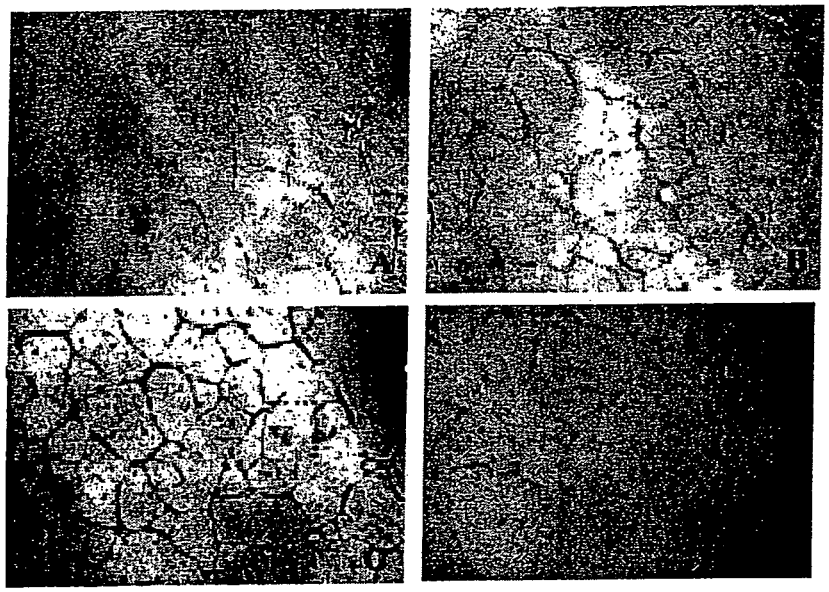
FIG. 22: BMP-2 Stimulates Tube Formation of Endothelial Cells. Representative photograph of tube-like structures formed by HAEC treated with (A) vehicle control (B) 500 pg/ml BMP-2 (C) 1 ng/ml BMP-2 or (D) BMP-2 pre-incubated with noggin. Original magnification was a 4×. Graphic representation of the number of tubes per low powered field for (E) HAEC and (F) HUVEC. Each condition was repeated at least 3 times in duplicate. *$p<0.05$ compared to control.
Figure 22:
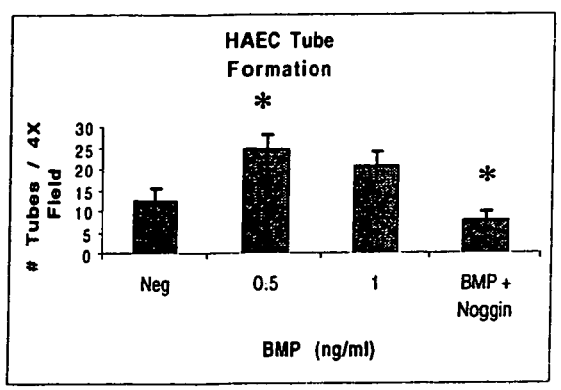
Figure 22:
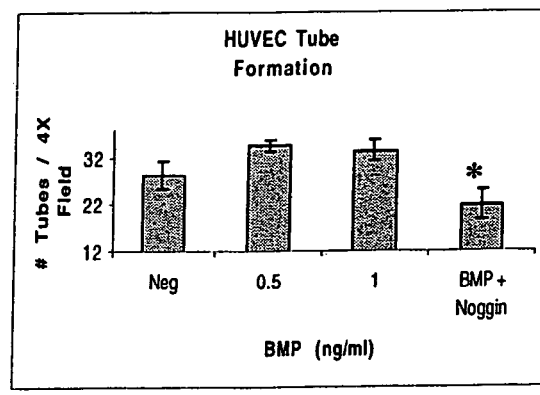

The next study examined whether BMP-2 stimulates proliferation, tube formation and/or migration of human endothelial cells. Unlike BMP-6, which stimulates the migration of BAEC, BMP-2 did not induce the migration of HAEC [FIG. 21A]. To study the effects of BMP-2 on proliferation, the HAEC and HUVEC were treated with recombinant BMP-2 for 24 hours and pulsed with $H^3$-thymidine for one hour. The effects of BMP-2 on proliferation varied between the HAEC and HUVEC. BMP-2 stimulated a dose responsive increase in DNA synthesis in HAEC [FIG. 21B]. Relatively little change in DNA synthesis was seen in the HUVEC following treatment with BMP-2 [FIG. 21B]. There was no difference in proliferation when $^3$H-thymidine incorporation was measured 6 hours after adding BMP-2 to HUVEC. [FIG. 21C]

To study whether BMP-2 induced tube formation, the HAEC or HUVEC were plated on MATRIGEL coated plates and treated with and without recombinant BMP-2 [FIG. 22A-D]. BMP-2 produced a robust increase in the tube formation in both the HAEC [FIG. 22E] and HUVEC [FIG. 22F]. The greatest effect on tube formation Occurred at 500 pg/ml of BMP-2 with a lesser effect at higher concentrations. Noggin inhibited BMP-2 induced tube formation in both the HAEC [FIG. 22E] and HUVEC [FIG. 22F].

BMP-2, but not BMP-4, is Aberrantly Expressed in Non-Small Cell Lung Carcinomas (NSCLC) and Stimulates Tumor Growth of A549 Cells in an Autocrine Manner BMP-2 and BMP-4 are known to induce pluripotent cell differentiation, enhance cell migration, and stimulate proliferation during embryonic development. Despite being powerful morphogens, it was previously unknown whether BMP-2/4 have significant biological activity in human carcinomas or whether the mature active BMP-2/4 protein is aberrantly regulated and expressed in patient-derived tumors.

This aspect of the present invention reveals that the mature BMP-2 protein is highly over-expressed in human NSCLC with little to no expression in normal lung tissue or benign lung tumors. BMP-4 is expressed, but is not highly overexpressed. The expression of BMP-2 is localized specifically to the cancer cells. Recombinant BMP-2 stimulated in vitro the migration and invasiveness of the A549 and H7249 human lung cancer cell lines. In vivo, recombinant BMP-2 enhanced the growth of tumors formed from A549 cells injected subcutaneously into nude mice. Furthermore, inhibition of BMP-2 activity with either recombinant noggin or anti-BMP-2 antibody resulted in a significant reduction in tumor growth. This study shows that expression of the mature, active BMP-2 protein is disregulated in the majority of NSCLC. BMP-2 has important biological activity in lung carcinomas, as shown through its enhancement of tumor cell migration and invasion, as well as stimulating tumor growth in vivo.

The experiment used RDA to identify the expression of BMP-2 mRNA in a patient derived non-small cell lung carcinoma. High levels of expression of the mature active BMP-2 protein were shown in all of the NSCLC examined, with little to no expression in normal lung tissue. This present study shows the mature BMP-2 protein is highly over-expressed in most or all patient-derived lung carcinomas, and that mature BMP-4 protein is not significantly expressed in human lung carcinomas.

BMP-2 has important biological activity in human lung carcinomas. The natural BMP-2 inhibitor, noggin, caused a significant reduction of tumor growth of the A549 cells in nude mice. Noggin has a high affinity to BMP-2 and BMP-4 with a much lower affinity to BMP-7. Noggin has also been shown to inhibit growth differentiation factor-5 (GDF-5) and GDF-6. Although noggin could potentially inhibit other BMP proteins affecting tumor growth, the present invention shows that the inhibition was specific for BMP-2. The studies did not reveal expression of the mature BMP-4 protein in patient derived lung carcinomas or of BMP-7 or GDF-5 protein in human lung tumors. Furthermore, the findings that an anti-BMP-2 antibody also inhibited tumor growth and that recombinant BMP-2 enhanced tumor growth in vivo further support that BMP-2 has a significant role in lung tumorigenesis.

The addition of recombinant BMP-2 to the A549 cells injected into nude mice did not induce bone or cartilage formation. The reason for this apparent discrepancy of expected BMP-2 in vivo activity is not known. However, the present invention further proves that not all biological activity associated with BMP-2/4 involves the formation of bone or cartilage. The biological response of BMP-2 or BMP-4 may depend not only on the particular cell types present, but may vary depending on the presence of other cytokines.

Since BMP-2 is a secreted protein, it can act in a paracrine and/or autocrine manner. This invention demonstrates that BMP-2 stimulates the migration of lung cancer cell lines in vitro. Therefore, one autocrine mechanism of BMP-2 is to enhance the invasiveness of a tumor by autocrine activation of tumor cells, which promotes their proliferation. [FIG. 23] At high concentrations, BMP-2 suppressed the growth of the A549 cells in SFM, showing that it suppresses the growth of cancer cells. Since BMP-2 enhances tumor growth in vivo, this suggests that BMP-2 also acts by paracrine mechanisms. However, the effects of BMP-2 on cell growth may vary depending on the cell culture conditions. There are several potential mechanisms through which BMP-2 could enhance carcinogenesis in a paracrine manner, including inducing stem cell differentiation, enhancing migration of vascular smooth muscle cells and monocytes, and stimulating the production of an extracellular matrix.

Figure 23:
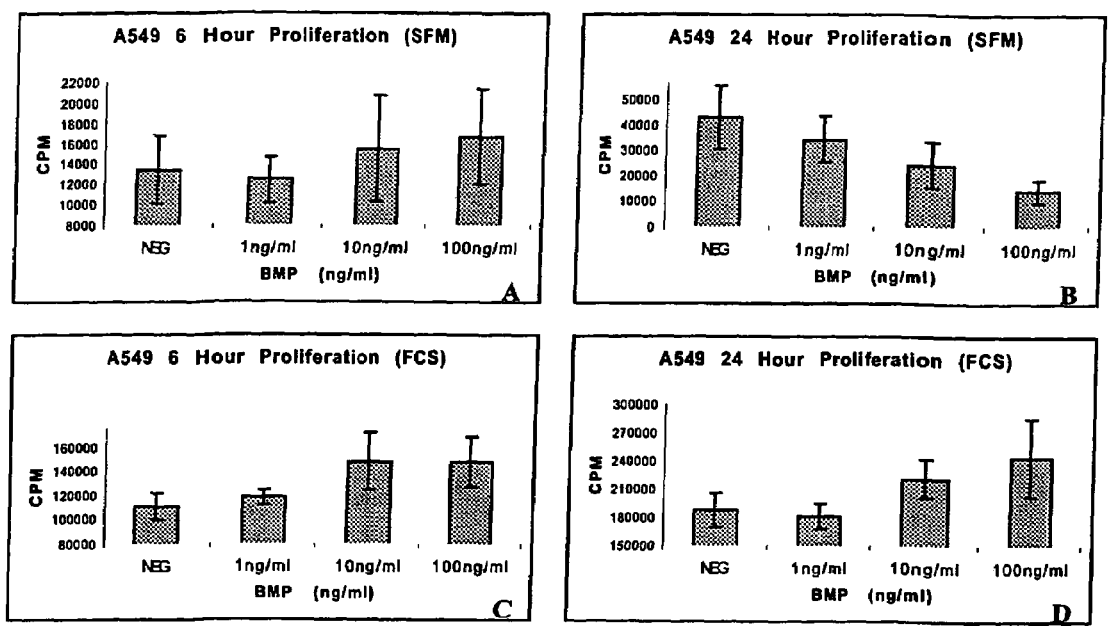
FIG. 23 shows the A549 cell proliferation for both 6 and 24 hours in SFM and FCS with varying concentrations of BMP administered.

Further supporting BMP-2's role in autocrine stimulation, the study also shows that BMP-2 is able to both stimulate and inhibit the proliferation of the same cancer cell line depending on the cell culture media. [FIG. 23] This invention showed BMP-2 causes a significant decrease in the proliferation of A549 cells cultured in serum free media (SFM) over time. [FIG. 23B] However, BMP-2 stimulated the proliferation of A549 cells in Dulbecco's Modified Eagle Medium (DMEM) fetal calf serum (FCS).

[FIGS. 23C and 23D]

Consistent with BMP-2 being a growth promoting cytokine, BMP-2 induced a rapid increase in the expression of Id1 and cyclin E and phosphorylated Erk ½ and Rb. Surprisingly, the same pattern of expression of these genes was seen in both DMEM FCS and SFM when examined at very early time points. However, when these same signaling pathways were examined at a later time when the effects on proliferation between the two cell culture conditions were clearly different, the expression of these genes was entirely different. A549 cells treated with BMP-2 cultured in DMEM-FCS continued to show signaling consistent with enhanced proliferation with phosphorylation of Erk ½ and Rb, and a decrease in p21. While in SFM, there was a growth inhibitory pattern with hypophosphorylation of Erk ½ and Rb, a decrease expression of cyclin E, and an increased expression of p21. Together, these studies show that BMP-2 induces both growth stimulating and growth inhibiting pathways but the growth inhibitory pathway is blocked by undefined cytokines present in the DMEM FCS. Of interest is that BMP-2 induces signaling pathways in cancer cells known to promote tumorigenesis. BMP-2 has not previously been shown to induce Erk signaling in cancer cells.

BMP-2 Induces Erk and Signaling ID1 in Cancer Cells

The mechanism BMP-2 induces these signaling pathways is not known. Because the activation of Smad ⅕ in SFM was not detected, this suggests that BMP-2 stimulates cyclin E, ID1, and phosphorylates Erk ½ and Rb by a Smad ⅕ independent mechanism. Activated Erk ½ has been shown to induce the transcription of cyclin E. Therefore, it is possible that BMP-2 induces phosphorylation of Erk ½ by a Smad ⅕ independent mechanism, which then causes an increase in cyclin E expression. Cyclin E can then bind ckd-2 leading to Rb phosphorylation (inactivation) allowing for progression through the cell cycle. BMP-2 also induces a rapid and strong activation of ID1 in A549 cells. The present study reveals that BMP-2 may also stimulate Id expression by Smad ⅕ independent mechanisms.

The study also found BMP-2 produced significantly more apoptosis in A549 cells cultured in SFM than in DMEM FCS. This may account for the differences in proliferation noted between the two cell culture conditions. Interestingly, BMP-2 has been shown to induce apoptosis in human osteoblasts which occurs by a Smad independent mechanism (42). However, BMP-2/4 has also been shown to inhibit apoptosis in mesenchymal stem cells and myocytes (43-44). Both of these studies showed that BMP-2/4 inhibited apoptosis through Smad 1/5 (43-44). These data suggest that in SFM, BMP-2 induced apoptosis because of the lack of active Smad 1/5, while in the presence DMEM FCS BMP-2 activated Smad 1/5 therefore inhibiting any apoptotic signaling, enhancing cell survival and proliferation.

In conclusion, these data suggest that BMP-2 is a growth promoting cytokine in cancer that involves the autocrine regulation of cancer cells. The biological response induced by BMP-2 is dependent on the cell culture conditions. In the presence of serum containing medium, BMP-2 stimulated a prolonged expression of signaling pathways known to be frequently dysregulated in lung cancer. These data further support the hypothesis that BMP-2 has an important role in promoting tumorigenesis.

EXAMPLES

Example 1

Identification of BMP-2 Using Representational Difference Analysis Subtraction Technique Representational difference analysis (RDA) subtraction technique was used to identify genes highly expressed in a non-small cell lung carcinoma obtained from a patient (tester) in comparison to normal bronchial human epithelial cells (driver). The technique for RDA described in the following references was followed: Holmes, M. L., et al., *Molecular and Cellular Biology* 19: 4182-4190 (1999); Hubank, M., *Nucleic Acids Research* 22:5640-5648 (1994). Normal human bronchial epithelial cells were purchased from Clonetics, BioWhitaker (Walkersville, Md.) and were maintained in serum free media. Human tissue specimens were obtained directly from the operating room and immediately frozen in liquid nitrogen. Tissue was stored in liquid nitrogen at −70° C.

To perform RDA, mRNA was purified from the samples using Oligo dT columns (Pharmacia, Peapack, N.J.) according to the manufacturer's instructions and cDNA was then obtained using the PHARMACIA TIME SAVER cDna synthesis kit also according to the manufacturer's instructions. cDNA was digested with Sau3A I endonuclease, R-linker ligated, and amplified by PCR. The R-linkers were removed and J-linkers ligated to the tester. The driver and tester cDNA were hybridized at 67° C. for 20 hours (driver in excess i00:i) and the subtracted tester cDNA amplified by PCR. A second round of subtraction was performed using N-linkers (driver in excess 800,000:1). The amplified PCR products were cloned into blue script and sequenced using an ABI Prism 377 DNA sequencer. Known genes corresponding to the subtracted tumor cDNA were identified by a BLAST database search.

Example 2

Detection of Expression of BMP-2 in Human Lung Cancer Specimens Using RT-PCR

Reverse transcriptase polymerase chain reaction was performed using standard techniques well known in the art. The forward primer was acgagagctctcactggtcc (SEQ ID NO: 15). The reverse primer was cattccggattacatgaggg (SEQ ID NO: 16). The chain reaction consisted of denaturation at 95° C. for 1 min, annealing at 54° C. for 1 min, and extension at 72° C. for 2 min for 33 cycles.

Example 3

Detection of Over-Expression of BMP and BMP Receptors in Various Cancer Tissue Specimens and Lung Cancer Cell Lines The inventor detected expression of BMP and BMP receptors in a number of normal and cancerous tissue specimens and cells. As described above, all human tissue specimens were obtained directly from the operating room and immediately frozen in liquid nitrogen and stored at −70° C. Normal human bronchial epithelial (NBE) cells were purchased from Clonetics, BioWhitaker (Walkersville, Md.) and were maintained in serum free media. Immortalized human bronchial epithelial (IHBE), BEAS-2B, cells were derived from normal bronchial epithelial cells immortalized with an adenovirus-12-5-V40 hybrid virus. A549 and H7249 are highly invasive human lung cancer cell lines. The cell lines were cultured in 5% fetal bovine serum (FBS) in Dulbecco's Modified Eagles medium (DME) containing penicillin, streptomycin, and glutamine with 5% $pCO_2$ at 37° C. Western blot analysis was used to detect expression of the BMP ligand and its receptors in all of these samples. Immunohistochemistry studies were performed to detect BMP in non-small cell lung carcinoma samples and normal lung tissue samples derived from patients.

Western Blot Analysis

In preparation for Western blot analysis, cells were lysed in a modified RIPA buffer containing 150 ml NaCl, 50 ml Tris, pH 7.5, 1% NP 40, 10% deoxycholic acid, and protease inhibitor cocktail from Calbiochem. Tissue specimens were sonicated on ice in the same modified RIPA buffer. The protein concentration of the resulting samples was measured using the Bradford assay technique. Recombinant human BMP-2, purchased from R & D Systems and reconstituted in PBS with gelatin, served a control. Total cellular protein of the samples and recombinant human BMP-2 were analyzed by SDS-PAGE, transferred to nitrocellulose filter (Schleicher and Schuell, Keene, N.H.) at 35 V for 16 hours at 4° C. and then incubated with the desired primary antibody. Specific proteins were detected using the enhanced chemiluminescence system (Amersham, Arlington Heights, Ill.).

The primary antibodies that were used included mouse anti-human BMP-2, goat anti-human BMP-4, goat anti-human BMP-7, goat anti-human type IA BMP receptor, and goat anti-human type IB BMP-2 receptor. All of these antibodies, except the goat anti-human BMP-7 were purchased from R & D Systems in Minneapolis, Minn. The goat anti-human BMP-7 antibody was obtained from Santa Cruz (Santa Cruz, Calif.).

Immunohistochemistry Analysis

To perform immunohistochemistry analysis, four micron Cryostat-cut sections were air dried before being fixed in cold acetone for 10 minutes. Sections were washed in cold 0.5 M PBS and intrinsic peroxidase was quenched with 0.03% periodic acid for 20 minutes at room temperature. Sections were then rinsed in cold PBS and 0.5% BSA/PBS was applied to the slides for 15 minutes in a humid chamber. Biotinylated BMP-2/4 (R & D Systems) was applied at a 1:25 dilution in 1% BSA/PBS and incubated overnight at 4° C. Two slides were run as negative controls. One slide was incubated with biotinylated BMP-2 preabsorbed with recombinant human BMP-2 at 1:10 Molar ratio. As a second negative control slide samples were incubated overnight at 4° C. with normal rabbit serum. Slides were washed with cold PBS and incubated for one hour in Streptavidin horseradish peroxidase (Dako) at a 1:500 dilution in 1% BSA/PBS. Slides were then counterstained in 0.7% Toluidine Blue.

Example 4

Detection of Processing of Mature BMP-2 by Human Leukocytes.

Cell culture media from the A549 cells was incubated with leukocytes isolated from whole blood for 16 hours. Then, a Western blot was performed, as described above, on the cell culture media. Mouse anti-human BMP-2 antibody (#MAB355, R & D Systems, Minneapolis, Minn.) was the primary antibody used to detect the C-terminal end of BMP-2. Goat anti-human BMP-2 (Research Diagnostics, Flanders, N.J.) was used to detect the N-terminal end of BMP-2. A Western blot of the leukocytes was also performed with an anti-furin primary antibody to determine that human leukocytes express furin convertase.

Example 5

Analysis of the Effect of BMP-2 and Noggin on Tumor Growth and Tumor Vasculature In Vivo Nude mice studies were conducted to determine the effect of BMP-2 and noggin on tumor growth and tumor vasculature. $10^6$ A549 cells were injected subcutaneously into nude mice with Affi-Blue agarose beads coated with albumin, recombinant human BMP-2, or recombinant mouse noggin. Both of these recombinant proteins were purchased from R & D Systems and were reconstituted in PBS with gelatin. Coating of Affi-Blue agarose beads with BMP-2 and noggin has been described in the literature. (Abe, E., et al., *J. Bone Miner Res.* 15: 663-673 (2000); Tucker, A. S., et al., *Science* 282: 1136-1138 (1998); Zimmerman, L. B., et al., *Cell* 86: 599-606 (1996)) In brief, 25 ug of Affi-blue agarose beads were incubated with 100 ug/ml albumin, recombinant human BMP-2, or recombinant noggin for 2 hours and then washed 3 times with PBS immediately prior to use. In separate experiments, the beads were not washed prior to injection. The coated beads were injected with the A549 cells into nude mice subcutaneously. To assess tumor growth after 12 or 19 days, the length, width, and depth of the tumors were measured in mm. To assess tumor vasculature, tissue including a tumor was harvested after six days. Gross observations of the tissue were made. In addition, the tissue was stained with anti-CD31 antibody, which recognizes endothelial cells. Vessels in five high power fields were counted by a person blinded to how the tumors were created.

Example 6

Effect of BMP-2 and Noggin on VEGF and Sonic Hedgehog; Expression Western Blot Analysis of VEGF and Sonic Hedgehog in Presence of BMP-2 and Noggin Western blots, as described above, were performed on total cellular protein samples and cell culture media samples. The primary antibodies used to detect VEGF and sonic hedgehog were anti human VEGF from R & D Systems (Minneapolis, Minn.) and anti human sonic hedgehog from Santa Cruz (Santa Cruz, Calif.), respectively.

ELISA of VEGF in Presence of BMP-2 and Various Concentrations of Noggin

The sandwich ELISA method was used to determine VEGF concentrations in the cell culture media of A549 cells treated with noggin and in the cell culture media of human aortic endothelial cells treated with BMP-2. 100 ul of the monoclonal capture antibody, diluted in carbonate buffer (sodium bicarbonate, sodium carbonate, pH 9.0), was added to each well of a MaxiSorb Nunc-Immuno plate and incubated overnight at 4° C. The plates were washed two times with washing buffer (1x PBS with 0.0005% tween-20). Then, 200 ul of blocking buffer (1× PBS with 1% BSA) was added per well and incubated for 2 hours at room temperature. The plates were then washed 4 times with washing buffer.

The recombinant protein standards and samples (100 ul per well) were added and the plate was then incubated overnight at 4° C. The plates were washed 5 times with washing buffer. The biotinylated detection antibody was diluted in incubation buffer (1× PBS with 10% fetal bovine serum) for a final concentration of 1 ug/ml. 100 ul of the detection antibody was added per well and incubated for 1 hour on a shaker at room temperature. The plates were washed 6 times with washing buffer and 100 ul of streptavidin-HRP conjugate (1:10,000) was added per well. The plates were incubated for 45 minutes at room temperature on a shaker and then washed 6 times with washing buffer. 100 µl/well of the substrate reagent (0.2 M citrate buffer, 1 mg/ml o-phenylenediamine dihydrocholoride (OPG), 3% hydrogen peroxide) was added and covered with aluminum foil for ten minutes. The reaction was stopped with 100 µl/well of 2M sulfuric acid and absorbance determined using an automated plate reader with a 490/690 filter. The protein concentration was then determined from the standard curve.

Example 7

Identification of BMP-2 as a Stimulant of Human Lung Cancer Cell Migration and Invasion Migration Assay in Monolayer Culture To detect BMP-induced migration in a monolayer culture, recombinant human BMP-2 (R & D systems, Minneapolis, Minn.) was coated to Affi-Blue agarose beads (Bio Rad, Hercules, Calif.) as described in the literature. (Vainio, S.; et al., *Cell* 75: 45-58 (1993); Sloan, A. J., et al., Arch Oral Biol. 44: 149-156 (1999)) Briefly, 100 ml of the Affi-Blue agarose beads were incubated with either 10 ml of recombinant BMP-2 reconstituted in PBS with gelatin (100 mg/ml) or PBS alone at 37° C. for 2 hours, washed with PBS, and reconstituted with 40 ml of PBS. Glass cover slips were coated with serum free media containing BSA, fibronectin and collagen and 50,000 cells were plated per cover slip in serum free media. Two microliters of the Affi-Blue agarose beads coated with recombinant BMP-2 or dilution buffer were placed in linear fashion next to the cover slips.

Chemotactic Assay

In the chemotactic assay, fifty thousand cells were placed in the upper chamber of an 8 micron transwell migration chamber (Becton Dickinson, Bedford, Mass.) and 300 ml of serum free media with 0 ng/ml, 1 ng/ml, 10 ng/ml, 100 ng/ml, 500 ng/ml, or 1000 ng/ml recombinant human BMP-2 placed in the lower well. After 24 hours, the filters were then removed and the top of the filter wiped with a cotton swab and the cells that migrated through the filters were stained with Syto-16 intercalating dye. Five high power fields were counted using fluorescent microscopy. To show that noggin inhibits BMP-2 induced migration, the experiment was also performed with each of the following in the lower well of the transwell chamber: media alone, recombinant BMP-2 (500 ng/ml), and noggin (10 ug/ml) with recombinant BMP-2 (500 ng/ml).

MATRIGEL Invasion Assay

Invasion was studied using transwell chambers coated with 100 ml of MATRIGEL (Becton Dickinson). Fifty thousand cells were placed in the upper chamber and 300 ml of serum free media with 0 ng/ml, 10 ng/ml, 100 ng/ml, 500 ng/ml, or 1000 ng/ml recombinant BMP-2 placed in the lower wells. After 48 hours, the MATRIGEL was removed and cells that had migrated through the filter were stained with Syto-16 intercalating dye and 5 high power fields counted using fluorescent microscopy.

Example 8

BMP-2, but not BMP-4, is Overexpressed in NSCLC and Stimulates Tumor Growth

Cell Lines

The immortalized normal human bronchial epithelial cells (BEAS-2B) and human lung cancer cell lines A549 and H7249 were cultured in Dulbecco's Modified Eagles medium (DME) with 0.5% fetal bovine serum (FBS) containing 1% penicillin/streptomycin, and 1% glutamine. These cells were obtained and preserved as described in Example 3.

Antibodies and Recombinant Proteins

Monoclonal anti-human BMP-2 antibodies MAB355 and MAB3551 (R & D Systems, Minneapolis, Minn.) were used to detect BMP-2 by Western blot analysis. Goat anti-human BMP-2/4 (R & D Systems) was used for immunohistochemistry. Goat anti-human type IA, IB, and II BMP receptor antibodies, mouse IgG antibody, and anti-human BMP-4 monoclonal antibody were obtained from R & D Systems. A goat anti-BMP-4 antibody was obtained from Santa Cruz (Santa Cruz, Calif.). Both anti-BMP-4 antibodies were used to assess BMP-4 expression by Western blot analysis. Recombinant human BMP-2, recombinant human BMP-4, and recombinant noggin were purchased from R & D Systems. Recombinant proteins were reconstituted in phosphate buffered saline (PBS) with 0.1% gelatin. An anti-BMP-2 monoclonal antibody, which was a gift from the Genetics Institute (Cambridge, Mass.), was co-injected with the A549 cells into female NCJ nude mice.

Migration Assay

To examine whether BMP-2 enhanced the migration of lung cancer cells fifty thousand A549 or H7249 cells were placed in the upper chamber of an 8-micron transwell migration chamber (Becton Dickinson, Bedford, Mass.). In the lower well was 300 μl of LHC serum free media (BioFluids, Rockville, Md.) containing recombinant human BMP-2 (1, 10, 100, or 500 ng/ml) or an equal volume of PBS with 0.1% gelatin. After 24 hours, the filters were removed and the top of the filter was wiped with a cotton swab. Cells that had migrated through the filters were stained with Syto-16 intercalating dye (Molecular Probes, Eugene, Oreg.). Five high power fields were counted using fluorescent microscopy. To inhibit BMP-2, 500 ng/ml of recombinant BMP-2 was incubated with 10 μg/ml of recombinant noggin in serum free media at 37° C. for one hour before placing the BMP-2 into the lower chamber.

Migration Assay In Monolayer Culture

To assess whether BMP-2 stimulates the migration of tumor cells growing in monolayer culture, it was examined whether A549 and H7249 cells growing on glass cover slips migrated toward Affi-Blue beads coated with recombinant human BMP-2. Recombinant human BMP-2 (R & D systems, Minneapolis, Minn.) was coated with Affi-Blue agarose beads (Bio Rad) as previously described. Briefly, 100 μl of the Affi-Blue agarose beads were incubated with 10 μl of BMP-2 (100 μg/ml) or PBS with 0.1% gelatin at 37° C. for 2 hours. The beads were then washed with PBS and reconstituted with 40 μl of PBS. Glass cover slips were coated with serum free media containing BSA, fibronectin and collagen and 50,000 cells were plated per cover slip. After allowing the cells to attach for 12 hours the cover slips were placed into a 6 well plate containing serum free media. Two microliters of the Affi-Blue agarose beads coated with recombinant BMP-2 or dilution buffer were placed in linear fashion next to the cover slips. Five days later the cells, which migrated off the cover slips, were photographed.

Invasion Assay

The next issue was whether BMP-2 enhanced the invasiveness of tumor cells by determining whether recombinant BMP-2 stimulated the migration of A549 and H7249 cells through the extracellular tumor matrix, MATRIGEL (Becton Dickinson, Bedford, Mass.). 100 μl of MATRIGEL was placed in the upper well of an 8-micron transwell migration chamber. Fifty-thousand A549 or H7249 cells were placed in the upper chamber and 300 μl of LHC serum free media supplemented with recombinant human BMP-2 (1, 10, 100, or 500 ng/ml) or an equal volume of PBS with 0.1% gelatin was added to the lower well. After 48 hours, the MATRIGEL the cells on the upper side of the filter were removed using a cotton swab. Cells that migrated through the filter were stained with Syto-16 nuclear dye and examined by fluorescent microscopy.

Growth Assay

To determine the effects of BMP-2 on the monolayer growth of the A549 cells, seventy-five thousand cells were plated onto 6 well tissue culture plates containing LHC serum free media. After allowing the cells to adhere for 12 hours they were treated with recombinant BMP-2 or with vehicle alone (PBS with 1% gelatin). Two days later cells were detached and counted using a hemacytometer.

Western Blot Analysis

Tissue specimens in a modified RIPA buffer were briefly sonicated on ice. Protein concentration was measured using the Bradford assay. Protein samples were prepared under reducing conditions. Total cellular protein was analyzed by a 15% SDS-PAGE, transferred to nitrocellulose (Schleicher and Schuell, Keene, N.H.) at 35 V for 16 hours at 4° C. The blots were then incubated overnight at 4° C. with the appropriate primary antibody in Tris-buffered Saline with 1% TWEEN (TBST) and 5% nonfat dried milk. Specific proteins were detected using the enhanced chemiluminescence system (Amersham, Arlington Heights, Ill.). Relative BMP-2 expression was analyzed using NIH Imaging. Pixel density of the mature BMP-2 protein and actin were determined on each of the developed immunoblots. A relative actin value was determined in each sample by dividing its pixel density by the pixel density from the sample with the highest expression of actin. The sample with the highest actin level on the blot was given a value of 1 and the remaining samples as a fraction of that value. The relative BMP-2 expression was determined by dividing the BMP-2 pixel density by its relative actin value.

Northern Blot Analysis

The m-RNA obtained from the driver and tester was size fractionated on a 1% agarose-formaldehyde gel in a MOPS (0.2M 3-N-morpholino-propanesulfonic acid/0.05M Na Acetate/0.01 M EDTA) buffer. The m-RNA was transferred to a nitrocellulose membrane by capillary transfer. The m-RNA was cross-linked to the membrane using ultraviolet light. The subtracted BMP-2/4 cDNA was radiolabeled with $p^{32}$ using the All-In-One Random Priming mix (Sigma, St. Louis, Mo.). The probe was denatured by boiling and incubated with the blots in PerfectHyb Plus hybridization buffer (Sigma) for 12 hours. Membranes were washed in high stringent conditions and exposed to KODAK XAR film with an intensifying screen.

RT-PCR

Total RNA was extracted from a patient derived tissue sample using TRIZOL (Gibco, Rockville, Md.). First strand cDNA was synthesized using the Advantage for PCR kit (Clontec, Palo Alto, Calif.) following the manufacturer's instructions. BMP-2 Cdna was amplified using primers (F) 5'-cct gag cga gtt cga gtt g-3' [SEQ ID NO: 17], and (R) 5'-cac tcg ttt ctg gta gtt c-3' [SEQ ID NO: 18] at 95° C. for 1 minute, 50° C. for 1 minute, 72° C. for 2 minutes for 30 cycles. The expected size of the amplified BMP-2 was 230 base pairs. BMP-4 was amplified using primers (F) 5'-tac ctg aga cgg gaa gaa a-3' [SEQ ID NO: 19] and (R) 5'-cca gac tga agc cgg taa ag-3' [SEQ ID NO: 20] at 95° C. for 1 minute, 56° C. for 1 minute, 72° C. for 2 minutes for 33 cycles. The expected size of the amplified BMP-4 was 211 base pairs. The amplified bands were gel purified and sequenced at the core UMDNJ-RWJMS sequencing facility using an ABI PRISM 377 DNA sequencer.

Cloning and Transfection of BMP-2

Full-length human BMP-2 cDNA (gift from Genetics Institute) was cloned into the pcDNA3.1 expression vector (Invitrogen) in both the sense (BMP-2-S) and anti-sense (BMP-2-AS) directions. A549 cells with forced expression of BMP-2-S were also co-transfected with a pCMV-EGFP vector (BD Biosciences, Palo Alto, Calif.) which constitutively expresses green fluorescent protein (GFP). Transfection was performed by electroporation using 30 μg of BMP-2-S and 10 μg of GFP at 0.975 μF capacitance and 0.2 Kv. Control cells were transfected with the pcDNA3.1 and the GFP expression vector (A549-GFP). Transfected cells were cultured in 5% FCS DME media containing 50 μg/ml of neomycin. After expanding the transfected A549 cells in selective medium, cells expressing GFP were bulk sorted using flow cytometry. To obtain A549 cells expressing BMP-2 in the anti-sense direction, A549 cells were transfected with BMP-2-AS or pcDNA3.1 vector (A549-V) by electroporation. These cells were not co-transfected with the GFP expression vector and transfected cells were obtained by culturing in selective media. BMP-2-AS and A549-V sub-clones were obtained by limiting dilution in 96 well plates placing 1 cell for every 5 wells. Seven sub-clones of BMP-2-AS and A549-V were then selected.

Immunohistochemistry

Tissue samples were placed in Optimal Cutting Temperature (OCT) and snap frozen in liquid nitrogen. Four micron Cryostat sections were air dried before being fixed in cold acetone for 10 minutes. Sections were washed in cold 0.5M PBS and intrinsic peroxidase was quenched with 0.03% periodic acid for 20 minutes at room temperature. Sections were then rinsed in cold PBS and 0.5% BSA/PBS was applied to the slides for 15 minutes in a humidified chamber. Biotynilated polyclonal BMP-2/4 antibody (R&D Systems) was applied at a concentration of 2 ug/ml in 1% BSA/PBS and incubated overnight at 4° C.

Negative controls were slides in which the samples were incubated overnight at 4° C. with normal rabbit serum without primary antibody. In addition, we performed a competition assay by incubating the biotynilated BMP-2/4 antibody with recombinant human BMP-2 at a 1:10 Molar ratio for 2 hours before the overnight incubation. Following the overnight incubations the slides were washed with cold PBS and incubated for one hour in Streptavidin horseradish peroxidase (Dako) at a 1:500 dilution in 1% BSA/PBS. Slides were then counterstained in 0.7% Toluidine Blue.

Effect of BMP-2 on Tumor Growth in Nude Mice Studies

To assess the effects of BMP-2 on tumor growth in vivo, A549 cells were co-injected subcutaneously into female NCJ athymic nude mice with recombinant BMP-2 or the BMP-2 antagonist noggin Recombinant protein was delivered to the tumors using Affi-Blue agarose beads as previously described. In brief, 25 μg of Affi-Blue agarose beads were incubated with 20 μl of 100 μg/ml of BSA, recombinant human BMP-2, or noggin for 2 hours, and then washed 3 times with PBS immediately prior to use. In separate experiments, the beads were not washed prior to injection. The coated Affi-Blue agarose beads were co-injected with the $10^7$ A549 cells subcutaneously into the flanks of NCJ nude mice. In a separate study $10^7$ A549 cells were co-injected with 20 μg of an anti-BMP-2 monoclonal antibody reported to inhibit its activity. As a control, A549 cells were co-injected with 20 μg of an isotype control antibody. Fourteen to 19 days following injection the animals were sacrificed and the tumors were removed and measured in 3 dimensions (length×width×depth). The mice studies were approved by the Robert Wood Johnson Medical School Institutional Animal Care and Use Committee.

Statistical Analysis

Assessment of recombinant BMP-2 protein and recombinant Noggin on tumor growth in athymic nude mice was analyzed from 5 independent experiments. In vivo studies using an anti-BMP-2 antibody were performed twice. All other experiments were performed at least 3 times. The size of tumors formed from A549 cells treated with recombinant BMP-2, recombinant noggin, or anti-BMP-2 antibody is reported as the mean+SEM percentage of tumors formed from controls. Results were evaluated by one-way ANOVA using the Student-Newman-Keuls procedure for adjustment of multiple pairwise comparisons between treatment groups. Differences with P values <0.05 were considered statistically significant.

Representational Difference Analysis (RDA)

The RDA subtraction technique was performed to identify m-RNA that is uniquely or highly expressed in human lung carcinomas in comparison to normal bronchial epithelium. cDNA from immortalized human bronchial epithelial cells (IHBE) was hybridized in excess (driver) to cDNA obtained from a patient derived NSCLC (tester). The known genes identified by RDA were alpha-1-antitrypsin, cytokeratin 6, and BMP-2/4. It was not determined whether the sequenced cDNA was BMP-2 or BMP-4 because the amplified region (b.p. 766 to 863) is conserved in both. Alpha-1-antitrypsin has previously been reported to be over-expressed in 87% of human lung carcinomas. Since BMP-2/4 are powerful morphogens that have not been fully characterized in cancer, their expression and biological activity was further examined in human lung carcinomas.

BMP-2/4 mRNA Expression in Human Lung Carcinomas

The BMP-2/4 cDNA obtained from the RDA was labeled with $P^{32}$ and hybridized to a Northern blot containing the original m-RNA from the IHBE cells (driver) and NSCLC (tester). This blot revealed high expression of the BMP-2/4 mRNA in the tumor, with no expression found in the IHBE cells. RT-PCR confirmed that BMP-2 mRNA was not expressed in the IHBE. BMP-2 expression was identified in the A549 human lung cancer cell line. However, BMP-4 expression was detected by PCR in the IHBE cells. Next, it was examined whether the BMP-2 and BMP-4 m-RNA was expressed in other NSCLC. All 4 of the human lung tumors examined by RT-PCR demonstrated BMP-2 and BMP-4 expression. Sequencing of the PCR product confirmed the primers were specific for BMP-2 or BMP-4.

The Mature BMP-2 Protein is Highly Over-Expressed in Human Lung Carcinomas

The BMP-2 and BMP-4 proteins are translated as precursor proteins and must be cleaved by a proprotein convertase to produce a mature active peptide. The next study examined whether the mature BMP-2 and/or BMP-4 proteins are expressed in patient derived lung carcinomas. Immunoblots probed with a monoclonal BMP-2 antibody showed high expression of a 14 kD mature BMP-2 protein in 11 of 12 NSCLC examined. In comparison, little to no expression of the mature BMP-2 protein in 10 normal lung tissue specimens was found. When the level of BMP-2 expression was assessed relative to the level of actin by quantitative scanning, BMP-2expression was found to be 26 times higher in the NSCLC than that of normal lung tissue. Expression of BMP-2 was not increased in benign interstitial lung disease or a benign lung tumor (hamartoma). Recombinant human BMP-2 served as a positive control. BMP-2 was also found to be expressed in the A549 and H7249 human lung cancer cell lines. The bone forming osteosarcomas have previously been reported to express BMP-2/4 by immunohistochemistry. As expected, the SoAS osteosarcoma cell line also expressed a 14 kD mature BMP-2 protein.

It was additionally discovered that the monoclonal anti-BMP-2 antibody (MAB355) used in the above experiments cross reacts with recombinant BMP-4 protein. Therefore, the study probed the immunoblots with a second monoclonal anti-BMP-2 antibody (MAB3551), which is reported to be specific for BMP-2. The studies confirmed that this antibody does not recognize recombinant BMP-4 protein. The MAB3551 antibody also showed that the mature BMP-2 is over-expressed in NSCLC. The MAB3551 anti-BMP-2 antibody recognized predominately a 17 kD mature BMP-2 protein, but also demonstrated expression of a 14 kD mature protein in NSCLC.

Difference in the expression pattern between the two antibodies can be explained by the immunogens used to produce these anti-BMP-2 antibodies. The MAB355 antibody Was produced against an Escherichia coli derived mature human BMP-2 protein (non-glycosylated). The MAB3551 monoclonal antibody was raised against a glycosylated mature human BMP-2 protein (NSO derived recombinant human BMP-2). Although the MAB355 antibody recognized predominately a 14 kD protein, expression of a 17 kD protein on some of the immunoblots was found. The predicted size of BMP-2 under reducing conditions is 14 kD, however, following glycosylation BMP-2 is reported to be 17 kD. These data suggest that lung carcinomas produce predominately a 14 kD non-glycosylated BMP-2 protein. Prior studies have shown that glycosylated and non-glycosylated mature BMP-2 proteins have equivalent biological activity, in vivo.

Next examined was whether the mature active BMP-4 protein is expressed in. human lung tumors. No detectable expression of the mature BMP-4 protein could be seen in either malignant or normal lung tissue when probing immunoblots with a BMP-4 specific monoclonal antibody. Using a second antibody specific for BMP-4, was still undetectable expression of the mature BMP-4 protein. To verify further the MAB355 anti-BMP-2 antibodies recognized the native mature BMP-2 protein, full length human BMP-2 cDNA was transfected into the A549 cells (BMP-2-S). The cell culture media was obtained from the BMP-2-S and vector control A549 cells and Western blot analysis performed. Immunoblots probed with the MAB355 anti-BMP-2 antibody showed higher expression of the 14 kD BMP-2 protein in the BMP-2S cells compared to controls. In addition, BMP-2 cDNA was transfected in the anti-sense direction into the A549 cells. All 7 subclones containing the anti-sense BMP-2 cDNA had a lower expression of the 14 kD protein on immunoblots probed in comparison to the 7 subclones transfected with insertless vector. Together these data demonstrate that the mature BMP-2, but not the mature BMP-4 protein, is highly over-expressed in human lung carcinomas.

To help determine which cells are expressing BMP-2 in the NSCLC, BMP-2 expression in a NSCLC by immunohistochemistry was examined. BMP-2 expression was detected in the cytoplasm of the tumor cells. BMP-2 was not found to be expressed in normal lung tissue or surrounding stromal cells. To confirm the antibody recognized BMP-2, the antibody was incubated with recombinant human BMP-2 prior to immunostaining. This led to a complete inhibition of the BMP-2 signal in the tumor specimen.

Expression of BMP-2 Receptors in Human Lung Carcinomas

BMP-2 induces a physiological response through the activation of receptors specific for the BMPs. Intracellular activation begins with BMP-2 binding to either type IA or IB BMP receptors, which leads to the binding of this complex to the type II BMP receptor. The type II receptor phosphorylates the type I receptor, which then directly phosphorylates the Smad transcription factors. It was found that the BMP type IA, IB, and II receptors are expressed in both primary lung tumors and normal lung tissue. However, in contrast to the high level of expression of the BMP-2 ligand in primary lung cancers, the same level of expression of the type IA receptor between the lung carcinomas and normal lung tissue was found. The expression of the type IB and type II receptors was lower in the lung tumor than that of normal lung tissue. The IHBE, A549 and H7249 cells were also found to express type IA, IB and type II receptors. These data suggests that both cancer cells and normal lung tissue have the potential capability of being activated by the BMP-2 ligand.

BMP-2 Stimulates the Migration and Invasiveness of Human Lung Cancer Cells

BMP-2 and BMP-4 have been shown to stimulate the migration of non-cancerous human cells. Since migration is important for tumors to invade and metastasize, it was examined whether recombinant BMP-2 stimulates the migration of the A549 and H7249 human lung cancer cell lines in vitro. When recombinant BMP-2 was placed in the lower well of a migration chamber, it caused a dose responsive increase in the migration of both the A549 and H7249 cells. The BMP-2 antagonist, noggin, completely inhibited the ability of BMP-2 to stimulate the migration of the A549 cells. Next, it was determined whether BMP-2 enhanced the migration of the lung cancer cell lines growing in monolayer cell culture. The A549 and H7249 cells were cultured on glass cover slips and placed in 6 well plates containing Affi-Blue agarose beads coated with PBS with 0.1% gelatin or recombinant BMP-2. After 5 days, the number of cells that had migrated off the cover slips and were growing in the six well plate was assessed. There was only an occasional cluster of A549 or H7249 cells growing on the six well plates when cultured with control beads. However, when A549 and H7249 were cultured with Affi-Blue agarose beads coated with recombinant BMP-2, there was consistently a large number cells that migrated off the glass cover slips and were growing on the six well plate.

BMP-2 stimulation of the migration of the A549 and H7249 lung cancer cells through the tumor matrix MATRI- GEL was examined to assess whether BMP-2 may enhance the invasiveness of cancer cells. Recombinant BMP-2 again produced a dose responsive increase in the migration of both the A549 and H7249 cells through the MATRIGEL coated chambers.

In Vitro Growth Effects of BMP-2 on the A549 Cells

Next assessed were the effects of recombinant BMP-2 on the growth of the A549 cells in vitro. It was found that recombinant BMP-2 caused only minimal growth suppression of the A549 cells. In serum free conditions, BMP-2 at a 100 ng/ml caused a 15% decrease in growth of the A549 cells after 2 days. Lower concentrations of BMP-2 had no effect on the growth of the A549 cells.

BMP-2 Enhances in vivo Tumor Growth

Since BMP-2 is a secreted protein, it was hypothesized that it may effect the growth of the A549 cells differently in vivo than it does in vitro. To answer this question, required assessment of tumor growth of the A549 cells in athymic nude mice treated with recombinant BMP-2 or by inhibiting BMP-2 activity with noggin or an anti-BMP-2 antibody. Noggin coated Affi-Blue agarose beads were co-injected with the A549 cells subcutaneously into nude mice. Noggin has a high binding affinity for BMP-2 and BMP-4 preventing their activation of the BMP receptors. Noggin treated 549 cells (n=14) consistently formed tumors which were less than half the size of A549 cells treated with albumin (n=15). Co-injection of A549 cells with an anti-BMP-2 monoclonal antibody previously reported to inhibit BMP-2-induced migration of smooth muscle cells, (n=4) also produced an approximately 60% reduction in tumor growth when compared to mice co-injected with a control antibody (n=4).

A549 cells co-injected into nude mice with Affi-Blue agarose beads coated with recombinant human BMP-2 (n=15) formed tumors which were approximately 50% larger than that of A549 cells treated with BSA (n=15). Tumors were stained with hematoxylin and eosin and examined by a surgical pathologist for the presence of bone and/or cartilage. There was no evidence of bone and/or cartilage in any of the tumor formed from A549 cells treated with recombinant BMP-2. Together these data indicate that BMP-2 produced from the A549 cells enhances tumor growth in vivo, which is not associated with the formation of bone.

Example 9

BMP-2 Induces Proliferation of Lung Cancer Cells in an Autocrine Manner

Cell Lines and Acquisition of Tissue Specimens

The immortalized normal human lung cancer cell line A549 were cultured in Dulbecco's Modified Eagles medium (DME) (Sigma Aldrich, St. Louis, Mo.) with 5% fetal bovine serum (FBS) containing 1% penicillin/streptomycin, and 1% glutamine. Cells were kept in a humidified incubator with 5% $CO_2$ at 37° C.

Antibodies and Recombinant Proteins

Primary antibodies against phosphorylated Smad 1 (Upstate Biotechnology, Lake Placid, N.Y.), ID1 (Santa Cruz, Santa Cruz, Calif.), cyclin E (Santa Cruz) phosphorylated ERK-½ (Promega, Madison, Wis.), Actin (Sigma, St. Louis, Mo.) were used for Western blot analysis. Antibody recognizing Smad 1, 5, and/or 8 (Santa Cruz, Santa Cruz, Calif.) was used in immunoblots and immunofluorescence studies. Recombinant human BMP-2 was purchased from R & D Systems. Recombinant proteins were reconstituted in phosphate buffered saline (PBS) with 0.1% gelatin.

Western Blot Analysis

Total cellular protein was obtained using RIPA buffer. Protein concentration was measured using the Bradford assay. Protein samples were prepared under reducing conditions. Total cellular protein was analyzed by a 5%-15% SDS-PAGE, transferred to nitrocellulose (Schleicher and Schuell, Keene, N.H.) at 35 V for 16 hours at 4° C. The blots were then incubated overnight at 4° C. with the appropriate primary antibody in either Tris-buffered Saline with 1% Tween (TBST) and 5% nonfat dried milk or Membrane Blocking Solution (Zymed, San Francisco, Calif.). Specific proteins were detected using the enhanced chemiluminescence system (Amersham, Arlington Heights, Ill.).

Proliferation Assay

A549 cells were plated at $2.0 \times 10^5$ cells/well in 6 well tissue culture plates (Falcon, Franklin Lakes, N.J.) in DMEM supplemented with 5% FCS and allowed to adhere overnight. Experiments were then performed in serum free media (SFM) (LHC-8, Biofluids, Rockville, Md.) or DMEM 5% FCS. Cells were treated with 1, 10, or 100 ng/ml BMP-2 or 4 mM HCl/0.1% BSA (vehicle control) and for either 6 hours or 24 hours. In brief, cells were incubated with 4° C.i/ml $H^3$ thymidine at 37° C. for 1 hour. Cells were washed twice with ice cold PBS and fixed with 5% trichloroacetic acid for 10 minutes. Cells were then washed with 70% ethanol, lysed with 1% SDS/10 mM NaOH and incorporated $H^3$ thymidine measured in a scintillation counter. The results of this experiment are shown in FIG. 24.

Smad Localization

A549 cells were grown on glass cover slips were then cultured in DMEM 5% FCS or SFM. A549 cells were then treated with 10 ng/ml BMP-2 for 0, 15, 30, 45, and 60 minutes. Cells were fixed with 3.7% formaldehyde, permealized with 0.5% Triton X, and blocked with 1% BSA/PBS. Cells were incubated overnight with a 1:50 dilution of anti-Smad 1/5/8 antibody at 4° C. and AlexaFluor 488 anti-goat was used as the secondary antibody (Molecular Probes, Eugene, Oreg.). To inhibit BMP-2, 40 ng of recombinant noggin was added to the BMP-2 treated cells. Negative controls included primary antibody incubated with blocking peptide (Santa Cruz) and AlexaFluor 488 without primary antibody. Smad 1/5/8 localization was assessed by immunofluorescent microscopy.

In Vivo Tumor Growth

To assess the effects of BMP-2 on tumor growth in vivo A549 cells were coinjected subcutaneously into female NCJ athymic nude mice with recombinant BMP-2 or the BMP-2 antagonist, noggin. Recombinant protein was delivered to the tumors using Affi-Blue agarose beads as previously described. 25 µg of Affi-Blue agarose beads were coated with 20 µl of 100 µg/ml of albumin, or recombinant human BMP-2. The coated Affi-Blue agarose beads were co-injected with the $10^7$ A549 cells subcutaneously into the flanks of NCJ nude mice. Fourteen to 19 days following injection the animals were sacrificed and the tumors were snapped frozen in liquid nitrogen and protein collected for Western blot analysis. A section of the tumor was also placed in Optimal Cutting Temperature (OCT) then frozen for immunohistochemistry studies.

Apoptosis Studies—Immunohistochemistry

Frozen samples were cut with a dermatome to obtain 5 micron sections. The samples were incubated with a rat anti-Ki-67 antibody at a 1:20 dilution overnight at 4° C. The anti-rat IgG was incubated at a 1:300 dilution at room temperature for 20 minutes. Positive control included a mouse liver. Negative controls consisted of samples treated with secondary antibody alone.

Figure 25:
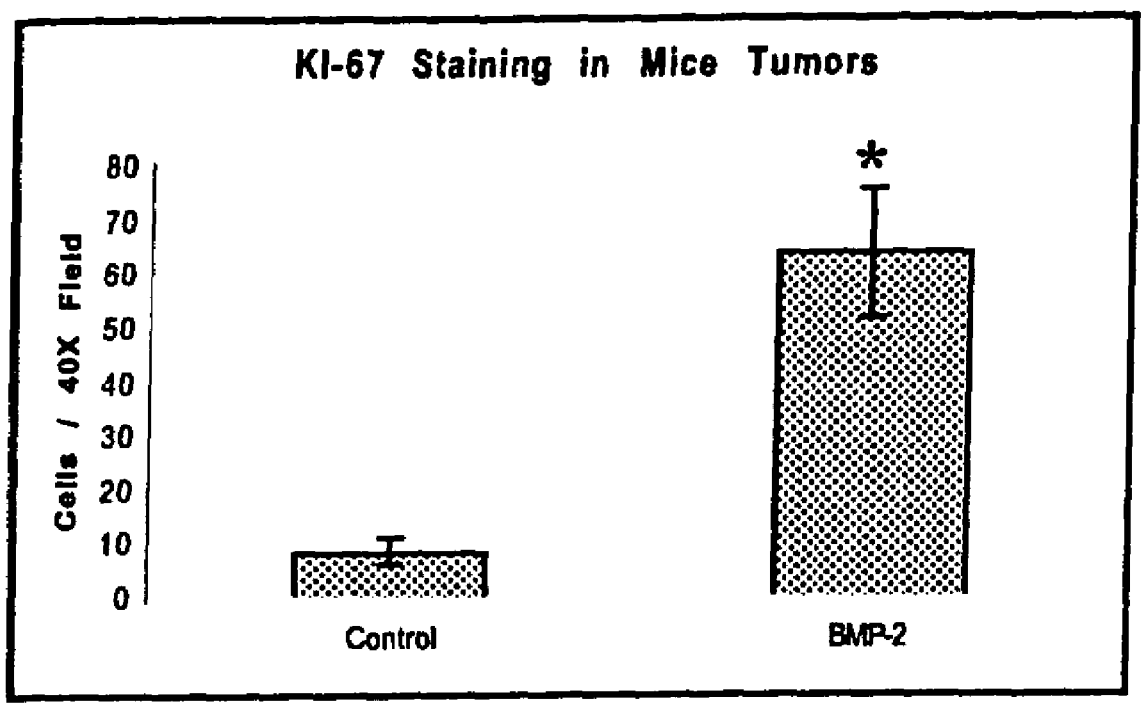
FIG. 25 is a bar graph representing KI-67 staining in mice tumors for a control and BMP-2 as measured in cells/40× field.
Figure 26:
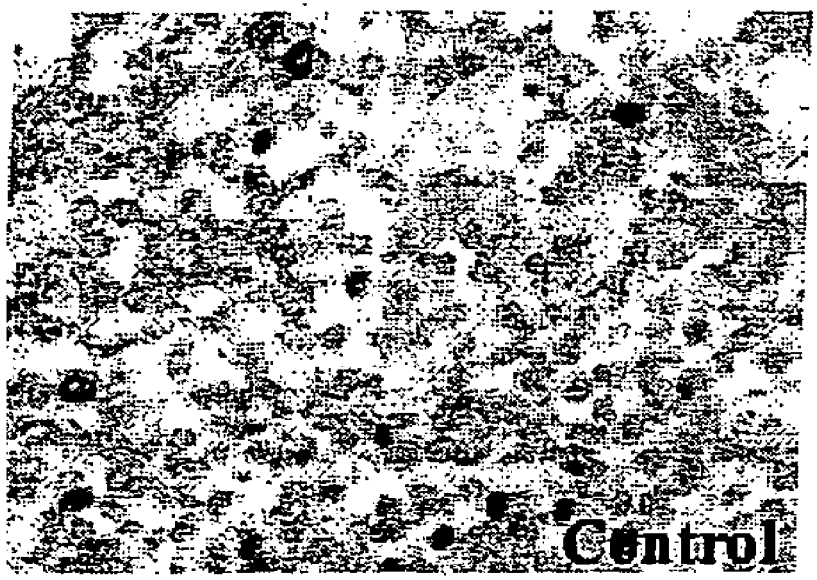
FIG. 26 is a photograph of the cells stained in FIG. 25, with both the control cells and BMP-2 cells shown.
Figure 26:
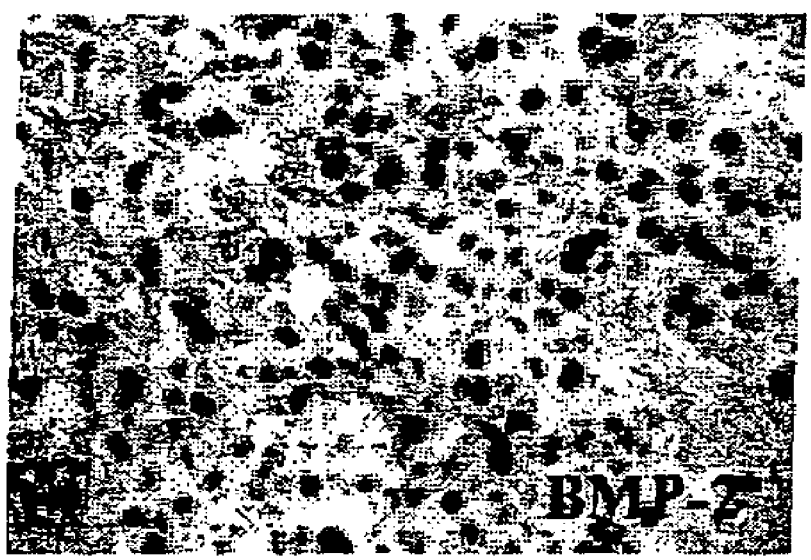

In brief, four micron sections were cut using a dermatome and placed on slides. Each sample was stained for Ki-67 using the M.O.M. kit (Vector Laboratories, Burlingame, Calif.) according to the manufacturer's protocol. The slides were blocked for 1 hour in blocking reagent and mouse anti-human Ki-67 monoclonal antibody was diluted to 1:100 in the blocking reagent and incubated overnight at 4° C. Each section was incubated with secondary antibody (1:250) for 10 minutes and then with Vectastain Elite ABC reagent as a tertiary conjugate for 5 minutes. DAB chromagen (DAKO, Carpenteria, Calif.) was used as the final stain and toluidine blue used for background staining. The graphical results of the cell growth with BMP-2 as compared to controls when examined in a 40× field are shown in FIG. 25. A photograph of the cell death in control cells as compared to the much more active cell growth in the BMP-2 treated cells is shown in companion FIG. 26.

Apoptosis Studies

A549 cells were plated onto 35 mm cell culture dishes at a density of 6×105 in DMEM supplemented with 5% FCS and allowed to adhere overnight. Cells were then cultured in DMEM 5% FCS or SFM and treated with 10 ng/ml or 100 ng/ml rBMP-24 for hours. Apoptosis was examined using JC-1 Mitochondrial Potential Sensor (Molecular Probes, Eugene, Oreg.) and by assessing nuclear condensation using ethidium bromide staining. JC-1 is a fluorescent dye, which specifically targets mitochondrial membranes. JC-1 has been used to detect membrane depolarization, which occurs during apoptosis. When the mitochondria are polarized the JC-1 forms J-aggregates, which become fluorescent red.

When the mitochondria are depolarized, JC-1 it does not accumulate in the nucleus and fluoresces green. JC-1 is added to live cells at 5 g/ml and then washed in PBS. The cells were placed the medium to incubate for 15 minutes in cell culture conditions. Cells were protected from light and washed twice with warmed 1× PBS and immediately observed under fluorescence to assay the apoptotic cell to live cell ratio.

Statistical Analysis

Assessment of recombinant BMP-2 protein and recombinant Noggin on tumor growth in athymic nude mice was analyzed from 5 independent experiments. In vivo studies using an anti-BMP-2 antibody were performed twice. All other experiments were performed at least 3 times. The size of tumors formed from A549 cells treated with recombinant BMP-2, recombinant noggin, or anti-BMP-2 antibody is reported as the mean+SEM percentage of tumors formed from controls. Results were evaluated by one-way ANOVA using the Student-Newman-Keuls procedure for adjustment of multiple pairwise comparisons between treatment groups. Differences with P values <0.05 were considered statistically significant.

Example 10

BMP-2 Enhances Neovascularization of Developing Tumors Cell Culture and Reagents HAEC and HUVEC were obtained from Bio-Whittaker (Walkersville, Md.). Endothelial cells were maintained in EBM-2 supplemented with 2% FCS and growth factors supplied in the bullet kit (Bio-Whittaker). The A549, A549-AS, and A549-vector lung cancer cell lines were prepared and maintained. Earlier recombinant BMP-2, noggin, and VEGF were purchased from R & D Systems (Minneapolis, Minn.). Primary antibodies against BMPR IA, BMPR IB, BMPR II (R & D Systems), phosphorylated Smad 1 (Upstate Biotechnology, Lake Placid, N.Y.), ID1 (Santa Cruz, Santa Cruz, Calif.), phosphorylated ERK-½ (Promega, Madison, Wis.), Actin (Sigma, St. Louis, Mo.) were used for Western blot analysis. Antibody recognizing Smad 1, 5, and/or 8 was used in immunofluorescence and immunoprecipitation studies (Santa Cruz, Santa Cruz, Calif.) and platelet-endothelial cell adhesion molecule-1 (PECAM-1) for immunohistochemistry (BD Pharmingen, San Diego, Calif.).

Migration Assay 3.0×104 HAEC cells in EBM-2 supplemented with 0.5% FCS and growth factors excluding VEGF (Bio-Whittaker) were placed in the upper chamber of a transwell migration chamber (Becton Dickinson, Bedford, Mass.). Medium containing 1 ng/ml BMP-2, 50ng/ml VEGF, or 4 mM HCl/0.1% BSA (vehicle control) was added to the lower chamber. After 24 hours the cells that had migrated were stained with Giemsa (Sigma) and ten 40× fields were counted.

Proliferation Assay

HAEC or HUVEC cells were plated at 2.0×105 cells/well in 6 well tissue culture plates (Falcon, Franklin Lakes, N.J.) in EBM-2 with 2% FCS. Cells were treated with 1, 10, or 100 ng/ml BMP-2 or vehicle control for 24 hours then pulsed with 4 Ci/ml 3H -thymidine for 1 hour. Cells were washed twice with cold PBS and fixed with 5% trichloroacetic acid for 10 minutes. Cells were treated with 70% ethanol, lysed with 1% SDS/10 mM NaOH, Incorporated 3H -thymidine was measured in a scintillation counter.

Smad Localization

HAEC or HUVEC cultured on glass cover slips were serum starved in EBM-2 deficient of FCS and VEGF for 6 hours. Then, the cells were treated with 10 ng/ml BMP-2 for 0, 15, 30, 45, and 60 minutes. Cells were fixed with 3.7% formaldehyde, permealized with 0.5% Triton X, and blocked with 1% BSA/PBS. Next, cells were incubated overnight with a 1:50 dilution of anti-pSmad 1/5/8 antibody at 4° C. and AlexaFluor 488 anti-goat was used as the secondary antibody (Molecular Probes, Eugene, Oreg.). To inhibit BMP-2, 40 ng of recombinant noggin was added to the BMP-2 treated cells. Negative controls included primary antibody incubated with blocking peptide (Santa Cruz) and AlexaFluor 488 without primary antibody. Smad 1/5/8 localization was assessed by immunofluorescent microscopy.

Western Blot Analysis and Immunoprecipitation

HAEC or HUVEC in EMB-2 with 2% FCS were treated with 10 ng/ml of recombinant BMP-2 for 0, 10, 20, 40, 60, and 120 minutes. Western blot analysis was performed on the cell lysate as in previous experiments. For immunoprecipitation studies, HAEC were treated for 20 minutes with 20 ng/ml of BMP-2. Cell lysate was incubated with anti-pSmad 1/5/8 antibody and separated by SDS-PAGE. Immunoblots were probed with anti-phosphoserine antibody (Zymed Laboratories, San Francisco, Calif.).

Tube Assay

Twenty-four well tissue culture plates were coated with 250 μl of MATRIGEL (BD Biosciences). HAEC or HUVEC were plated at 5.0×104 in 1 ml of EBM-2 supplemented with 1% FCS and all growth factors excluding VEGF. Cells were then treated with vehicle control, 500 pg/ml BMP-2, or 1 ng/ml BMP-2 for 18 hours at 37.degree. C. To inhibit BMP-2, 40 ng/ml of recombinant noggin was added to samples treated with BMP-2. Cells were photographed at 4× magnification and the formation of complete tubes counted in 3 fields.

BMP-2 Tumor Angiogenesis Assay

1 X107 A549 cells were subcutaneously injected into the flanks of NCR nude mice with Affi-Blue agarose beads (Biorad, Hercules, Calif.) coated with BSA or recombinant human BMP-2. 25 ug of Affi-Blue agarose were incubated with 2 g of BSA or recombinant BMP-2 for 2 hours and washed with PBS. Tumors were collected 4-6 or 12-14 days later. Tumors were placed in O.C.T and frozen in liquid nitrogen.

Blood vessels were detected by immunohistochemistry using anti-PECAM-1 antibody. Vessels were photographed and five 40X fields counted. The mice studies were approved by the Robert Wood Johnson Medical School Institutional Animal Care and Use Committee.

MATRIGEL Angiogenesis Assay

2×106 A549, A549-AS, or A549-vector cells in 100 µl DMEM with 5% FBS were mixed with 400 µl MATRIGEL and injected subcutaneously into nude mice. The MATRIGEL was supplemented with 835 ng of BSA or 670 ng recombinant BMP-2. To inhibit BMP-2, 670 ng of recombinant BMP-2 was incubated with 835 ng noggin for 2 hour at 37° C. prior to mixing with the MATRIGEL. The MATRIGEL plugs were harvested after 6 days, placed in O.C.T. and frozen in liquid nitrogen. Blood vessels were detected by immunochemistry. All of the vessels within the MATRIGEL plugs were photographed and counted.

Immunohistochemistry

Frozen samples were cut with a dermatome to obtain 5 micron sections. The samples were incubated with a rat anti-PECAM-1 antibody at a 1:20 dilution overnight at 4° C. The anti-rat IgG was incubated at a 1:300 dilution at room temperature for 20 minutes. Positive control included a mouse liver. Negative controls consisted of samples treated with secondary antibody alone.

Statistical Analysis

To evaluate multiple groups a one-way ANOVA followed by Fisher LSD post hoc test was used to compare individual means. To compare 2 groups a student t-test was used. Differences with P values <0.05 were considered statistically significant.

CITED REFERENCES

1. American Cancer Society. What Are The Key Statistics for Lung Cancer. 2003.
2. Warburton, D., Schwarz, M., Tefft, D., Flores-Delgado, G., Anderson, K. D. & Cardoso, W. V. 2000) *Mech Dev* 92, 55-81.
3. Celeste A J, I. J., Taylor R C, Hewick R M, Rosen V, Wan E A, Wozney J M (1990) Proc Natl Acad Sci USA 87, 9843-9847.
4. Erickson, D. M., Harris, S. E., Dean, D. D., Harris, M. A., Wozney, J. M., Boyan, B. D. & Schwartz, Z. (1997) *J Orthop Res* 15, 371-80.
5. An, J., Rosen, V., Cox, K., Beauchemin, N. & Sullivan, A. K. (1996) *Exp Hematol* 24, 768-75.
6. Abe, E., Yamamoto, M., Taguchi, Y., Lecka-Czemik, B., O'Brien, C. A., Economides, A. N., Stahl, N., Jilka, R. L. & Manolagas, S. C. (2000) *J Bone Miner Res* 15,663-73.
7. Vainio, S., Karavanova, I., Jowett, A. & Thesleff, I. (1993) *Cell*. 75, 45-58.
8. Weaver, M., Yingling, J. M., Dunn, N. R., Bellusci, S. & Hogan, B. L. (1999) *Development* 126, 4005-15.
9. Wozney, J. M., Rosen, V., Celeste, A. J., Mitsock, L. M., Whitters, M. J., Kriz, R. W., Hewick, R. M. & Wang, E. A. (1988) *Science* 242, 1528-34.
10. Willette, R. N., Gu, J. L., Lysko, P. G., Anderson, K. M., Minehart, H. & Yue, T. (1999) *J Vasc Res* 36, 120-5.
11. Cunningham, N. S., Paralkar, V. & Reddi, A. H. (1992) Proc Natl Acad Sci U S A 89, 11740-4.
12. Cui, Y., Jean, F., Thomas, G. & Christian, J. L. (1998) *Embo J* 17, 4735-43.
13. Sugiura (1999) *Biochem J* 338, 443-440.
14. Liu, F., Ventura, F., Doody, J. & Massague, J. (1995) *Mol Cell Biol* 15, 3479-86.
15. Ikeda, T., Takahashi, H., Suzuki, A., Ueno, N., Yokose, S., Yamaguchi, A. & Yoshiki, S. (1996) *Dev Dyvn* 206, 3 18-29.
16. Ten Dijke, P., Ichijo, H., Franzen, P., Schulz, P., Saras, J., Toyoshima, H., Heldin, C. H. & Miyazono, K. (1993) *Oncogene* 8, 2879-87.
17. Ten Dijke, P., Yamashita, H., Sampath, T. K., Reddi, A. H., Estevez, M., Riddle, D. L., Ichijo, H., Heldin, C. H. & Miyazono, K. (1994) *J Biol Chem* 269,16985-8.
18. Sakou, T., Onishi, T., Yamamoto, T., Nagamine, Sampath, T. & Ten Dijke, P. (1999) *J Bone Miner Res* 14, 1145-52.
19. Guo, W., et al. "Expression of bone morphogenetic proteins and receptors in sarcomas" *Clin. Orthop.* 365: 175-83 (1999).
20. Kleef, J., "Bone Morphogenetic Protein-2 exerts diverse effects on cell growth in vitro and is expressed in human pancreatic cancer in vivo" *Gastroenterology* 116: 1202-1216(1999).
21. Hatakeyama, S., et al., "Expression of bone morphogenetic proteins of human neoplastic epithelial cells" *Biochem Mol. Biol. Int.* 42(3): 497 (1997).
22. Kawamura, C., et al., "Bone morphogenetic protein-2 induces apoptosis in human myeloma cells with modulation of STAT3" *Blood* 96(6): 2005-11 (2000).
23. Soda, H. "Antiproliferative effects of recombinant human bone morphogenetic protein-2 on human tumor colony-forming units" *Anticancer Drugs* 9(4): 327-31 (1998).
24. Tada, A., et al., "Bone morphogenetic protein-2 suppresses the transformed phenotype and restores actin microfilaments of human lung carcinoma A549 cells" Oncol. Rep. 5(5): 137-40 (1998).
25. Tanaka, K., Abe, M., and Sato, Y. Roles of extra cellular signal-regulated kinase ½ and p38 mitogen-activated protein kinase in the signal transduction of basic fibroblast growth factor in endothelial cells during angiogenesis, Jpn J Cancer Res. 90:647-54., 1999.
26. Wu, L. W., Mayo, L. D., Dunbar, J. D., Kessler, K. M., Baerwald, M. R., Jaffe, E. A., Wang, D., Warren, R. S., and Donner, D. B. Utilization of distinct signaling pathways by receptors for vascular endothelial cell growth factor and other mitogens in the induction of endothelial cell proliferation, J Biol Chem. 275:5096-103., 2000.
27. Liu, S., Yu, D., Xu, Z. P., Riordan, J. F., and Hu, G. F. Angiogenin activates Erk ½ in human umbilical vein endothelial cells, Biochem Biophys Res Commun. 287:305-10., 2001.
28. Alani, et al., "Immortalization of primary human keratinocytes by the helix-loop-helix protein, Id-1," Cell Biology, Vol. 96, Issue 17, 9637-9641, 1999.
29. Folkman, J. *J. Nat'l Cancer Inst.* 82:4 (1990).
30. Zetter, B. *Annual Rev. Med.* 49:407 (1998); Ferrara, N. *Current Topics Microbiol. Immunol.* 237:1 (1999).
31. Oro, A. E., et al., "Basal carcinomas in mice overexpressing sonic hedgehog" *Science* 276: 817-21 (1997).
32. Zimmerman, L. B., et al., *Cell* 86: 599-606 (1996).
33. Tucker, A. S., et al., *Science* 282: 1136-1138 (1998).
34. Capdevilla, J., et al., *Developmental Biology* 197: 205-217 (1998).
35. Brunet, L. J., et al., *Science* 280: 1455-1447 (1998).
36. Millet, C., et al., "The human chordin gene encodes several differentially spliced variants with distinct BMP opposing activities" Mech. Dev. 106(1-2): 85-96 (2001).
37. Nickel, J., et al. "The Crystal Structure of the BMP-2: BMPR-IA Complex and the Generation of BMP-2 Antagonists" *The Journal of Bone & Joint Surgery* 83-A, Supp. 1, Part 1: 7-14 (2001).

38. Kirsch, T., et al. "BMP-2 antagonists emerge from alterations in the low-affinity binding epitope for receptor BMPR-II" *The EMBO Journal* 19(13):3314-24 (2000).

39. Ide, H., et al., "Cloning of human bone morphogenetic protein type IB receptor (BMPR-IB) and its expression in prostate cancer in comparison with other BMPRs" *Oncogene* 13(11): 1377-82 (1997).

40. Cameron, A., et al., "Polyarginines are potent furin inhibitors" *J. Biol. Chem.* 275: 36741-49 (2000).

41. Glavic, A., et al., "Xiro-1 controls mesoderm patterning by repressing BMP-4 expression in the Spemann organizer" *Dev. Dyn.* 222(3): 368-376.

42. E. Hay, et al., "Bone Morphogenetic Protein-2 Promotes Osteoblast Apoptosis through a Smad-independent, Protein Kinase C-dependent Signaling Pathway" J. Biol. Chem., Aug. 3, 2001; 276(31): 29028-29036.

43. Chen, et al., "Suppression of Tumor Mediated Necrosis Factor Apoptosis by Nuclear Factor B Independent Bone Morphogenetic Bone/Smad Signalling," J. Biol. Chem., Vol. 276, Issue 42, 39259-39263, 2001.

44. Izumi et al., "Bone Morphogenetic Protein-2 Inhibits Serum Depravation Induced Apoptosis of Neonatal Cardiac Myocytes through Activation of the Smad-1 Pathway," J. Biol. Chem., Vol. 276, Issue 33, 31133-31141, 2001.

45. Ogata, et al., "Bone Morphogenetic Protein 2 Transiently Enhances Expression of a Gene, Id (Inhibitor of Differentiation), Encoding a Helix-Loop-Helix Molecule in Osteoblast-Like Cells," Proc. Natl. Acad. Sci. USA. 1993; 90 (19): 9219-9222.

46. Locklin et al., "Assessment of gene regulation by bone morphogenetic protein 2 in human marrow stromal cells using gene array technology," J Bone Miner Res. 2001 Dec; 16(12):2192-204.

47. Hollnagel, et al., "Id Genes Are Direct Targets of Bone Morphogenetic Protein Induction in Embryonic Stem Cells," J Biol Chem, Vol. 274, Issue 28, 19838-19845, 1999.

48. Zebedee, et al., "Id proteins in cell cycle control and cellular senescence," Oncogene 20 (2001) 8317-8325.

49. Schindl, et al., "Level of Id-1 protein expression correlates with poor differentiation, enhanced malignant potential, and more aggressive clinical behavior of epithelial ovarian tumors," Clin Cancer Res 9: 779-785 (2003).

OTHER REFERENCES

*Thoracic Surgery* (Churchill Livingstone, N.Y., Edinburgh, London, Melbourne, Tokyo) (1995).

I claim:

1. A method for identifying a candidate agent for use in reducing vascularization in non-small cell lung tumors comprising:
   (a) contacting bone morphogenetic protein-2 (BMP-2) and BMP-2 receptor IB in the presence of a test agent under conditions suitable to permit the formation of a BMP-2/BMP-2 receptor complex, wherein said BMP-2 comprises the amino acid sequence of amino acids 283-396 of SEQ ID NO: 2 and wherein said BMP-2 receptor IB comprises the amino acid sequence of amino acids 14-502 of SEQ ID NO: 14;
   (b) determining the amount of the BMP-2/BMP-2 receptor complex formed in the presence of said test agent; and
   (c) determining that said test agent is a candidate agent for use in reducing vascularization in non-small cell lung tumors if the amount of the BMP-2/BMP-2 receptor complex formed in the presence of said test agent is lower than the amount of the BMP-2/BMP-2 receptor complex formed in the absence of said test agent,
   thereby identifying a candidate agent for use in reducing vascularization in non-small cell lung tumors.

* * * * *